US011806492B2

United States Patent
Oplinger et al.

(10) Patent No.: US 11,806,492 B2
(45) Date of Patent: Nov. 7, 2023

(54) TRANS MIDDLE EAR-INNER EAR FLUID FLOW IMPLEMENTATIONS

(71) Applicant: COCHLEAR LIMITED, Macquarie University (AU)

(72) Inventors: Kenneth Oplinger, Macquarie University (AU); Tommy Bergs, Macquarie University (AU); Soren Nilsson, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 568 days.

(21) Appl. No.: 16/649,757

(22) PCT Filed: Sep. 21, 2018

(86) PCT No.: PCT/IB2018/057325
§ 371 (c)(1),
(2) Date: Mar. 23, 2020

(87) PCT Pub. No.: WO2019/058330
PCT Pub. Date: Mar. 28, 2019

(65) Prior Publication Data
US 2020/0238062 A1 Jul. 30, 2020

Related U.S. Application Data

(60) Provisional application No. 62/561,985, filed on Sep. 22, 2017.

(51) Int. Cl.
*A61M 31/00* (2006.01)
*H04R 25/00* (2006.01)

(52) U.S. Cl.
CPC .......... *A61M 31/00* (2013.01); *H04R 25/558* (2013.01); *H04R 25/606* (2013.01);
(Continued)

(58) Field of Classification Search
CPC .......... A61M 31/00; A61M 2210/0668; A61M 2205/05; H04R 25/558; H04R 25/606; H04R 2460/13; H04R 23/02; A61F 11/045
See application file for complete search history.

(56) References Cited

U.S. PATENT DOCUMENTS 5,176,620 A * 1/1993 Gilman ............... H04R 25/606
607/57
5,951,601 A 9/1999 Lesinski et al.
(Continued)

FOREIGN PATENT DOCUMENTS

WO 9414293 A1 6/1994
WO 2014053826 A1 4/2014

OTHER PUBLICATIONS

Extended European Search Report for European Patent Application No. 18 857 995.7, dated May 11, 2021.
(Continued)

*Primary Examiner* — Nilay J Shah
(74) *Attorney, Agent, or Firm* — Piloff Passino & Cosenza LLP; Martin J. Cosenza

(57) ABSTRACT

A prosthesis including a device configured to deliver a therapeutic substance from outside a cochlea to inside the cochlea and configured to evoke a mechanically based hearing percept. In an exemplary embodiment, the device is configured to drive fluid into and out of the cochlea, thereby evoking a hearing percept.

29 Claims, 30 Drawing Sheets

(52) U.S. Cl.
CPC . *A61M 2205/05* (2013.01); *A61M 2210/0668* (2013.01); *H04R 2460/13* (2013.01)

(56) References Cited

U.S. PATENT DOCUMENTS

| | | | |
|---|---|---|---|
| 6,840,919 B1 | 1/2005 | Håkansson | |
| 7,959,606 B2 | 6/2011 | Rush et al. | |
| 8,128,551 B2 | 3/2012 | Jolly | |
| 8,147,544 B2 | 4/2012 | Lesinski et al. | |
| 2003/0097121 A1* | 5/2003 | Jolly | A61F 11/00 604/20 |
| 2004/0078057 A1* | 4/2004 | Gibson | A61N 1/0541 607/3 |
| 2005/0033377 A1* | 2/2005 | Milojevic | A61N 1/36038 607/45 |
| 2005/0238506 A1* | 10/2005 | Mescher | A61M 5/14276 417/413.1 |
| 2008/0009836 A1* | 1/2008 | Fiering | A61M 5/14276 604/891.1 |
| 2008/0064918 A1* | 3/2008 | Jolly | A61N 1/0541 607/137 |
| 2009/0306744 A1 | 12/2009 | Parker | |
| 2010/0324355 A1 | 12/2010 | Spitaels | |
| 2011/0112462 A1* | 5/2011 | Parker | H04R 25/70 604/20 |
| 2013/0261377 A1 | 10/2013 | Adamson et al. | |
| 2014/0018736 A1 | 1/2014 | Hessler | |
| 2015/0374964 A1* | 12/2015 | Verhoeven | A61M 5/1428 604/247 |
| 2017/0173315 A1 | 6/2017 | Verhoeven et al. | |

OTHER PUBLICATIONS

International Search Report & Written Opinion for PCT/IB2018/057325, dated Jan. 9, 2019.
Jeffrey T Borenstein, "Intracochlear drug delivery systems," Expert Opin Drug Deliv., Sep. 2011, pp. 1161-1174, vol. 8, No. 9.
Zhiqiang Chen et al., "Inner ear drug delivery via a reciprocating perfusion system in the guinea pig," J Control Release., Dec. 2005, vol. 111, No. 1.
Mark J. Mescher et al., "Fabrication Methods and Performance of Low-permeability Microfluidic Components for a Miniaturized Wearable Drug Delivery System," J Microelectromech Syst., Jun. 2009, pp. 501-510, vol. 18, No. 3.
Erin E. Leary Pararas et al., "Kinetics of reciprocating drug delivery to the inner ear," Journal of Controlled Release, Mar. 2011, pp. 270-277, vol. 152.
Erin E. Leary Pararas et al., "Microsystems technologies for drug delivery to the inner ear," Adv Drug Deliv Rev., Nov. 2012, pp. 1650-1660, vol. 64, No. 14.
Erin E. Leary Swan et al., "Inner ear drug delivery for auditory applications," Adv Drug Deliv Rev., pp. 1583-1599, Dec. 2008, vol. 60, No. 15.

\* cited by examiner

TRANS MIDDLE EAR-INNER EAR FLUID FLOW IMPLEMENTATIONS

CROSS-REFERENCE TO RELATED APPLICATIONS

This application claims priority to U.S. Provisional Application No. 62/561,985, entitled Trans Middle Ear-Inner Ear Fluid Flow Implementations, filed on Sep. 22, 2017, naming Kenneth OPLINGER of Macquarie University, Australia as an inventor, the entire contents of that application being incorporated herein by reference in its entirety.

BACKGROUND

Hearing loss is generally of two types, conductive and sensorineural. Sensorineural hearing loss is due to the absence or partial destruction of the cochlear hair cells which transduce sound into nerve impulses. Conductive hearing loss occurs when the natural mechanical pathways that provide sound in the form of mechanical energy to cochlea are impeded, for example, by damage to the ossicular chain or ear canal. Various hearing prostheses have been developed to provide individuals suffering from moderate to profound sensorineural hearing loss with the ability to perceive sound. For example, cochlear implants have an electrode assembly which is implanted in the cochlea. In operation, electrical stimuli are delivered to the auditory nerve via the electrode assembly, thereby bypassing the inoperative hair cells to cause a hearing percept.

For a variety of reasons, individuals with mild sensorineural hearing loss are typically not candidates for a cochlear implant. Rather, such individuals receive an acoustic hearing aid. Hearing aids rely on principles of air conduction to transmit acoustic signals to the cochlea. In particular, hearing aids amplify received sound and transmit the amplified sound into the ear canal. This amplified sound reaches the cochlea in the form of mechanical energy, causing motion of the perilymph and stimulation of the auditory nerve.

Unfortunately, not all individuals suffering from mild sensorineural hearing loss are able to derive suitable benefit from hearing aids. For example, some individuals are prone to chronic inflammation or infection of the ear canal. Other individuals have malformed or absent outer ear and/or ear canals resulting from a birth defect, or as a result of medical conditions such as Treacher Collins syndrome or Microtia.

For these and other individuals, another type of hearing prosthesis has been developed in recent years. This hearing prosthesis, commonly referred to as a middle ear implant, converts received sound into a mechanical force that is applied to the ossicular chain or directly to the cochlea, via an actuator implanted in or adjacent to the middle ear cavity.

SUMMARY

In an exemplary embodiment, there is a prosthesis, comprising an apparatus configured to deliver a therapeutic substance from outside a cochlea to inside the cochlea and configured to evoke a mechanically based hearing percept.

In an exemplary embodiment, there is a system, comprising a drug delivery sub-system configured to deliver drug to a cochlea of a recipient, and an energy delivery sub-system configured to evoke a hearing percept via fluid flow generation, wherein the drug delivery sub-system and the energy delivery sub-system are configured to access the cochlea at a common location.

In an exemplary embodiment, there is a method, comprising treating a cochlea for an ailment, the ailment having a deleterious effect on a recipient's hearing, the treatment being a treatment to at least one of at least partially remediate, stabilize or at least slow a hearing impairment of the recipient, wherein the recipient has at least some residual hearing, and subsequent to the action of treating the cochlea, operating a hearing device configured to mechanically stimulate the cochlea to evoke a hearing percept.

In an exemplary embodiment, there is a hydraulic hearing prosthesis configured to move a fluid into and out of a cochlea to evoke a hearing percept.

BRIEF DESCRIPTION OF THE DRAWINGS

Embodiments are described below with reference to the attached drawings, in which.

DETAILED DESCRIPTION

Figure 1:
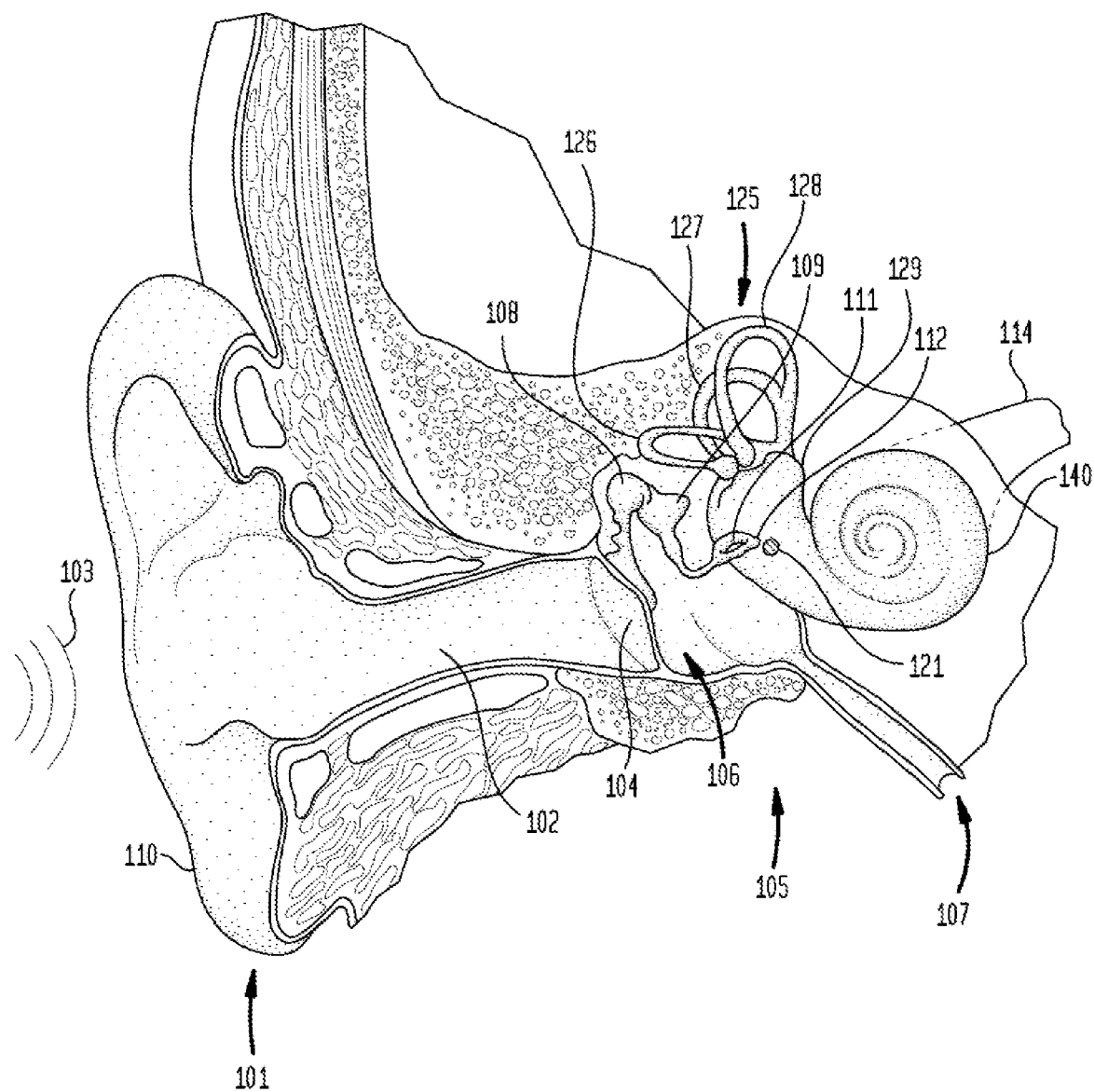
FIG. 1 is perspective view of a human ear.

FIG. 1 is a perspective view of a human skull showing the anatomy of the human ear. As shown in FIG. 1, the human ear comprises an outer ear 101, a middle ear 105, and an inner ear 107. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112, which is adjacent round window 121. This vibration is coupled through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to the vibration of tympanic membrane 104. This vibration sets up waves of fluid motion of the perilymph within cochlea 140. Such fluid motion, in turn, activates hair cells (not shown) inside cochlea 140. Activation of the hair cells causes nerve impulses to be generated and transferred through the spiral ganglion cells (not shown) and auditory nerve 114 to the brain (also not shown) where they cause a hearing percept.

As shown in FIG. 1, semicircular canals 125 are three half-circular, interconnected tubes located adjacent cochlea 140. Vestibule 129 provides fluid communication between semicircular canals 125 and cochlea 140. The three canals are the horizontal semicircular canal 126, the posterior semicircular canal 127, and the superior semicircular canal 128. The canals 126, 127, and 128 are aligned approximately orthogonally to one another. Specifically, horizontal canal 126 is aligned roughly horizontally in the head, while the superior 128 and posterior canals 127 are aligned roughly at a 45 degree angle to a vertical through the center of the individual's head.

Each canal is filled with a fluid called endolymph and contains a motion sensor with tiny hairs (not shown) whose ends are embedded in a gelatinous structure called the cupula (also not shown). As the orientation of the skull changes, the endolymph is forced into different sections of the canals. The hairs detect when the endolymph passes thereby, and a signal is then sent to the brain. Using these hair cells, horizontal canal 126 detects horizontal head movements, while the superior 128 and posterior 127 canals detect vertical head movements.

Figure 2:
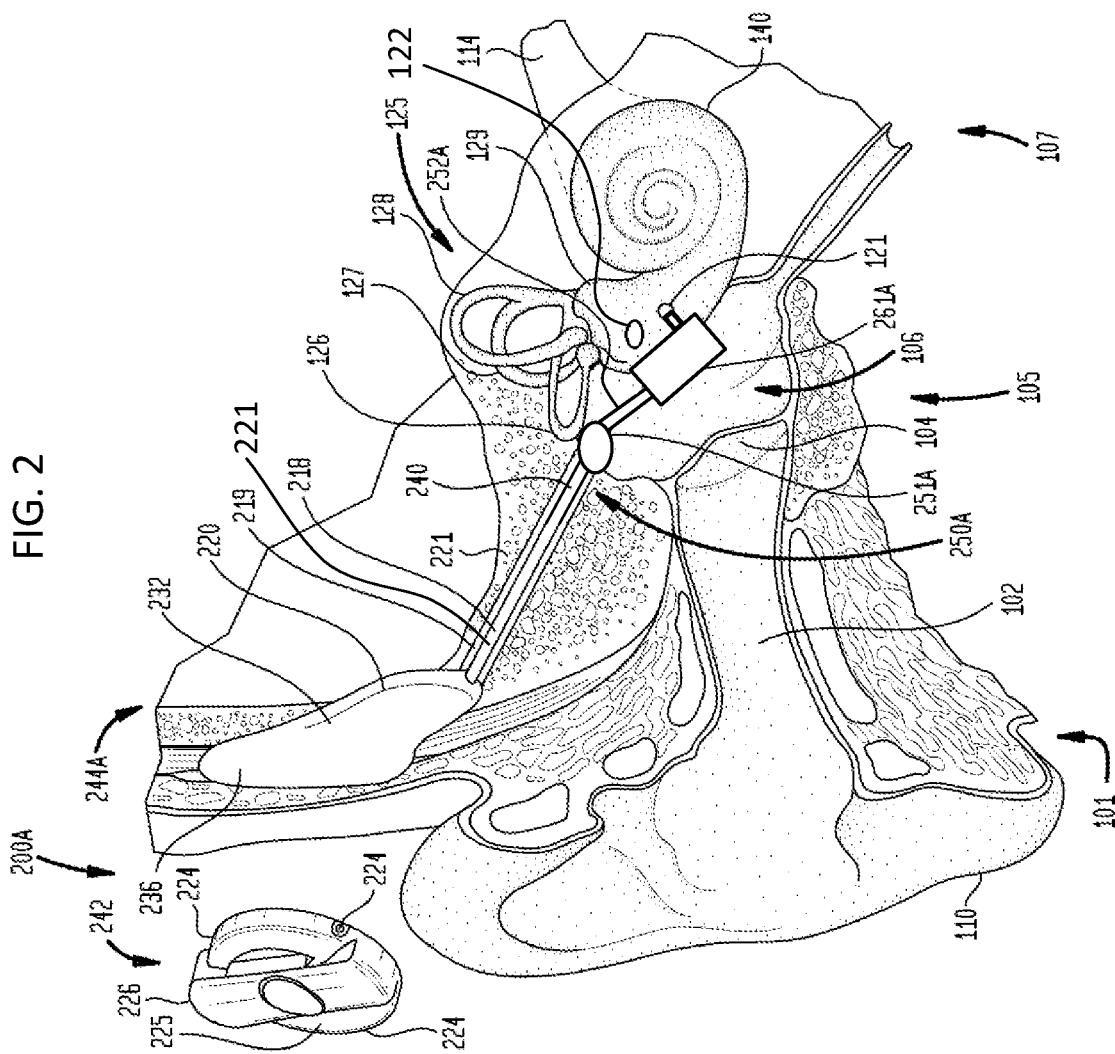
FIG. 2 is a perspective view of an exemplary cochlear stimulator implanted in accordance with an exemplary embodiment.

FIG. 2 is a perspective view of an exemplary cochlear stimulator 200A in accordance with some exemplary embodiments. Cochlear stimulator 200A comprises an external component 242 that is directly or indirectly attached to the body of the recipient, and an internal component 244A that is temporarily or permanently implanted in the recipient. External component 242 typically comprises two or more sound input elements, such as microphones 224 for detecting sound, a sound processing unit 226, a power source (not shown), and an external transmitter unit 225. External transmitter unit 225 comprises an external coil (not shown). Sound processing unit 226 processes the output of microphones 224 and generates encoded data signals which are provided to external transmitter unit 225. For ease of illustration, sound processing unit 226 is shown detached from the recipient.

Internal component 244A comprises an internal receiver unit 232, a stimulator unit 220, and a stimulation arrangement 250A in electrical communication with stimulator unit 220 via cable 218 extending thorough artificial passageway 219 in mastoid bone 221. Internal receiver unit 232 and stimulator unit 220 are hermetically sealed within a biocompatible housing, and are sometimes collectively referred to as a stimulator/receiver unit.

Internal receiver unit 232 comprises an internal coil (not shown), and optionally, a magnet (also not shown) fixed relative to the internal coil. The external coil transmits electrical signals (i.e., power and stimulation data) to the internal coil via a radio frequency (RF) link. The internal coil is typically a wire antenna coil comprised of multiple turns of electrically insulated platinum or gold wire. The electrical insulation of the internal coil is provided by a flexible silicone molding (not shown). In use, implantable receiver unit 232 is positioned in a recess of the temporal bone adjacent auricle 110.

In the illustrative embodiment of FIG. 2, ossicles 106 have been explanted, thus revealing oval window 122.

Stimulation arrangement 250A comprises both the distal and proximal portions of cable 218 (221 and 240), an actuator assembly 261A, an actuator mount member 251A, an actuator position arm 252A that extends from actuator mount member 251A and supports or at least holds actuator assembly 261A in place relative to the outside of the cochlea 140. In an exemplary embodiment, actuator mount member 251A is osseointegrated to mastoid bone 221, or more particularly, to the exit of artificial passageway 219 formed in mastoid bone 221.

In this embodiment, stimulation arrangement 250A is implanted and/or configured such that a portion of the actuator assembly interfaces with the round window 121, as can be seen, while it is noted that in an alternate embodiment, a portion of the actuator assembly interfaces with the oval window 122 (and both windows in some alternate embodiments).

As noted above, a sound signal is received by microphone(s) 224, processed by sound processing unit 226, and transmitted as encoded data signals to internal receiver 232. Based on these received signals, stimulator unit 220 generates drive signals which cause actuation of actuator assembly 261A.

Figure 3:
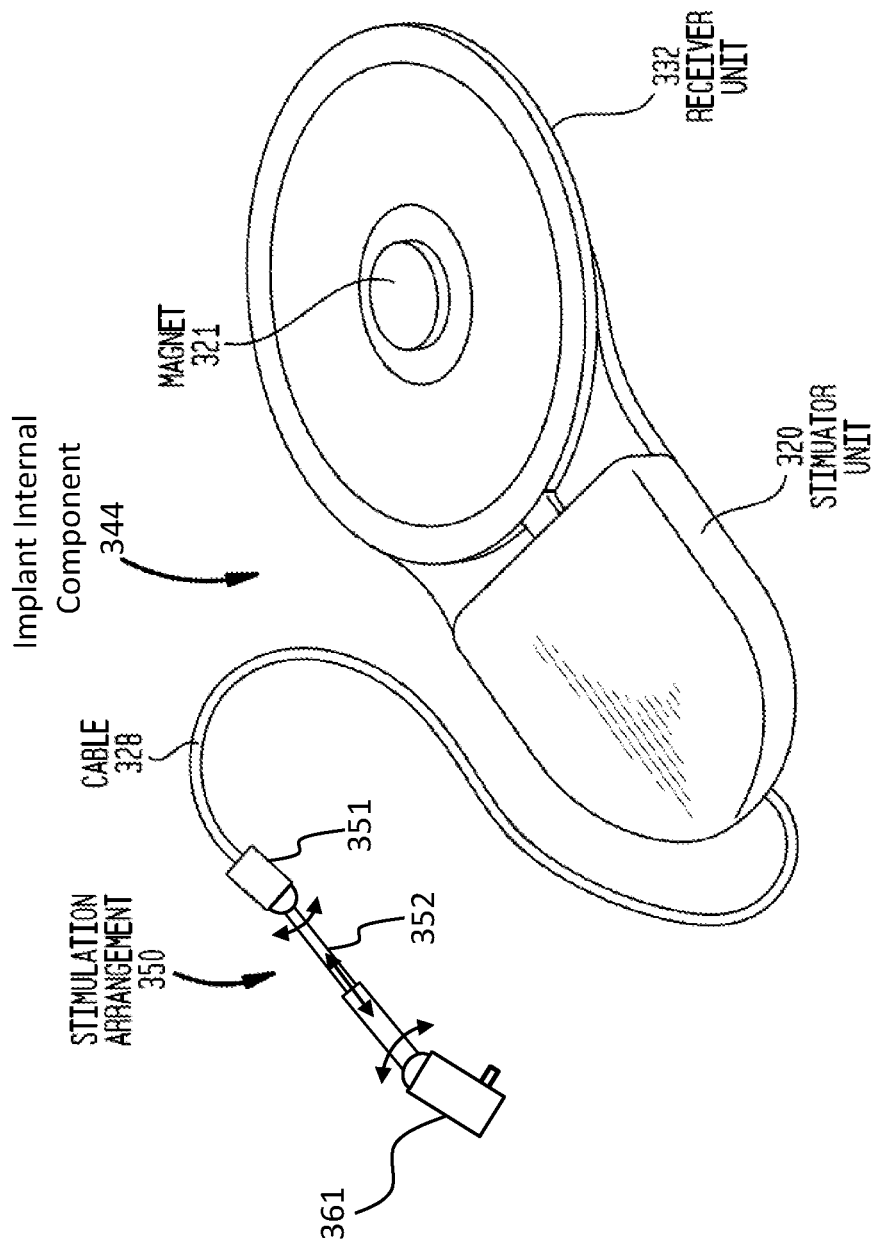
FIGS. 3 and 4 are schematics depicting exemplary implantable components.

FIG. 3 is a perspective view of an exemplary internal component 344 of an implant which generally represents internal component 244A described above. Internal component 344 comprises an internal receiver unit 332, a stimulator unit 320, and a stimulation arrangement 350. As shown, receiver unit 332 comprises an internal coil (not shown), and a magnet 321 fixed relative to the internal coil. In some embodiments, internal receiver unit 332 and stimulator unit 320 are hermetically sealed within a biocompatible housing. This housing has been omitted from FIG. 3 for ease of illustration.

Stimulator unit 320 is connected to stimulation arrangement 350 via a cable 328, corresponding to cable 218 of FIG. 2. Stimulation arrangement 350 comprises an actuator assembly 361, corresponding to actuator 261A of FIG. 2, an actuator assembly mount member 351, corresponding to actuator assembly mount member 251A of FIG. 2, and an actuator assembly positioning arm 352, corresponding to the actuator assembly positioning arm 352 of FIG. 2. In an exemplary embodiment, actuator assembly mount member 351 is configured to be located in the artificial passageway 219 or adjacent thereto and fixed to the mastoid bone of the recipient. As indicated by the curved arrows of FIG. 3, the actuator assembly mount member 351 and the actuator assembly 361 are configured to enable articulation of the actuator assembly positioning arm 352 relative to those components. Further, as indicated by the straight arrow of FIG. 3, the actuation assembly positioning arm 352 is configured to telescope to provide longitudinal adjustment between the actuator assembly 361 and the actuator assembly mount member 251.

Figure 4:
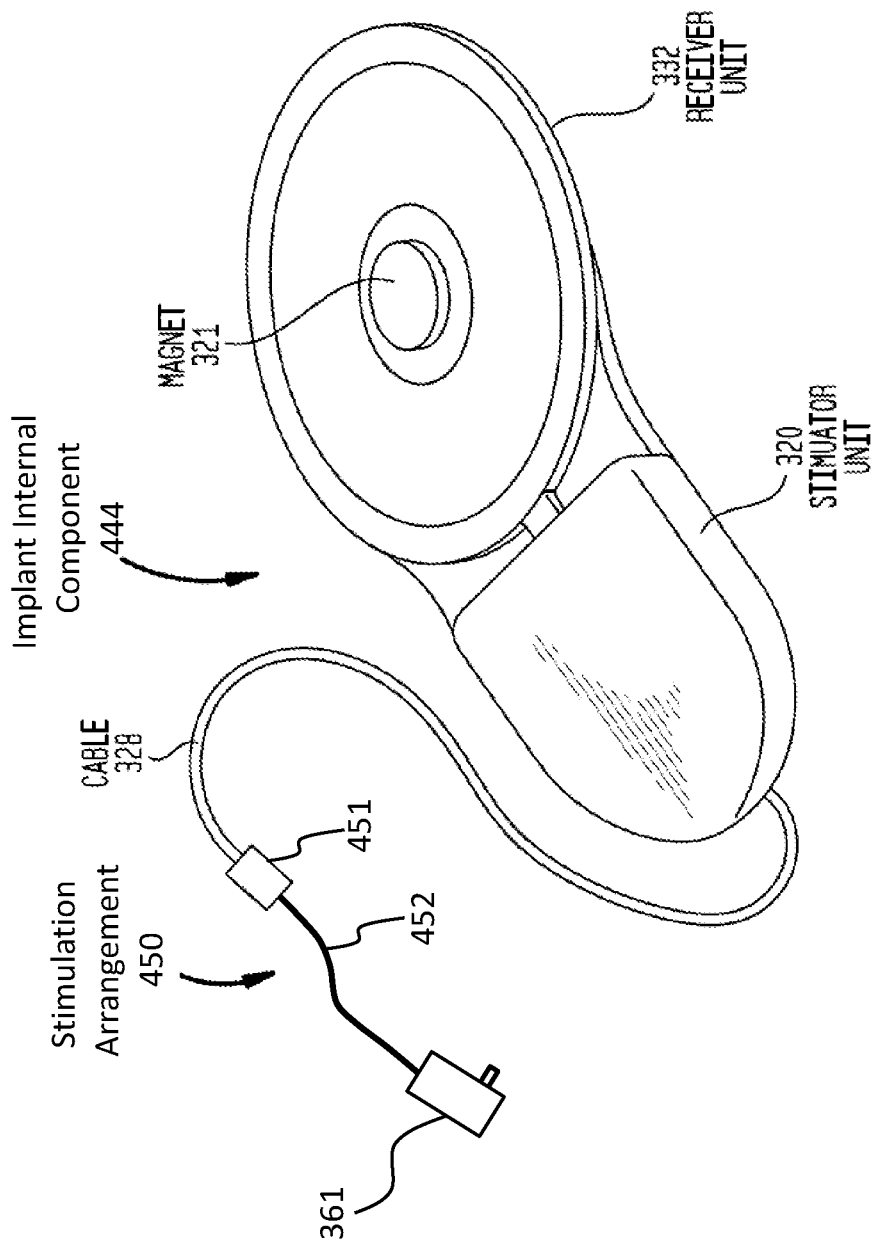

FIG. 4 is a perspective view of an exemplary internal component 444 of an implant which generally represents internal component 244A described above. Internal component 444 comprises like components corresponding to those of internal component 344.

As with internal component 344, internal component 444 is such that stimulator unit 320 is connected to stimulation arrangement 450 via a cable 328, corresponding to cable 218 of FIG. 2. However, element 451 is a coupling that instead of coupling to the articulation device detailed above in the embodiment of FIG. 3, couples to cable 452 which is coupled to actuator assembly 361. This embodiment provides a less complicated arrangement which can have utilitarian value where the surgeon or the like is going to hand connect actuator assembly 361 directly to the exterior of the cochlea and where actuator assembly 361 will remain in place relative to the cochlea for a given period of time. The cable 452 is flexible so as to permit relative ease of movement of the actuator assembly 361 during the implantation process. The coupling 451 enables the stimulation arrangement 350 to be replaced without removing the stimulator unit 320 and/or enables the stimulator unit 320 to be removed and replaced without removing the stimulation arrangement 450.

Some exemplary embodiments of the teachings detailed herein enable drug delivery to the cochlea or otherwise the delivery of a utilitarian substance to the cochlea.

Figure 5:
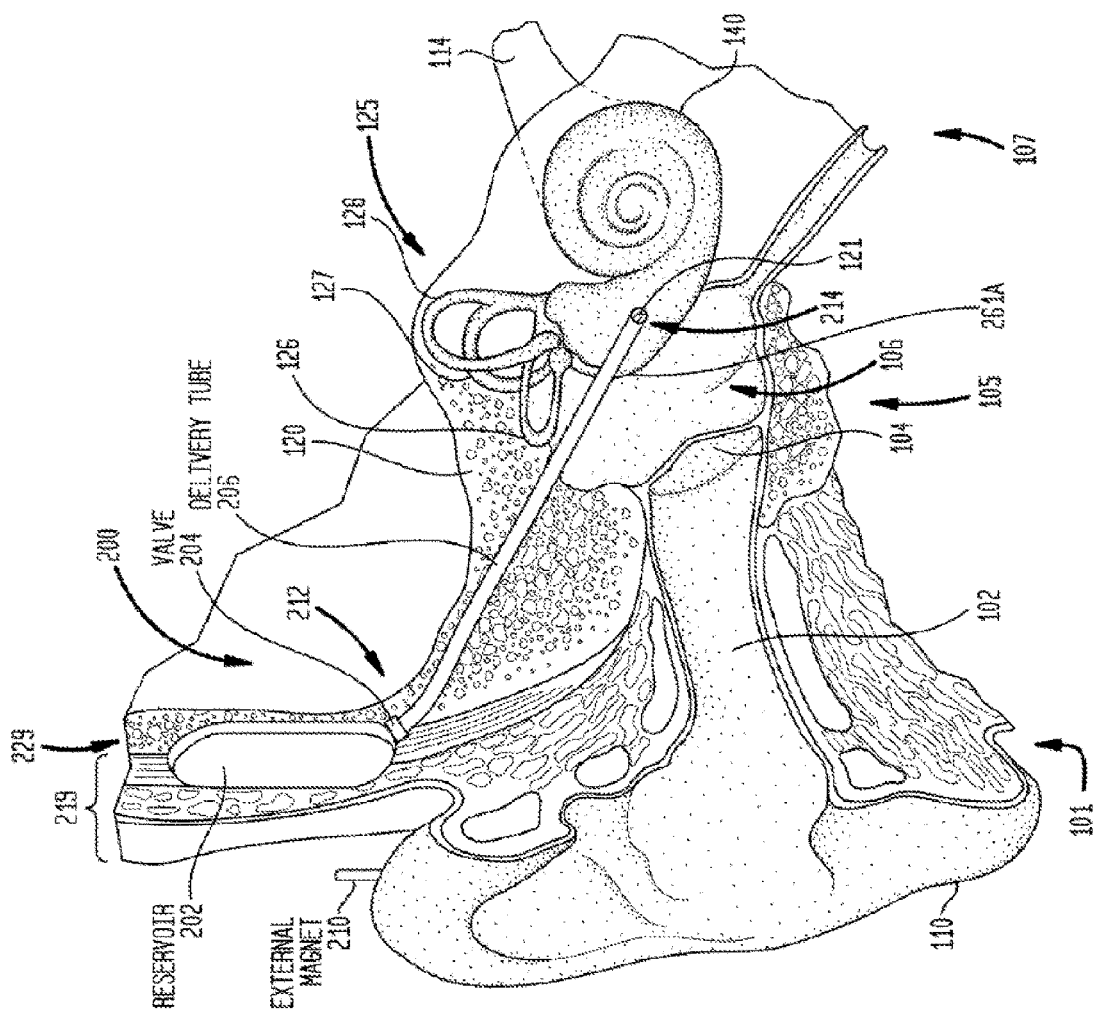
FIG. 5 is a schematic depicting an exemplary therapeutic substance delivery system.

FIG. 5 depicts an exemplary drug delivery device, the details of which will be provided below. It can be utilitarian to have a prompt and/or extended delivery solution for use in the delivery of treatment substances to a target location of a recipient. In general, extended treatment substance delivery refers to the delivery of treatment substances over a period of time (e.g., continuously, periodically, etc.). The extended delivery may be activated during or after surgery and can be extended as long as is needed. The period of time may not immediately follow the initial implantation of the auditory prosthesis. Embodiments of the teachings herein can facilitate extended delivery of treatment substances, as well as facilitating prompt delivery of such substances.

FIG. 5 illustrates an implantable delivery system 200 having a passive actuation mechanism, which can be modified as will be detailed below in some embodiments. However, it is noted that the delivery system 200 can also or instead have an active actuation system, again which can be modified as will be detailed below. The delivery system 200 is sometimes referred to herein as an inner ear delivery system because it is configured to deliver treatment substances to the recipient's inner ear (e.g., the target location is the interior of the recipient's cochlea 140). It is also noted that in some implementations of a modified arrangement of FIG. 5, as will be described below, the passive actuation mechanism enables movement of therapeutic substance to another device that in turn has an active actuation mechanism (e.g., element 361 of FIG. 6A, additional details of which are described below), where the latter is used to actually transport the therapeutic substance into a cochlea (the former is used to get the substances to the latter).

Delivery system 200 of FIG. 5 comprises a reservoir 202, a valve 204, and a delivery tube 206, in addition to some additional components, as will be described below. For ease of illustration, the delivery system 200 is shown separate from any implantable auditory prostheses. Additionally, the delivery system 200 can include, or operate with, an external magnet 210, which is separate from or part of the implantable auditory prostheses, for purposes of, e.g., controlling operation of valve 204.

Figure 27:
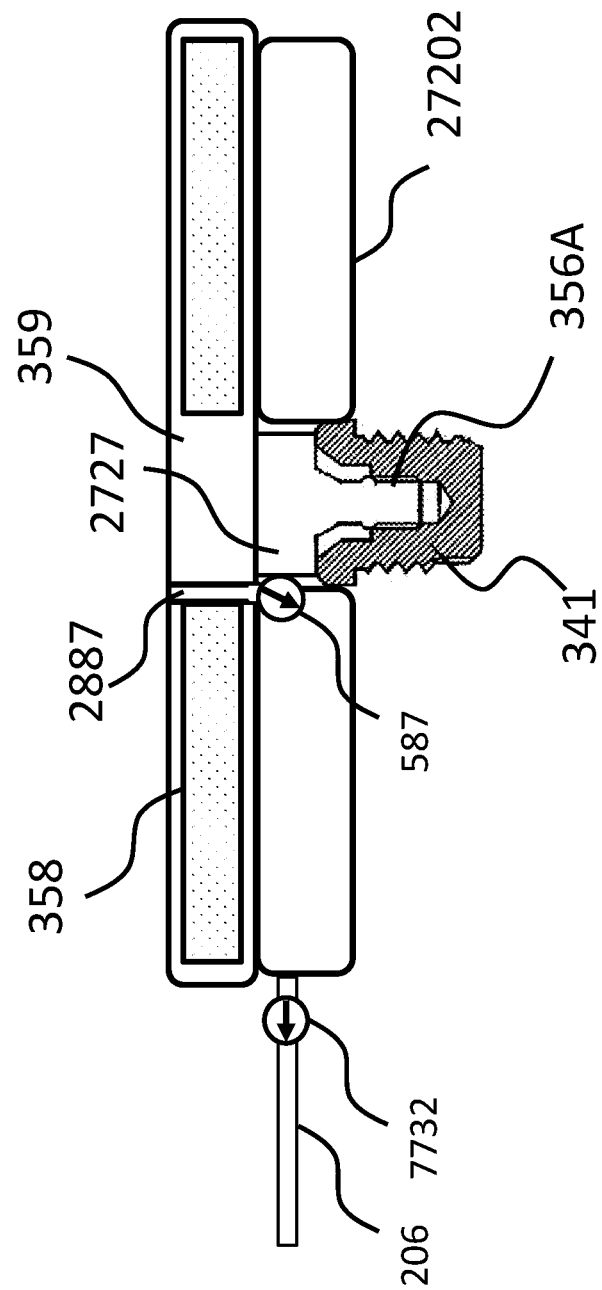

The delivery system 200, and any of the other delivery systems detailed herein and/or variations thereof, can be used with, for example, the hearing prosthesis of figures included herein, and also variations thereof, as will be detailed below by way of example and not by way of limitation. For instance, the arrangement of FIG. 5 can be used with an external removable component (sometimes referred to in the art as a sound processor) of a passive transcutaneous bone conduction device. Briefly, FIG. 27 provides an exemplary embodiment of a modified version of FIG. 5 utilized with a passive transcutaneous bone conduction device. In such embodiments, the implantable components (e.g., reservoir, valve, delivery tube, etc.) of delivery system 200 (or any other delivery system detailed herein) can be integrated with at least one other component of the implantable auditory prosthesis. That said, in some examples, the arrangement of FIG. 5 can be utilized with a removable component of a passive transcutaneous bone conduction device that is not magnetically coupled to the recipient but instead is held against the head of the recipient via a mechanical device such as a soft band or an arch.

In the arrangement of FIG. 5, the reservoir 202 is positioned within the recipient underneath a portion of the recipient's skin/muscle/fat, collectively referred to herein as tissue 219. The reservoir 202 may be positioned between layers of the recipient's tissue 219 or may be adjacent to a subcutaneous outer surface 229 of the recipient's skull. For example, the reservoir 202 may be positioned in a surgically created pocket at the outer surface 229 (i.e., adjacent to a superior portion 118 of the temporal bone 115).

The reservoir 202 is, prior to or after implantation, at least partially filled with a treatment substance for delivery to the inner ear 107 of the recipient. The treatment substance may be, for example, in a liquid form, a gel form, and/or comprise nanoparticles or pellets. In certain arrangements, the treatment substance may initially be in a crystalline/solid form that is subsequently dissolved. For example, a reservoir could include two chambers, one that comprises a fluid (e.g., artificial perilymph or saline) and one that comprises the crystalline/solid treatment substance. The fluid may be mixed with the crystalline/solid treatment substance to form a fluid or gel treatment substance that may be subsequently delivered to the recipient.

The reservoir 202 can include a needle port (not shown) so that the reservoir 202 can be refilled via a needle injection through the skin. In some implementations of FIG. 5, the reservoir 202 may be explanted and replaced with another reservoir that is, prior to or after implantation, at least partially filled with a treatment substance. The reservoir 202 may have a preformed shape and the reservoir is implanted in this shape. The reservoir 202 may have a first shape that facilitates implantation and a second shape for use in delivering treatment substances to the recipient. For example, the reservoir 202 may have a rolled or substantially flat initial shape that facilitates implantation. The reservoir 202 may then be configured to expand after implantation. Reservoir 202 may have other shapes as needed to operate with hearing prostheses, as will be detailed below by way of example and not by way of limitation.

Figure 7:
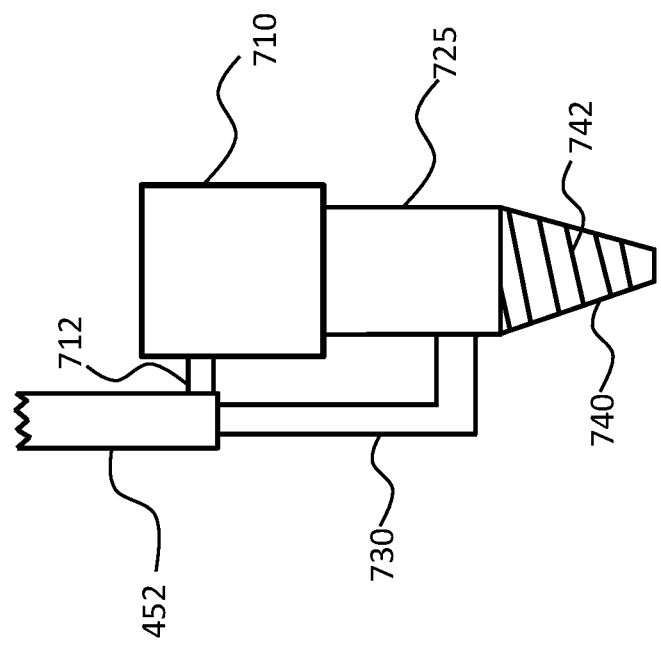
FIGS. 7-9 are schematics depicting an exemplary embodiment.

The delivery tube 206 includes a proximal end 212 and a distal end 214. The proximal end 212 of the delivery tube 206 is fluidically coupled to the reservoir 202 via the valve 204. As shown in FIG. 7, the distal end 214 of the delivery tube 206 is fluidically coupled, directly or indirectly (with respect to the latter, such as via the actuator assembly 361, additional details of which will be presented below), to the cochlea via the recipient's round window 121.

FIG. 5, as shown, utilizes a passive actuation mechanism to produce a pumping action to transfer a treatment substance from the reservoir 202 to the distal end 214 of the delivery tube 206, but again, some embodiments are modified versions of FIG. 5 that utilize active actuation. The reservoir 202 is compressible in response to an external force. That is, at least one part or portion of the reservoir 202, such as wall 220 or a portion thereof, is formed from a resiliently flexible material that is configured to deform in response to application of the external force. In certain modified embodiments, the positioning of the reservoir 202 adjacent the superior portion of the mastoid provides a surface sufficiently rigid to counter the external force. As a result, a pressure change occurs in the reservoir 202 so as to propel (push) a portion of the treatment substance out of the reservoir through valve 204.

FIG. 5 illustrates a specific arrangement in which the reservoir 202 includes a resiliently flexible wall 220. It is to be appreciated that the reservoir 202 can be formed from various resiliently flexible parts and rigid parts. It is also to be appreciated that the reservoir 202 may have a variety of shapes and sizes (e.g., cylindrical, square, rectangular, etc.) or other configurations. For example, the reservoir 202 could further include a spring mounted base that maintains a pressure in the reservoir 202 until the reservoir is substantially empty. Other mechanisms for maintaining a pressure in the reservoir may be used in other arrangements.

In some implementations of FIG. 5, external force is applied on the tissue 219 adjacent to the reservoir 202 to create the external force. As will be described below, in some embodiments, an external vibratory device of a passive transcutaneous bone conduction device that vibrates to evoke a hearing percept is pressed onto the soft tissue 219 under which the reservoir 202 is located. The movement (e.g., oscillation/vibration) of the actuator causes deformations the reservoir 202 to create the pumping action that propels the treatment substance out of the reservoir.

Internal and/or external magnets and/or magnetic materials may be used in the arrangements of FIG. 5 to ensure that the actuator applies force at an optimal location of the reservoir 202. For example, the reservoir 202 may include a magnetic positioning member located at or near an optimal location for application of an external force from the actuator. The actuator may include a magnet configured to magnetically mate with the magnetic positioning member. As such, when the actuator is utilitarianly positioned, the magnet will mate with the magnetic positioning member and the force from the actuator will be applied at the optimal location. FIG. 27 depicts an assembly that includes a magnet having utilitarian value that will be detailed below.

A remote control, remotely placed actuator (subcutaneous or otherwise) can be used. For example, in a further arrangement, the implant includes implanted electronics. These implanted electronics may be configured to, for example, control the valve 204 and/or include an actuation mechanism that can force treatment substance from the reservoir 202. The implanted electronics may be powered and/or controlled through a transcutaneous link (e.g., RF link). As such, the implanted electronics may include or be electrically connected to an RF coil, receiver/transceiver unit, etc.

The implanted electronics may include or be connected to a sensor that is used, at least in part, to assist in control of delivery of the treatment substance to the recipient. For example, a sensor (e.g., a temperature sensor, a sensor to detect infection or bacteria growth, etc.) may provide indications of when a treatment substance should be delivered and/or when delivery should be ceased for a period of time. A sensor may also be configured to determine an impact of the treatment substance on the recipient (e.g., evaluate effectiveness of the treatment substance).

As noted, the treatment substance (sometimes herein referred to as therapeutic substance) is released from the reservoir 202 through the valve 204. The valve 204 may be a check valve (one-way valve) that allows the treatment substance to pass therethrough in one direction only. This assures that released treatment substances do not back-flow into the reservoir 202. The valve 204 can be a valve that is configured to open in response to the pressure change in the reservoir 202 (e.g., a ball check valve, diaphragm check valve, swing check valve or tilting disc check valve, etc.). The valve 204 may be a stop-check valve that includes an override control to stop flow regardless of flow direction or pressure. That is, in addition to closing in response to backflow or insufficient forward pressure (as in a normal check valve), a stop-check value can also be deliberately opened or shut by an external mechanism, thereby preventing any flow regardless of forward pressure. The valve 204 may be a stop-check value that is controlled by an external electric or magnetic field generated by, for example, the external magnet, an electromagnet, etc. The valve of FIG. 5 can be responsive to a magnetic field generated by external magnet. As such, the valve 204 will open when the external magnet is positioned in proximity to the valve 204 and will close when the external magnet is removed from the proximity of the valve 204. In some implementations of FIG. 5, variable magnet strengths of external magnets may be used to control the dosage of the treatment substance. Additionally, an electromagnet may be used in place of the external magnet.

The use of a stop-check valve can prevent unintended dosing of the treatment substance when, for example, an accidental external force acts on the reservoir 202. The reservoir 202 is formed such that an increase in pressure of the reservoir 202 without an accompanying treatment substance release will not damage (i.e., rupture) the reservoir.

Other types of valves may be used in other implementations of the device of FIG. 5. For example, the valve 204 may be actuated (i.e., opened) in response to an electrical signal (e.g., piezoelectric valve). The electrical signal may be received from a portion of an auditory prosthesis (not shown) that is implanted with the delivery system 200 or the electrical signal may be received from an external device (e.g., an RF actuation signal received from an external sound processor, remote control, etc.).

It is also noted that while the valve 204 is depicted as being present on the proximal end of the tube 206, the valve can be located on the distal end of the tube 206. Alternatively, the valve can be located in the middle of the delivery tube 206. Alternatively, the valves can be located at various locations (i.e., a plurality of valves can be utilized, such as one of the distal end, one of the proximal end, and/or one in between).

Once the treatment substance is released through valve 204, the treatment substance flows through the delivery tube 206 to the cochlea, either directly, or indirectly via the actuator assembly 361/461. In embodiments utilizing the actuator assembly, the actuator assembly corresponds to a transfer mechanism to transfer the treatment substance from the delivery tube 206 into the cochlea 140 via the round window 121 (or oval window, or another orifice such as that established by a cochleostomy into the cochlea).

The reservoir 202 may include a notification mechanism that transmits a signal or notification indicating that the reservoir 202 is substantially empty and/or needs refilled. For example, one or more electrode contacts (not shown) may be present and become electrically connected when the reservoir is substantially empty. Electronic components associated with or connected to the reservoir 202 may accordingly transmit a signal indicating that reservoir needs filled or replaced.

FIG. 5 illustrates a specific example in which the round window 121 is the target location. As noted above, the round window 121 is an exemplary target location and other target locations are possible. Again, the oval window can be utilized to access the cochlea alternatively and/or in addition to the round window, and/or a cochleostomy can be utilized to access the cochlea in addition to one or both of the round and oval window). FIG. 5 also illustrates an arrangement in which the reservoir 202 is positioned adjacent to the outer surface 229 of the recipient's skull so that an external force may be used to propel the treatment substance from the reservoir.

Figure 6A:
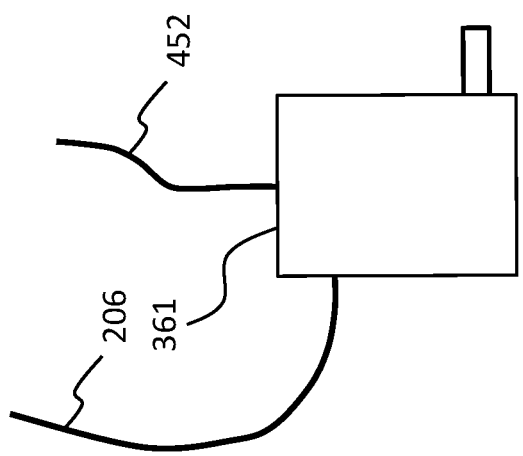
FIGS. 6A-6D are schematics depicting exemplary working ends of an embodiment that combines the embodiments of FIGS. 3 to 5.
Figure 6B:
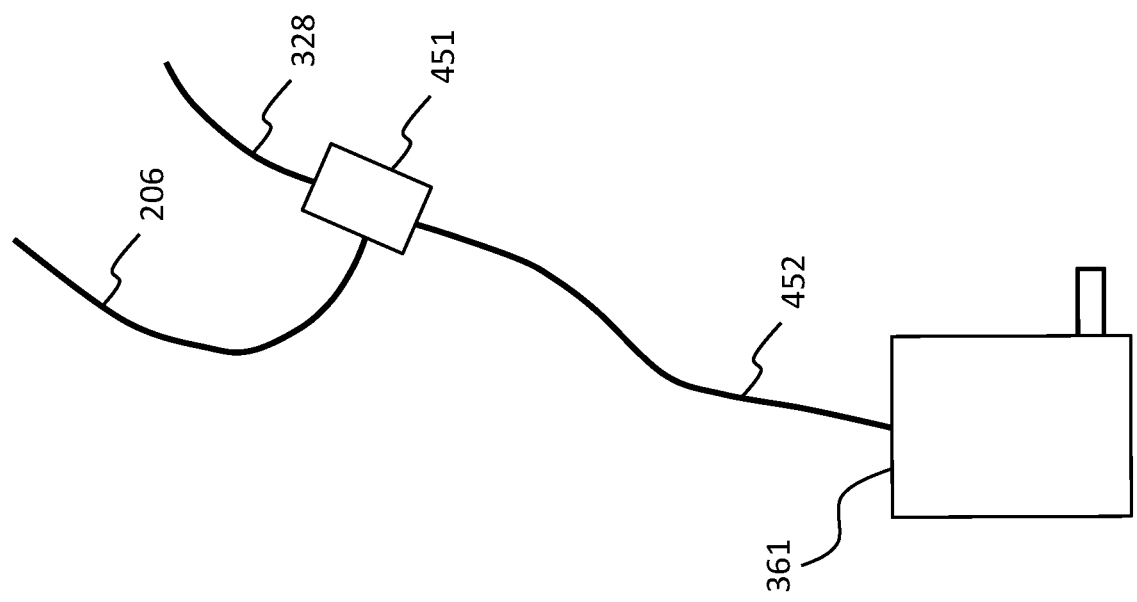

As noted herein, the therapeutic delivery system of FIG. 5 can be combined with a partially or fully implanted device configured to evoke a hearing percept. By way of example only and not by way of limitation, the therapeutic delivery system of FIG. 5 can be combined with the hearing prosthesis of FIG. 3 and FIG. 4. Briefly, in an exemplary embodiment, the actuator assembly 361 can be configured so as to receive or otherwise connect to the distal end of tube 206 of the therapeutic delivery system. In an exemplary embodiment of such as depicted in FIG. 6A, where the embodiment of FIG. 4 is presented by way of example, it is to be understood that the embodiment of FIG. 6A is also applicable to the embodiment of FIG. 3. In an alternative exemplary embodiment, the coupling 451 can be configured to receive or otherwise connect to the distal end of tube 206 of the therapeutic delivery system, as seen in FIG. 6B. Here, element 452 can serve a dual purpose of placing the actuator assembly 361 into electrical communication with the stimulator unit 320 as well as providing the therapeutic substance from tube 206 to the actuator assembly 361 ultimate delivery into the cochlea 140. Again, while the embodiment of FIG. 4 is utilized as the base design here, it is to be understood that the articulating unit of FIG. 3 can be modified so as to receive or otherwise connect to the tube 206, and provide for the transport of the therapeutic substance to the actuator via the telescopic tube, etc.

Figure 6C:
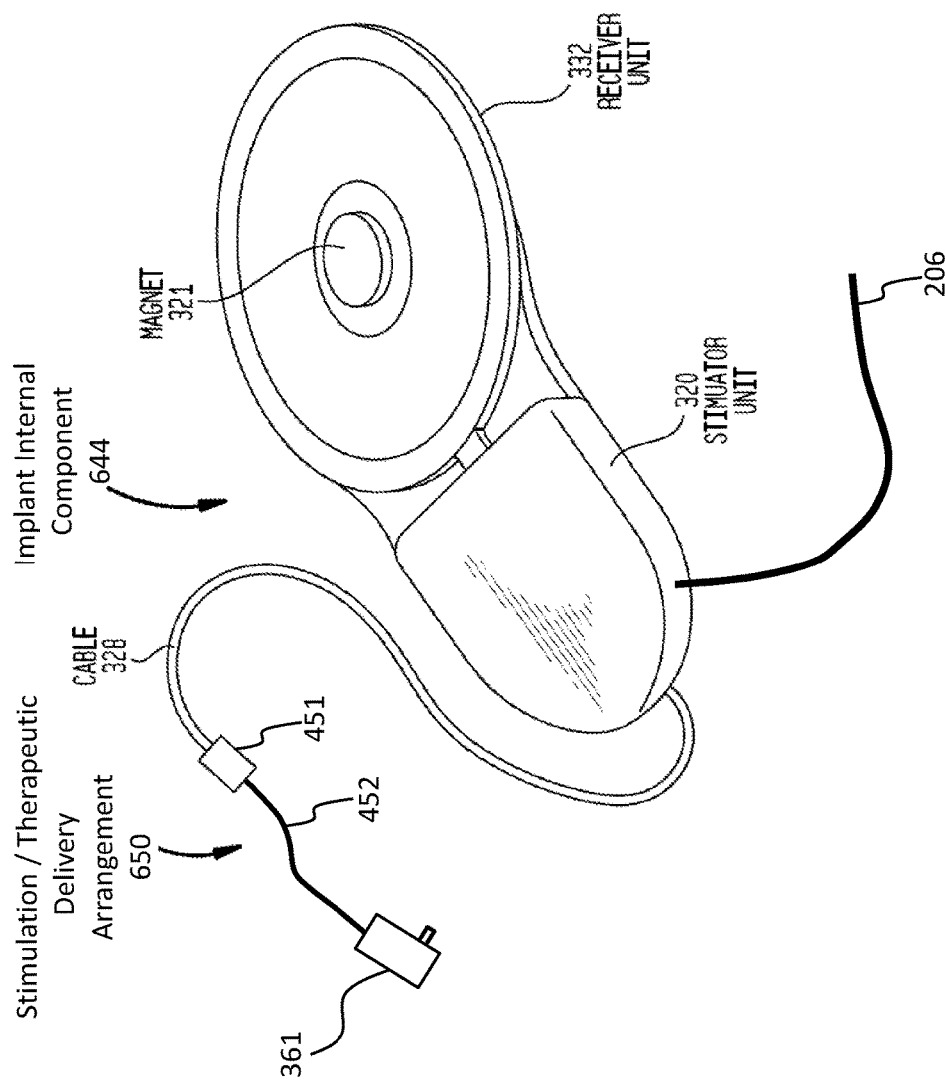
Figure 6D:
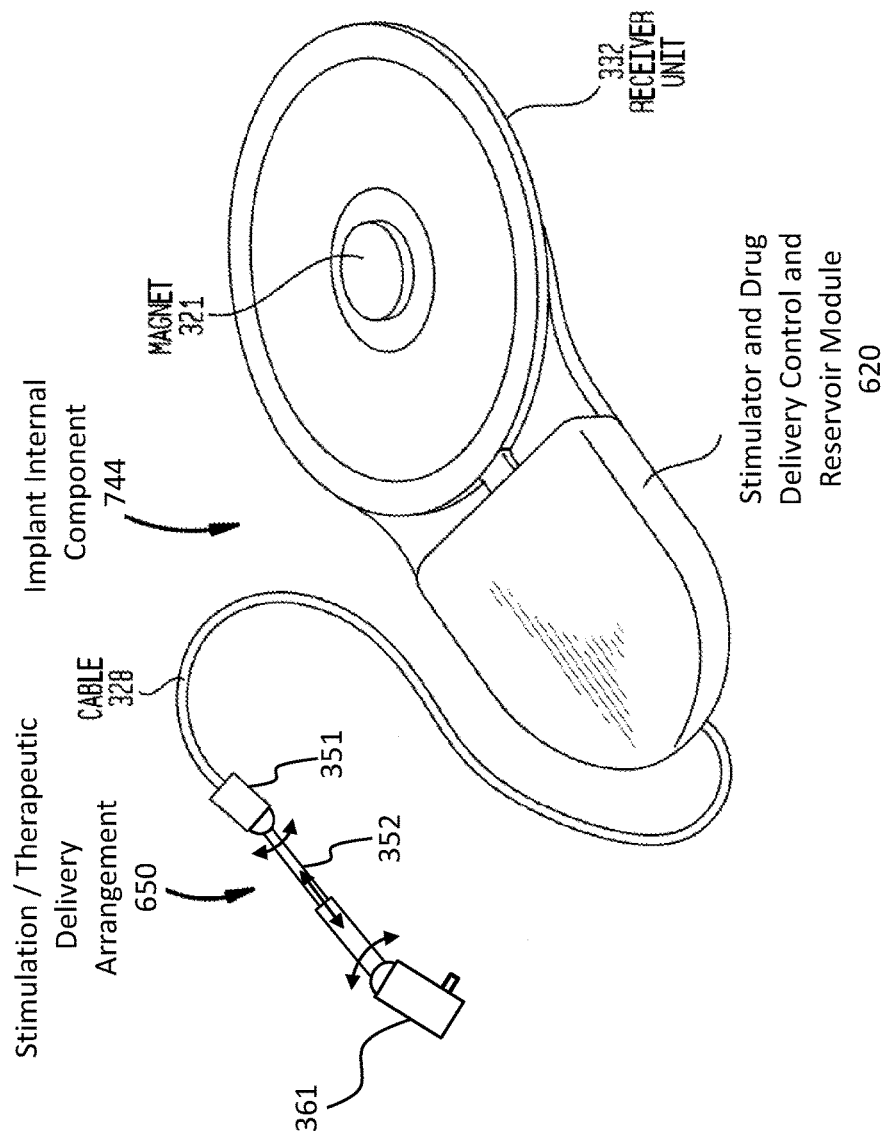

FIG. 6C depicts an exemplary embodiment where the tube 206 interfaces directly with a stimulator unit 320, and the stimulator unit 320, the cable 328, and other components are configured to enable the transport of the therapeutic substance. FIG. 6C thus depicts the implant internal component 644 seen in that figure, along with the stimulation/therapeutic delivery arrangement 650 that provides both the stimulation to the cochlea to evoke a hearing percept as well as the therapeutic substance. Again, while the embodiment of FIG. 4 has been relied upon as the base design, this concept is also applicable to the embodiment of FIG. 3. Note also that as detailed above, some exemplary embodiments can be integrated systems. In this regard, FIG. 6D presents an implant internal component 744 that is a combination of the embodiments of FIG. 3 detailed above and the embodiment of FIG. 5, where there is a unified stimulator and drug delivery control and reservoir module 620. Consistent with the teachings above, while the embodiment of FIG. 6D focuses on the embodiment of FIG. 3 as the base design, in an alternate embodiment, the embodiment of FIG. 4 can be the base design. Any combination or any arrangement of any components that can have utilitarian value and otherwise enable the teachings detailed herein can be utilized in at least some exemplary embodiments.

Some additional details of some exemplary embodiments will now be described. For ease of explanation, the embodiment of FIG. 6B will be the baseline, where the tube 206 of therapeutic delivery system is connected to the connector upstream of the actuator 361, and element 452 serves the dual purpose of providing electrical signals to the actuator 361 to power or otherwise actuate the actuator and of providing the therapeutic substance to the actuator's that the therapeutic substance may be introduced into the cochlea. However, it is to be clear that these teachings can be combined or otherwise modified into the other embodiments detailed above and/or variations thereof.

Very briefly, as noted in the previous paragraph, element 452 provides for an electrical lead assembly. That said, in some embodiments, a fluid system can be utilized to actuate the actuator. That is, instead of an electrode mechanical device being utilized to actuate the actuator 361 in the actuator 361, element 452 is utilized to conduct fluid which is utilized to cause the actuator 361 to actuate. Granted, in some embodiments, an electromechanical device is present, such as in connector 451, to impart movement on the fluid and thus actuate the actuator 361. However, this device is remote from actuator 361.

FIG. 7 depicts an exemplary actuator assembly that can correspond to any of the actuator assemblies 361 detailed above. Actuator assembly includes an electromechanical device 710 represented in black box format, which can be housed in a housing (also represented in black box format). The electromechanical device can be an EM transducer, a piezoelectric transducer, or any other type of transducer that can have utilitarian value and otherwise enable the teachings detailed herein. The electromechanical device 710 is connected to a cylinder 725 (where that term is a functional term analogous to, for example, a cylinder of a steam engine or the like—element 725 need not have a circular cross-section—any cross-section that can have utilitarian value, such as a square cross-section, can be utilized in at least some exemplary embodiments). Cylinder 725 can be a metallic based (e.g., titanium) or a plastic based cylinder having a length, depth, and a circular diameter inside, which cylinder receives a piston (more on this below). Cylinder 725 is connected to the cochlea interface component 740, which can be a hollow cone with threads 742 about the outer surface thereof as shown. Cochlea interface component 740 is configured to be screwed into the round window, the oval window, or a cochleostomy. As will be described below, in some alternate embodiments, instead of a cochlea interface component 740, the actuator assembly can instead include a component that is configured to connect to a coupling that is implanted in the cochlea (e.g., a bayonet coupling or a quarter turn coupling can be utilized).

Element 452 can be, in some embodiments, a flexible tube that contains electrical leads to provide electrical signals to the transducer of the actuator as well as one or more tubes 206 to transport the therapeutic substance. Conversely, element 452 can be one or more electrical leads that are coupled to one or more tubes 206 via, for example, one or more bands that extends about the longitudinal axes thereof. That said, element 452 can be one or more electrical leads that are relatively free to move relative to one or more tubes 206 as well as relative to one another, and are only secured relative to one another at the coupling 451 and at the actuator.

FIG. 7 depicts element 712 extending from element 452. Here, element 712 can be one or more electrical leads that branches off from element 452. Element 712 can be a tube through which one or more electrical leads extends to reach the actuator.

Now focusing on the therapeutic delivery portion of the actuator, FIG. 7 depicts element 730, which can be a tube that extends from element 452, as can be seen, which tube (can be flexible or rigid) places the cylinder 725 into fluid communication with element 452 (albeit there could be a valve interposed in between element 452 and cylinder 725, as will be described in greater detail below, but such still results in fluid communication, albeit controllable fluid communication, between the two components. In an exemplary embodiment, tube 730 enables the therapeutic substance to be delivered to the cylinder 725.

Figure 8:
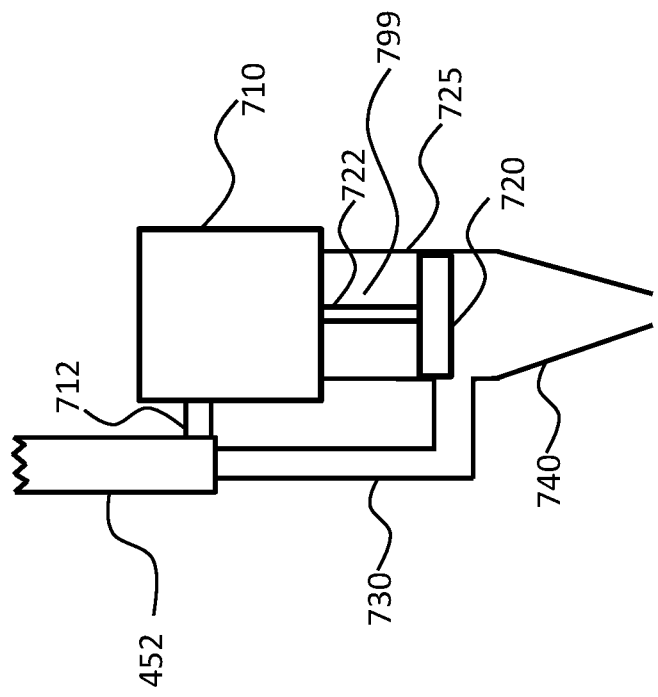
Figure 9:
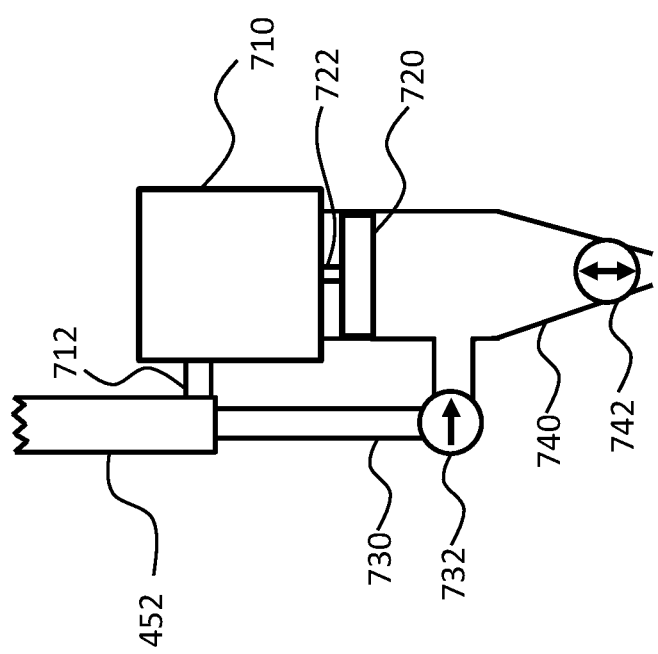

FIG. 8 depicts a cross-sectional view of some of the components of the actuator assembly, which components provide an exemplary means for delivering a therapeutic substance. As can be seen, piston 720 is connected to a piston rod at 722, which is connected to the electromechanical device 710. The electromechanical device 710 is configured to cause the piston 720 via the piston rod 722 to reciprocate upward and downward, as can be seen by comparing FIG. 8 to FIG. 9. FIG. 9 presents valves 731 and 742. These valves can be controlled and/or can be dumb valves or a combination of the two. Either way, the valve 742 enables control of fluid flow into and/or out of the cochlea, and the valve 732 enables control of therapeutic substance flow into the chamber 799 established by the cylinder (which is also established by the cone). The idea is that in some instances, the actuator assembly can be utilized to flow fluid into and/or out of the cochlea to evoke a hearing percept. By way of example only and not by way of limitation, the flow of fluid into and/or out of the cochlea results in waves of fluid motion in the cochlea that stimulate the hair therein to evoke a hearing percept. That is, waves of fluid motion of the perilymph or other substance in the cochlea (in an exemplary embodiment, the perilymph can be replaced or otherwise combined with another fluid that is biologically acceptable to the recipient), thereby activating the hair cells of the organ of Corti. Activation of the hair cells causes nerve impulses to be generated and transferred through the spiral ganglion cells and auditory nerve 114, thus resulting in a hearing percept. By coordinating the movement of the piston 720 (e.g., by coordinating movement of the transducer) with received sounds/captured sound captured by the microphone of the hearing prostheses (e.g., by processing output signals from microphones into control signals or otherwise signals to control the transducer to thus move the piston 720, with, in some embodiments, some sound processing techniques executed there between), the hearing percept that is evoked can correspond to the sound captured by the microphones.

Figure 10:
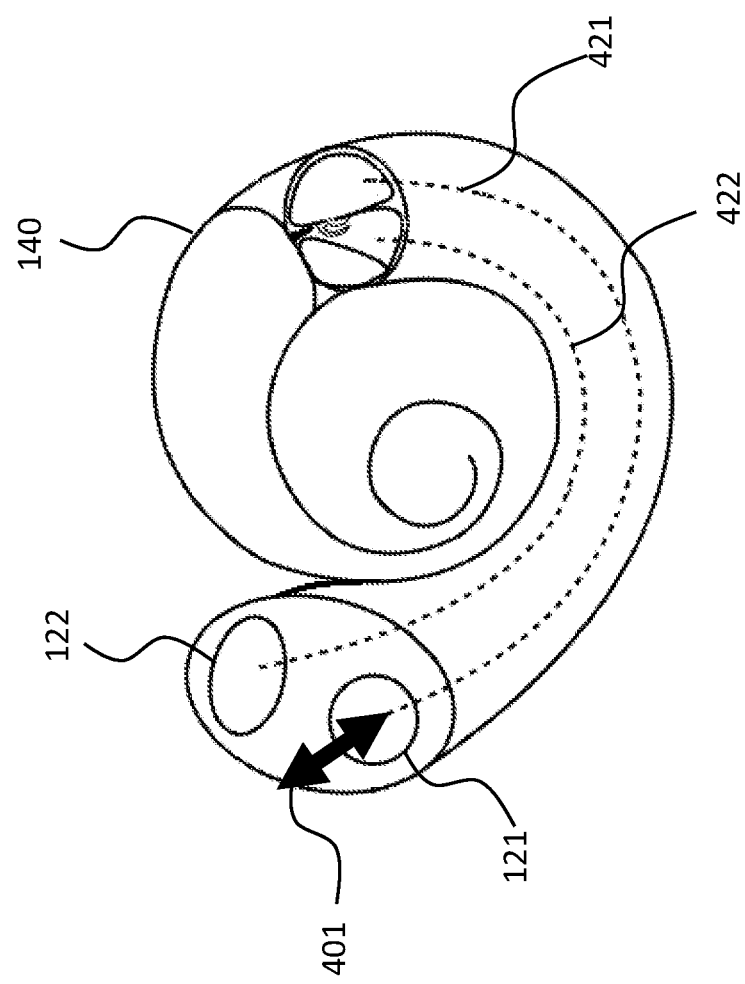
FIGS. 10-13 depict conceptual schematics representing operation of an embodiment.
Figure 11:
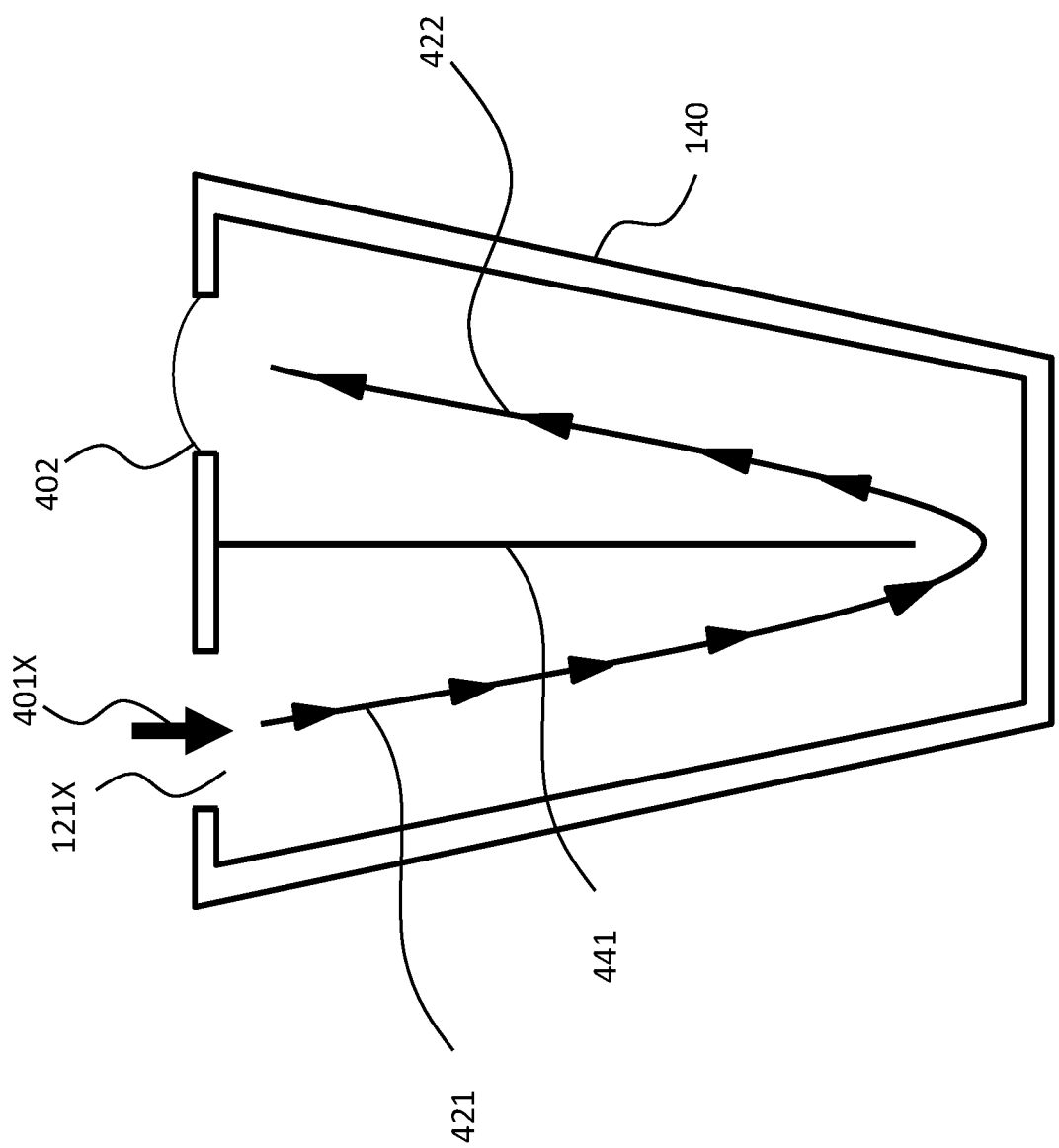
Figure 12:
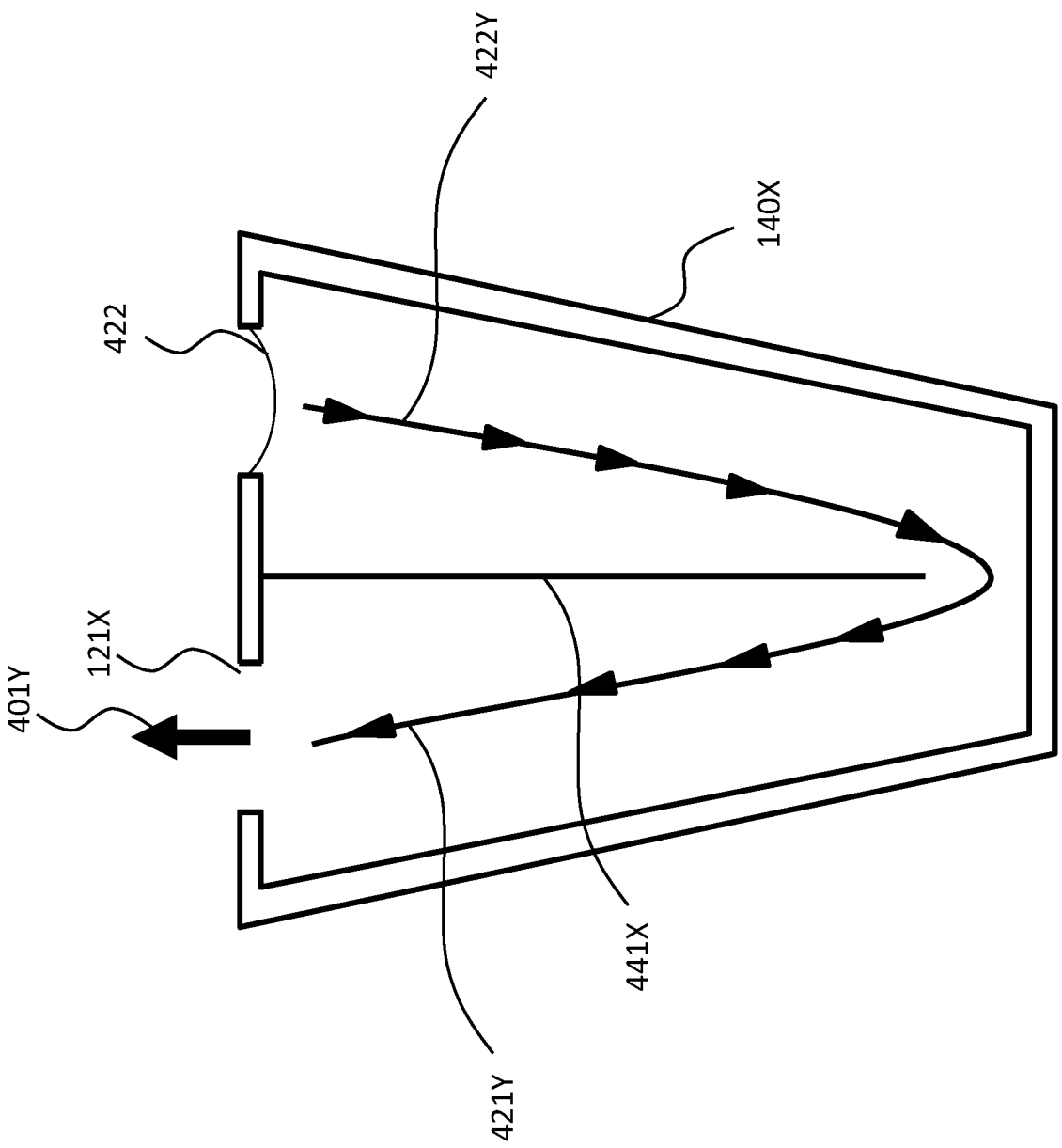

FIGS. 10, 11, and 12, depict high-level conceptual views of this concept, where actuator assembly 361 is positioned outside cochlea 140. In this exemplary embodiment, the actuator assembly 361 is configured to flow fluid into and out of the cochlea in an alternating manner (because the actuator is outside the cochlea, it pushes the fluid into the cochlea and then sucks the fluid out, as opposed to an embodiment where the actuator is in the cochlea, in which case such is reversed). Arrow 401 represents the reciprocating movement of the fluid into and then out of the cochlea. With respect to FIG. 11, in a first portion of a phase of actuation, the actuator forces fluid away from the round window 121X (X because a portion of the membrane, if not all, is removed, and technically, the round window is no longer present), as represented by fluid flow path 421 and arrow 401X, and pushes the fluid towards the oval window 402, as represented by fluid flow path 422, which is bifurcated for most of the length of the cochlea by the cochlear partition 441. Subsequently, a suction force represented by arrow 401Y is applied by the actuator assembly 361, which forces fluid away from the oval window 402, as represented by fluid flow track 422Y, and pulls fluid towards the round window 121X, as represented by fluid flow path 421Y.

That said, in an alternate embodiment, a force can be applied to the oval window 422 in a reciprocating manner to enable fluid flow into and out of the cochlea via the round window. By way of example only and not by way of limitation, instead of the utilization of a piston and cylinder arrangement as detailed above, the piston can be completely removed from the cylinder, and the transducer can be moved to be proximate or otherwise in line with the oval window 422. An armature or the like can be connected to the oval window so as to alternatingly apply a compressive force and a tensile force on the oval window, which will cause fluid to be correspondingly forced out of the cochlea and then sucked into the cochlea through the round window, and thus into and out of the cylinder (or, in more general terms, the internal volume of the actuator assembly 361 that interfaces with the round window). In at least some exemplary embodiments, the end result can be potentially effectively the same vis-à-vis evoking a hearing percept as a result of fluid flow into and out of the cochlea. Also, in at least some exemplary embodiments associated with the mixing of the therapeutic substance with the fluid that is flown into and out of the cochlea or otherwise delivering the therapeutic substance into the cochlea, the end result can be potentially effectively the same.

Briefly, it is noted that while the embodiments detailed above have focused on the mixing of the therapeutic substance with the cochlea fluid at a location outside the cochlea, in an alternate embodiment, the actuator assembly can be configured so as to directly inject the therapeutic substance into the cochlea without mixing the therapeutic substance with the fluid from the cochlea outside the cochlea. By way of example only and not by way of limitation, in an exemplary embodiment, a piston stroke can completely exhaust the fluid and/or at least substantially exhaust the fluid in the chamber 799, whereby the valve 742 is closed, and then the valve 732 is open, such that the upstroke of the piston draws in the therapeutic substance into the chamber 799, whereupon valve 732 is closed, and then valve 742 is open, and then the downstroke injects the therapeutic substance into the cochlea. Accordingly, in an exemplary embodiment, the implantable apparatus is configured to inject the therapeutic substance with no and/or minimal mixing of the therapeutic substance with another fluid, such as through the cochlea, prior to injection into the cochlea.

In an exemplary embodiment, per unit volume, the amount of therapeutic substance that is mixed with the fluid extracted from the cochlea, where the mixing occurs in the chamber 799, amounts to a ratio of less than, equal to or about equal to or greater than 0, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, where the volume of the fluid extracted from the cochlea is in the numerator and the volume of the therapeutic substance is in the denominator, for a given injection regime and/or for a given full stroke of the piston. Conversely, in an exemplary embodiment, per unit volume, the amount of therapeutic substance that is mixed with the fluid extracted from the cochlea when the device is evoking a hearing percept is less than, about equal to and/or greater than any one or more of the aforementioned values, except where, the numerator is the volume of the therapeutic substance and the denominator is the volume of the fluid extracted from the cochlea. In this regard, it is to be understood that in at least some exemplary embodiments, it may be impossible to purge all of the cochlear fluid and/or all of the therapeutic substance. That said, in some exemplary embodiments, the therapeutic substance delivery may be a very slow delivery, where the amount of therapeutic substance that is injected into the chamber for a given stroke is almost de minimis, save for the fact that there are repetitions of potentially hundreds and/or thousands and/or tens of thousands and/or hundreds of thousands of times vis-à-vis the actuation of the actuator.

With respect to mixing or otherwise delivering the therapeutic substance into the cochlea, the above embodiments of FIGS. 7-12 enable the evocation of a hearing percept irrespective of the utilization of the therapeutic substance delivery system of the embodiment of FIG. 5 or variations thereof. To be clear, in at least some exemplary embodiments, there is a hearing prosthesis that does not include the therapeutic delivery system. That said, some embodiments can utilize the embodiments of FIGS. 7 to 12 or variations thereof in combination with a therapeutic substance so as to deliver such the cochlea. Some exemplary embodiments will now be described utilizing the embodiments of FIGS. 7 to 12 is a base design. It is to be clear that other exemplary embodiments can include variations thereof, some of which variations will be described in greater detail below.

Figure 13:
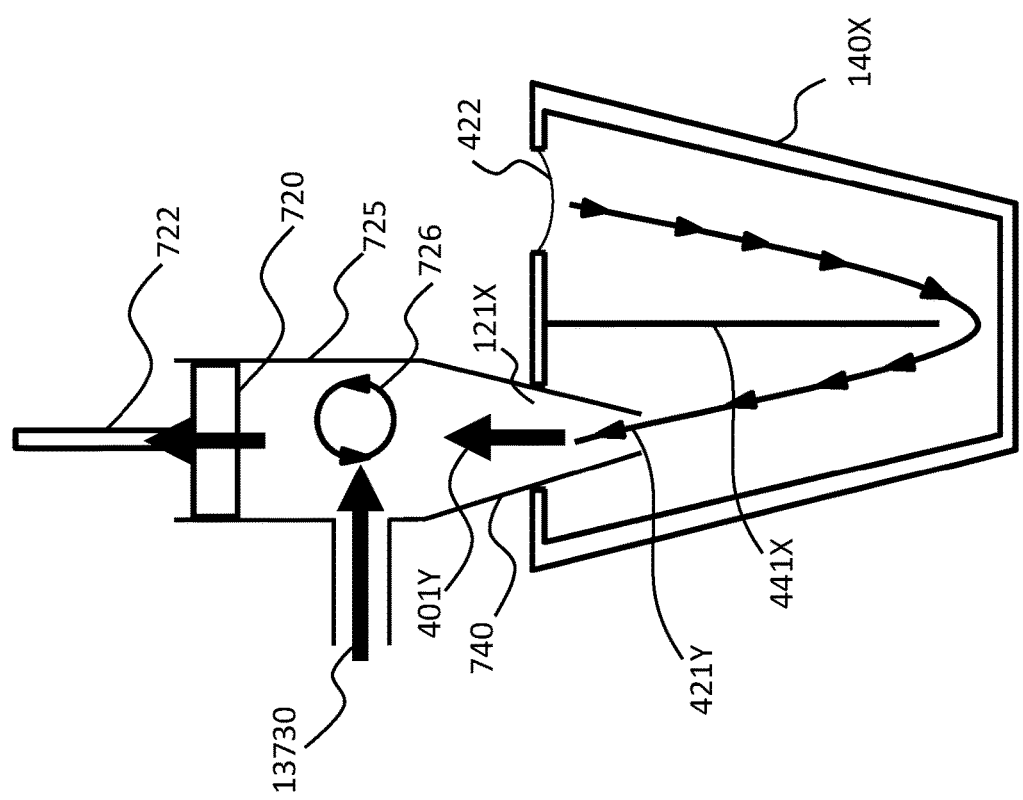

FIG. 13 represents the actuator assembly coupled to or otherwise interfacing with the cochlea via the round window 121X (in this embodiment, the outside surface of the cochlea interface component 740 is threaded or otherwise includes components that are configured to secure the actuator assembly to the cochlea, but as noted above, in an alternate embodiment, a pre-position coupling or the like can be present at the round window, such that the actuator assembly can be so configured so as to couple to that coupling without directly interfacing with the bony structure of the cochlea—any arrangement that can place the interior volume of the actuator assembly into fluid communication with the cochlea that can enable the teachings detailed herein can be utilized in at least some exemplary embodiments). Here, the valves are not shown for ease of illustration, but they are present in at least this embodiment.

FIG. 13 depicts the piston 720 on the upstroke, thus sucking fluid from the cochlea into the interior volume of the actuator assembly, as represented by arrow 401Y. In this embodiment, the valve 732 is open (in an exemplary embodiment, the valve 732 is a one-way valve, while in other embodiments, it can be a two-way valve—the valve can be controlled via a controller of the implant to open and close and/or the valve can be a valve that automatically opens and closes based on pressure (e.g., a dumb one way valve, a check valve)). Because the valve 732 is open, therapeutic substance from the tube 730 is drawn into the interior volume of the actuator, represented by arrow 13730. The therapeutic substance is entrained with the fluid that is drawn into the interior volume via the "upstroke" of the piston 720, as represented by the circular arrow symbol 726. In an exemplary embodiment, the entrainment is a result of the general characteristics of fluid flow when two flows meet. In an exemplary embodiment, there are components inside the interior volume that induce turbulence or the like (e.g., rods of differing cross-section extending partially or completely across a volume, bumps on the surfaces of the interior of the actuator that establishes the volume, a fan or impeller can be present that "stirs" for example the fluid, etc.). In at least some exemplary embodiments, upon the completion of the upstroke of the piston 720, a utilitarian amount of therapeutic substance has been drawn into the volume and at least partially mixed or otherwise is co-located with the fluid from the cochlea that has been drawn into the volume.

Figure 14:
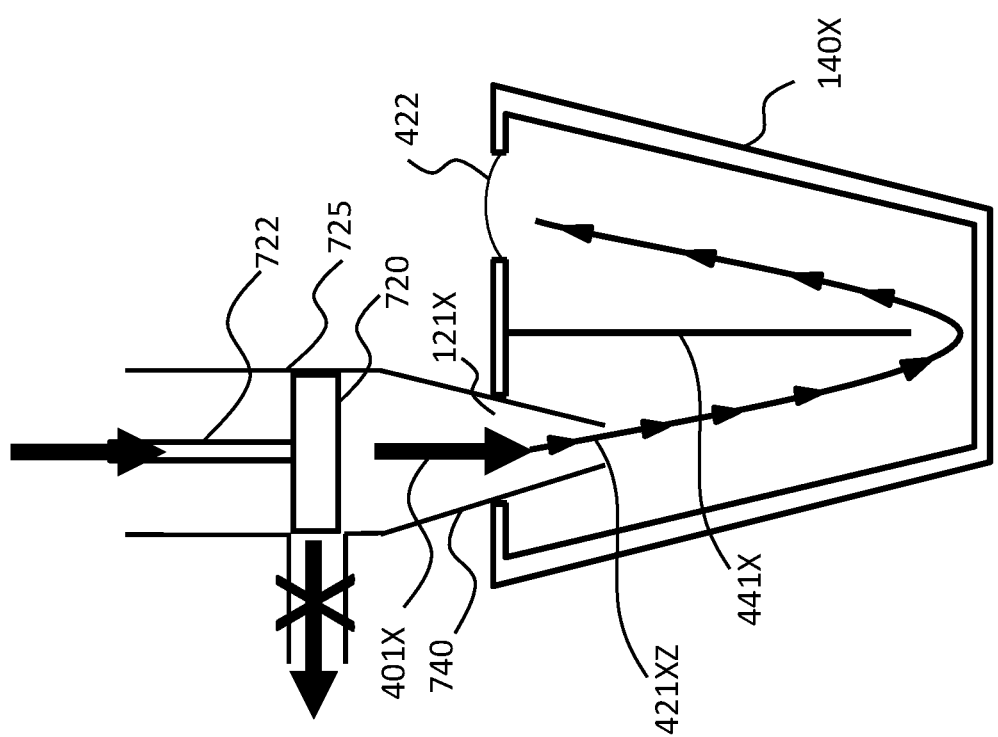
FIG. 14 depicts additional details of a conceptual schematic representing operation of an embodiment.

FIG. 14 represents the downstroke of the piston 720. Here, the valve 732 is closed, thus preventing fluid flow through the tube 730, as is schematically depicted. In this embodiment, the only way for fluid to leave the interior volume of the actuator assembly is through the tip of the cone, as can be seen. Here, fluid leaves the interior volume as represented by arrow 401X and thus enters the cochlea. In an exemplary embodiment, the fluid that leaves the interior volume is a combination of the fluid that has been withdrawn from the cochlea and the therapeutic substance that was drawn into the volume in the upstroke sub phase of the piston 720 movement. In an exemplary embodiment, the fluid is a mixture of the therapeutic substance and the fluid from the cochlea. That said, in an exemplary embodiment, the fluid and the therapeutic substance represent a slurry, where, for example, the therapeutic substance is in a solid or semi solid state. Thus, FIG. 14 can also represent the exemplary scenario where the downstroke of the piston 720 forces a slurry into the cochlea. In any event, however the therapeutic substance is introduced into the cochlea, there can be utilitarian value with doing so.

In an exemplary embodiment, the sub phases of FIGS. 13 and 14 represents in combination a single stroke phase of the actuator. In an exemplary embodiment, every stroke of the actuator can correspond to the scenario represented in FIGS. 13 and 14. That said, in an exemplary embodiment, only certain numbers of strokes can correspond to the scenario represented in FIGS. 13 and 14. By way of example, after a first stroke, one, two, three, four, five, six, seven, eight, nine, 10 or more strokes can be executed where the valve 732 is always closed both ways, and thus no additional therapeutic substance is introduced into the volume. In an exemplary embodiment, the control of the valve can be temporal-based. For example, for a period of 15 seconds, the valve 732 enables flow of therapeutic substance into the volume, and for a period of, for example, one minute, 10 minutes, 100 minutes, a day, two days, a week, etc., the valve 732 prevents flow of therapeutic substance into the volume. Note also that in an exemplary embodiment, the valve 732 can be a "dumb" valve (i.e., only the action of the piston or other pressure changing event causes the valve to open and/or close), but another valve, such as a smart valve, such as the valve 204, can be opened and closed to enable the therapeutic substance to flow into or out of the volume, or, more accurately, deliver a metered amount of therapeutic substance that will flow into the volume. With regard to this later example, the therapeutic substance that is located downstream of the valve 204 can be ultimately drawn into the chamber 799 over a period of time after the valve 204 is closed. More details of this will be described below.

In view of the above, it can be seen that in an exemplary embodiment, there is a prosthesis, such as a prosthesis that includes implant internal component 344 or 444 as modified with the therapeutic delivery system, or 644 or 744, comprising a device configured to deliver a therapeutic substance from outside a cochlea to inside the cochlea and configured to evoke a mechanically based hearing percept (as opposed to, for example, an electrically based hearing percept, such as that which occurs with a cochlear implant). Consistent with the teachings detailed above, this device is configured to drive fluid into and out of the cochlea, thereby evoking a hearing percept. Moreover, consistent with the teachings detailed above, the device is configured to drive fluid into the cochlea, thereby delivering the therapeutic substance to inside the cochlea. In embodiments where the device is configured to drive fluid into and out of the cochlea, in at least some exemplary embodiments, such can result in the simultaneous evoking of a hearing percept and the delivery of the therapeutic substance to inside the cochlea.

As noted above, in at least some exemplary embodiments, the mechanically based hearing percept is a result of the device being configured to generate waves of fluid motion in the cochlea to evoke a hearing percept. In an at least some exemplary embodiments, the generation of waves of fluid motion in the cochlea to evoke a hearing percept are generated using fluid containing the therapeutic substance.

To be clear, in at least some exemplary embodiments of the device under description, the device is configured to withdraw fluid from the cochlea, mix the therapeutic substance therewith, and inject the mixture into the cochlea, thereby delivering the therapeutic substance to inside the cochlea. In an exemplary embodiment, this action is executed while evoking a hearing percept. In an exemplary embodiment, this action is executed without evoking a hearing percept. By way of example only and not by way of limitation, this action can be executed by driving the piston at a relatively low frequency. By way of example only and not by way of limitation, this action can be executed by driving the piston at low amplitude relative to that which would otherwise be the case such as during the evocation of a hearing percept. Indeed, such an exemplary embodiment (or even in other exemplary embodiments that utilize a high amplitude or an average amplitude of the piston) can utilize an injection system that injects the therapeutic substance into the chamber 799 established by the cylinder (somewhat analogous to, for example, a fuel injection system). That is, in an exemplary embodiment, there is a separate pump or otherwise pressurization system that pressurizes the therapeutic substance so as to inject the therapeutic substance or otherwise induce flow of the therapeutic substance into the chamber 799 irrespective of the movement or displacement of the piston 720. That said, a pump may not necessarily be utilized. Instead, the therapeutic substance may be contained under a pressure that is greater than any pressure that exists in the cylinder for the entire stroke of the piston or for a certain portion of the stroke of the piston. By controlling the valve 732 to open at certain times and/or for certain length of times, the therapeutic substance will flow into the chamber 799 owing to the back pressure.

Any device, system, and/or method that can enable the therapeutic substance to flow into the chamber 799 of the actuator assembly 361 can be utilized in at least some exemplary embodiments.

In view of the above, it can be seen that the device of the prosthesis, in some embodiments, includes an electro-mechanical transducer (e.g., an EM actuator or a piezoelectric actuator). In this exemplary embodiment, the device is configured such that the electro-mechanical transducer is configured to drive the therapeutic substance from outside the cochlea to inside the cochlea (e.g., push the therapeutic substance from outside the cochlea to inside the cochlea). This can be done irrespective of whether the implant utilizes the aforementioned pressurized system or therapeutic substance injectors to drive the therapeutic substance into the chamber 799 of the cylinder. Still further, in this exemplary embodiment, the device is configured such that the electro-mechanical transducer can pull perilymph or another fluid located inside the cochlea to outside the cochlea and then push the perilymph or another fluid back to inside the cochlea, thereby evoking a hearing percept.

It is noted that the implant can be configured to flow fluid into and out of the cochlea at a frequency that can have utilitarian value. Note further that the implant can be configured to flow fluid into and out of the cochlea at frequencies that are adjustable and otherwise different from one another, and in a manner that can be controlled. Indeed, such can have utilitarian value with respect to evoking a hearing percept that more generally corresponds to natural hearing relative to that which would be the case if the device can only operate in a single frequency.

By way of example only and not by way of limitation, in an exemplary embodiment, the implant is configured to evoke a hearing percept in the range of 200 to 8000 Hz, or 200 to 10,000 Hz, or 200 to 12,000 Hz, or a range that has a lower value and/or an upper value according to those detailed. In an exemplary embodiment, the implant is configured to evoke a hearing percept at frequencies having any value or range of values between an inclusive of a range of 100 to 15,000 Hz in one hertz increments (e.g., 222 Hz to 8424 Hz (inclusive), 1,000 Hz (monotone embodiment), etc.).

In an exemplary embodiment, the frequency of fluid flow flowing into and out of the cochlea can thus correspond to the aforementioned frequencies. Accordingly, in an exemplary embodiment, the implant is configured to drive the piston 720 at the aforementioned frequencies to evoke a hearing percept.

It is noted that in at least some exemplary embodiments, the therapeutic substance can be delivered while the implant is evoking a hearing percept or otherwise driving the piston at the aforementioned frequencies. That said, in some embodiments, the implant is configured so as to operate in a lower frequency or different frequency mode when delivering the therapeutic substance. By way of example only and not by way of limitation, in an exemplary embodiment, the implant can be configured to drive the piston at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 Hz when delivering the therapeutic substance to the cochlea. In an exemplary embodiment, the implant can be configured to drive the piston at lower values or higher values than those just detailed when delivering the therapeutic substance to the cochlea. By way of example and not by way of limitation, the piston can be driven at $\frac{1}{100}^{th}$ of a Hz, $\frac{1}{200}^{th}$ of a Hz, $\frac{1}{50}^{th}$ of a hz, $\frac{1}{10}^{th}$ of a Hz, etc. accordingly, by way of example only and not by way of limitation, in an exemplary embodiment, the implant can be configured to drive the piston at any value within a range of values (inclusive of) $\frac{1}{200}^{th}$ to 40 Hz and any value or range of values therebetween in $\frac{1}{1000}^{th}$ of a Hz increment (e.g., $\frac{1}{222}$th of a Hz to 4.31 Hz, 0.11 Hz, etc.) Any frequency of operation that can have utilitarian value with respect to drug delivery can be utilized in some exemplary embodiments, and thus the implant can be configured so as to operate at such utilitarian frequencies. In this regard, the implant can be configured so as to control the transducer 710 to drive the piston 720 at any of the aforementioned frequencies/range of frequencies.

In view of the above, in an exemplary embodiment, the device is configured to flow fluid into and out of the cochlea at a frequency of at least X, where X is 5, 10, 15, 20, 25, 30, 35, 40, 45, 50, 55, 60, 65, 70, 75, 80, 85, 90, 95, 100, 110, 120, 130, 140, 150, 160,170, 180, 190, 200, 210, 220, 230, 240, 250, 260, 270, 280, 290, 300, 325, 350, 375, 400, 425, 450, 475 or 500 Hz or any value or range of values therebetween in 1 Hz increments.

In an exemplary embodiment, the device is configured to operate in a first mode that causes the device to withdraw fluid from the cochlea, mix the therapeutic substance therewith, and drive the mixture into the cochlea, at a first frequency or first range of frequencies, thereby delivering the therapeutic substance to inside the cochlea. In this exemplary embodiment, the device is also configured to operate in a second mode that causes the device to withdraw fluid from the cochlea and not mix the therapeutic substance therewith, and drive the fluid back into the cochlea, at a second frequency or second range of frequencies, thereby evoking a hearing percept. The device can be configured with a control unit that automatically places the device into the first mode and/or into the second mode. The device can also be configured to be manually placed into the first mode and/or the second mode. A combination of these features can be utilized, such as where, for example, the first mode is entered into via the manual operation of activating the drug delivery system, but then the second mode is entered automatically upon the determination that the drug delivery period is over. In at least some of these embodiments, the first frequency and/or first range of frequencies is lower by at least about Y times than the second frequency and/or the second range of frequencies. In an exemplary embodiment, Y is 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 90, 100, 125, 150, 175, 200, 225, 250, 275, 300 or more. In an exemplary embodiment, the first frequency and/or first range of frequencies is lower by at least about one or two or three orders of magnitude than the second frequency and/or the second range of frequencies.

In some of the embodiments detailed above, the action of withdrawing fluid from the cochlea, mixing the therapeutic substance therewith, driving/injecting the mixture into the cochlea, at the first frequency or first range of frequencies, evokes a hearing percept. That is, the action of delivering the therapeutic substance to the cochlea is not mutually exclusive with respect to evoking a hearing percept, at least in some embodiments. That said, as detailed above, in some other embodiments, the action of delivering the therapeutic substance to the cochlea is usually exclusive with respect to evoking a hearing percept.

It is noted that in at least some exemplary embodiments, the components of the device that evoke a hearing percept are the same components that deliver the therapeutic substance to the cochlea (e.g., the piston, the chamber 799 formed by the cylinder and the cone, the valve 742, the transducer 710). In an exemplary embodiment, the configuration of the device is such that the device cannot deliver the therapeutic substance if the device cannot evoke a hearing percept and/or vice versa. In an exemplary embodiment, the configuration of the device is such that if the components that are utilized to evoke a hearing percept are not operational or otherwise not functional, the therapeutic substance is not deliverable to the cochlea (at least with respect to the embodiment where the fluid is withdrawn from the cochlea, the therapeutic substance is entrained or otherwise mixed with the fluid, and then the fluid is injected into the cochlea). By way of example only and not by way of limitation, the transducer 710 is the same transducer that is utilized to evoke a hearing percept as well as to inject the fluid containing the therapeutic substance into the cochlea. Thus, if the transducer 710 is not operational, the therapeutic substance cannot be injected into the cochlea.

In view of the above, it can be seen that in an exemplary embodiment, the device detailed above is a fluidic based device. This as opposed to, for example, a device that moves a counter mass or the like to evoke a hearing percept, or otherwise imparts a force on to a component of the ear via a solid structure.

In an exemplary embodiment of the device of the prosthesis detailed above, the device is a fluidically unified device. In this regard, by way of example only and not by way of limitation, this is the case because the device utilizes the same outlet and same internal volume to deliver the therapeutic substance into the cochlea and to drive the fluid withdrawn from the cochlea into the cochlea. This as opposed to, for example, an arrangement that utilized a "double barrel" configuration, with one barrel utilized to deliver the fluid withdrawn from the cochlea into the cochlea, and another, separate barrel utilized to deliver the therapeutic substance.

Returning to FIG. 9, it can be seen that there is a valve 742 located at the outlet of the actuator assembly. In this exemplary embodiment, this is a two-way valve. In an exemplary embodiment, valve 742 can be controlled to be opened and then closed. In an exemplary embodiment, after the fluid is drawn into the chamber 799 from the cochlea, the valve is closed. In an exemplary embodiment, this can provide the therapeutic substance time to mix with the fluid that has just been drawn into the chamber 799. After a given period of time, such as a period of time where empirical and/or analytical data indicates that the therapeutic substance is utilitarian with the mixed with the fluid, the valve 742 is opened, and the piston 720 is driven downward, thus injecting the mixture into the cochlea.

That said, in some exemplary embodiments, after the valve is closed, the piston 720 can be actuated even though the system is closed. Such can have utilitarian value with respect to mixing the therapeutic substance with the fluid. Alternatively, and/or in addition to this, in an exemplary embodiment, the increased pressure and/or heat resulting from the piston operating in a closed environment can potentially activate the active ingredient in the therapeutic substance. Alternatively, and/or in addition to this, in an exemplary embodiment, the piston 720 can include flapper valve or a one-way valve that permits fluid to flow from one side of the piston to the other, which can have utilitarian value with respect to mixing the therapeutic substance. Also, such can have utilitarian value with respect to raising the temperature of the fluid or whatever substances is in the chamber 799 without substantially increasing the pressure. In an exemplary embodiment, this temperature change can activate an active ingredient. Still further, in an exemplary embodiment, this temperature change can liquefy what was a solid, such as embodiments where the therapeutic substance is in a solid or semi solid state prior to introduction into the fluid.

In any event, it is to be understood that in at least some exemplary embodiments, the valves of the system are controllably opened and/or closed so as to manage the physical features associated with the fluid system of the device.

Briefly, it is noted that in at least some exemplary embodiments, the chamber 799 established by the cylinder and/or the cochlea interface component 740 includes electrodes or the like such that an electric charge can be applied to the mixture, which can have utilitarian value with respect to activating the active ingredient or otherwise enhancing mixing. Alternatively, and/or in addition to this, resistance heaters can be present in the device which can be utilized to increase the temperature within the chamber 799, again which can have utilitarian value with respect to potentially activating an active ingredient.

Figure 15:
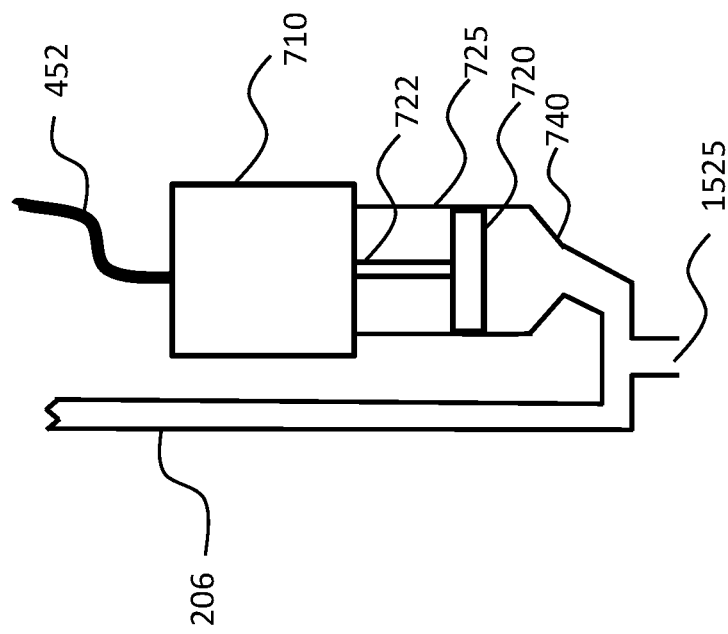
FIGS. 15-20 are schematics depicting some additional exemplary embodiments.

In view of the above, it can be seen that at least some exemplary embodiments provide a system that includes at least two subsystems, a drug delivery subsystem, and an energy delivery subsystem. Consistent with the teachings detailed above, the drug delivery subsystem is configured to deliver a drug to a cochlea of a recipient, and the energy delivery subsystem is configured to evoke a hearing percept via fluid flow generation. As can be seen above, in some embodiments, both subsystems configured to access the cochlea at a common location (e.g., through the round window, through a cochleostomy, or the oval window). It is noted that the embodiment of FIG. 7 detailed above is such an arrangement that has such subsystems, even though the subsystems are somewhat integrated. FIG. 15 presents an alternate embodiment that also includes the aforementioned subsystems, albeit in a less integrated manner. Here, this embodiment is more akin to the embodiment of FIG. 6A detailed above. Drug delivery tube 206 extends to a junction with the inlet/outlet of the chamber 799 established in part by the cylinder 725. Here, there is a common inlet/outlet 1525, but beyond that, the subsystems are generally separated. That is, the integration here occurs at the junction of the two subsystems, which is essentially at the outlet. Still, it is to be understood that the function of the embodiment of FIG. 15 operates in a generally similar manner than the embodiment of FIG. 7 detailed above. In the embodiment depicted in FIG. 15, the outlet 1525 is in the form of a bayonet coupling that sealingly couples to a meeting coupling that is surgically implanted into the cochlea at the oval window, the round window, or a cochleostomy. Such an embodiment still access the cochlea at a common location.

Figure 16:
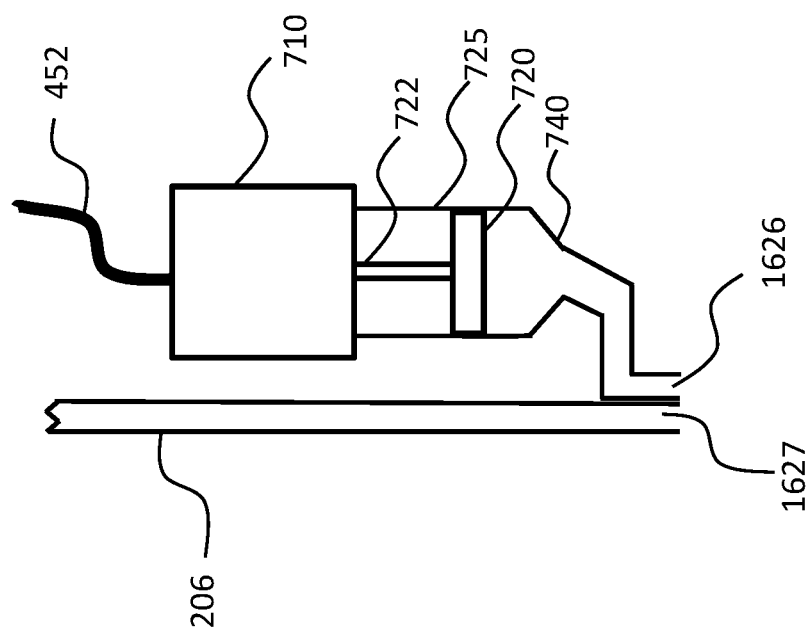

Consistent with the teachings above, the common location is a common port into the cochlea such that the system is in fluid flow communication to an interior volume of the cochlea. The embodiments detailed above vis-á-vis FIGS. 7 and 15 present a drug delivery sub-system and the energy delivery sub-system are part of an integrated system. That said, in some alternate embodiments, the drug delivery subsystem and the energy delivery subsystem are not part of an integrated system. Instead, the systems are bifurcated. FIG. 16 present such an exemplary embodiment, where the drug delivery system has a separate outlet 1627 from the outlet 1626 of the energy delivery subsystem. In an exemplary embodiment, both subsystems access the cochlea at the same location, while in an alternate embodiment, the subsystems access the cochlea at different locations. It is noted that some embodiments of FIG. 16 can be such that a common chassis or the like is utilized to support components of the energy delivery system and the drug delivery system. By way of example only and not by way of limitation, a reservoir containing the drug to be delivered can be located in the stimulator unit 320. It is also noted that some embodiments of FIG. 16 can be such that the various components can be in communication with each other. By way of example only and not by way of limitation, a control unit in the stimulator unit can activate the drug delivery subsystem. Still, such embodiments do not present integrated subsystems, but instead subsystems that share some components of the overall system. That is, for example, the system can have a common control unit, and the subsystems can still be non-integrated.

Thus, as can be seen, an embodiment includes a plurality of tubes that enter the cochlea, where a first tube is utilized for delivery of drugs (e.g., solely and exclusively in at least some embodiments) and a second tube is utilized for the generation of sound (e.g., solely and exclusively in at least some embodiments). It is noted that while the embodiment of FIG. 16 depicts an opening 1626 of the tube used to generate sound, this second tube can instead be sealed at an end thereof (e.g., with a diaphragm or the like, which movement thereof due to the pressure changes in the tube will cause the diaphragm to flex in and out, and thus induce vibrations in the cochlea that evoke a hearing percept). In an exemplary embodiment, the flow out of tube 206 (the first tube) can be such that the flow flows in only one direction (e.g., out opening 1627). In an exemplary embodiment, the flow out of the first tube flows at a volumetric rate (average and/or instantaneous) such that it does not generate the perception of sound, or at least does not generate a noticeable perception of sound, or at least does not generate a perception of sound that would be distinguishable from general background sounds in an environment. Thus, in an exemplary embodiment, only the second tube (which can be sealed, but is not sealed in some other embodiments) evokes a hearing percept.

Consistent with the teachings detailed above, it is to be understood that in at least some exemplary embodiments, the drug delivery subsystem and the energy delivery subsystem use substantially the same transport components to deliver drug into the cochlea from outside the cochlea and to stimulate the cochlea to evoke a hearing percept. By transport components, it is meant the components that are used to transport the fluid in the drug from outside the cochlea to inside the cochlea, such as, for example, the piston, the transducer, the plumbing. This as opposed to, for example, the reservoir containing the drug or the delivery tube 206, etc.

Also, in view of the above, it can be seen that the energy delivery sub-system includes an electro-mechanical transducer (an EM actuator, for example), and the system is configured to drive the drug into the cochlea using the electro-mechanical transducer.

As noted above, the prosthesis can operate in different modes, a first mode that is a drug introduction mode, and a second mode that is a hearing prosthesis mode. To this end, in an exemplary embodiment, the system includes a controller that controls the system to at least variously operate in these first and second modes. As noted above, the modes can be mutually exclusive modes that do not overlap one another, while in other embodiments, the modes can overlap one another. Indeed, in an exemplary embodiment, the system can be configured to operate in both the first mode and the second mode at the same time and operate in at least one of only the first mode to the exclusion of the second mode were only the second mode to the exclusion of the first mode in some instances. In an exemplary embodiment, the controller can be located in and/or be part of the stimulator unit 320 detailed above. By way of example only and not by way of limitation, the implant internal component 744 of FIG. 6D can correspond to such an embodiment.

It is noted that the embodiments detailed above are such that all active components of the system are located outside the cochlea. That said, in an alternative embodiment, there are active component(s) located within the cochlea, and in some embodiments, both inside and outside the cochlea.

Figure 17:
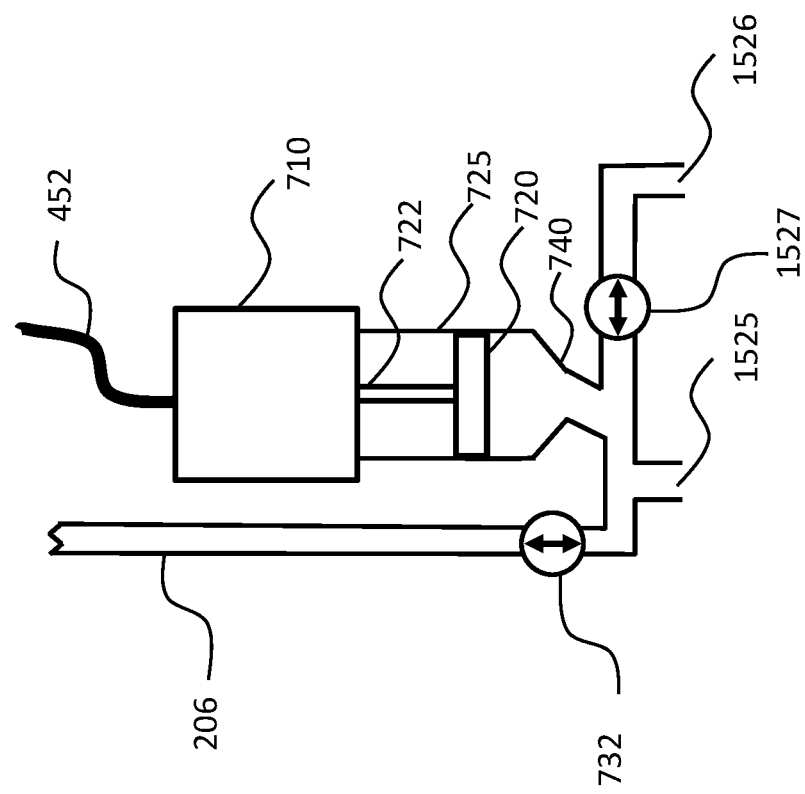

It is briefly noted that while the embodiment of FIG. 7 has been described above in terms of a 1 to 1 flow of fluid into and out of the cochlea at the location at which the cochlea is accessed with respect to a given stroke of the piston 720, in an alternate embodiment, different volumetric flow amounts can be applied for a given stroke and/or a sub stroke. By way of example only and not by way of limitation, FIG. 17 depicts an exemplary embodiment where the actuator includes two outlets/inlets—1525 and 1526. Valve 1527 is interposed between the two as can be seen. In this exemplary embodiment, the valve 1527 can be operated so as to effectively close or open inlet/outlet 1526 or otherwise restrict the flow of fluid into and out of inlet/outlet 1526. By way of example only and not by way of limitation, such can have utilitarian value with respect to controlling the overall momentum of the fluid that is withdrawn from the cochlea and/or injected to the cochlea. For example, in an exemplary embodiment, there can be utilitarian value with respect to dispersing the intake stroke over two or more locations of the cochlea, and then closing valve 1527 and then concentrating the injection stroke at a given single location of the cochlea. Alternatively, the reverse can be applied. In an exemplary embodiment, valve 1527 can be utilized during periods where the therapeutic substance is to be applied to the cochlea but a hearing percept is to be avoided. Indeed, in an exemplary embodiment, inlet/outlet 1525 can be located at one basil end of the cochlea (e.g., through the round window) and inlet/outlet 1526 can be located at the other end of the basal cochlea (e.g., through a cochleostomy adjacent the oval window). In an exemplary embodiment, when the valve 1527 is open, it is possible that in at least some exemplary embodiments, the waves of fluid motion that are typically produced by actuation of the actuator are not produced or otherwise limited relative to that which would be the case because the intake and injection of the fluid is dispersed over both ends of the cochlea as opposed to being concentrated at one end. That is, in an exemplary embodiment, during therapeutic drug delivery, the valve 1527 can be opened to avoid a hearing percept as a result of the actuation of the actuator, and then, to evoke a hearing percept, the valve 1527 can be closed. It is also noted that such can have utilitarian value potentially even when the actuator is driven at a high frequency. That is, the actuator might be driven at a high frequency but because both inlet/outlet 1526 and 1525 are being utilized at the two separate locations of the cochlea, the hearing percept is avoided or otherwise reduced relative to that which would otherwise be the case if the valve 1527 was closed. It is also noted that the embodiment of FIG. 17 can be utilized with inlet/outlet 1525 and 1526 communicating with the cochlea at two separate locations but on the same end of the cochlea (e.g., one through the round window and the other through a cochleostomy adjacent the round window). Such can have utilitarian value with respect to diffusing the momentum of the fluid being injected into the cochlea at one location.

Figure 18:
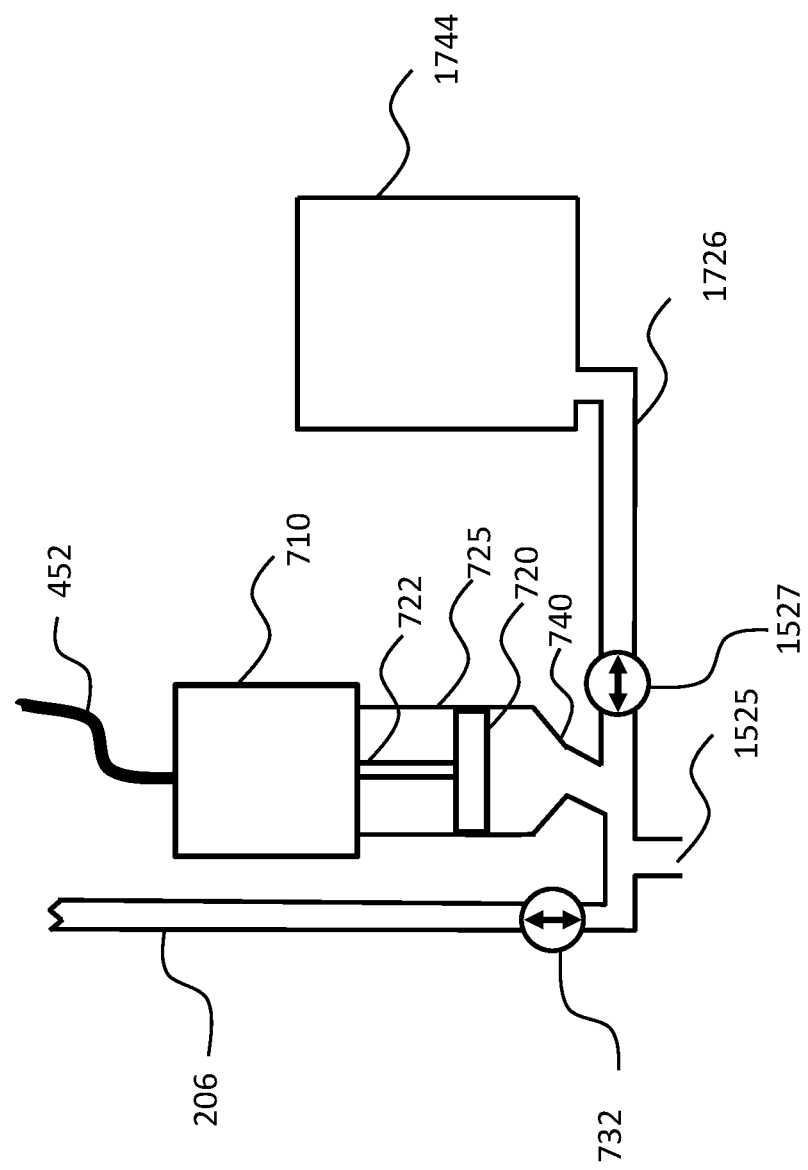

FIG. 18 depicts an alternate embodiment that is configured to defuse or otherwise reduce the momentum of the fluid being injected into the cochlea relative to that which would otherwise be the case. Here, there is only one inlet/outlet in fluid communication with cochlea, inlet/outlet 1525. However, valve 1527 leads to a conduit 1726 which in turn leads to a reservoir 1744. Reservoir 1744 can be a quasi-expansion tank and can be configured to reduce the amount of fluid that is withdrawn from the cochlea for a given piston stroke relative to that which might otherwise be the case if the valve 1527 was closed and/or vice versa and/or reduce the amount of fluid that is injected into the cochlea for a given piston stroke relative to that which might otherwise be the case in the valve 1527 was opened and/or vice versa. For example, in an exemplary scenario of use, where reservoir 1744 is configured to have a variable volume therein (e.g., via a floating piston or a flexible diaphragm, etc.), with the valve 1527 open, for a given intake stroke, some fluid will be drawn into the chamber 799 via inlet/outlet 1525 and some fluid will be drawn into the chamber 799 through the open valve 1527 from the reservoir 1744, thus reducing the amount of fluid that has been withdrawn from the cochlea for an overall stroke. Conversely, for a downward stroke, with the valve open, the amount of fluid that flows through inlet/outlet 1525 will be reduced relative to that which would otherwise be the case because some of the fluid will also flow into the reservoir 1744, which, owing to the variable nature of the interior volume therein, can have a low or no back pressure value thus enabling some of the fluid to flow into the reservoir. Still further, in an exemplary embodiment, such as where it is utilitarian to increase the momentum of an injection stroke relative to the intake stroke for whatever reason, in an exemplary embodiment, for a given uptake stroke, during intake stroke, the valve 1527 can be open, thus drawling some fluid from the reservoir 1744 into the chamber 799, and for the injection stroke, valve 1527 can be close, thus injecting all of the fluid into the chamber 799 out the inlet/outlet 1525 and thus into the cochlea. It is to be understood that the reverse can also be the case.

It is to be understood that in at least some exemplary embodiments, reservoir 1744 can function as a dampening chamber for the system.

Figure 19:
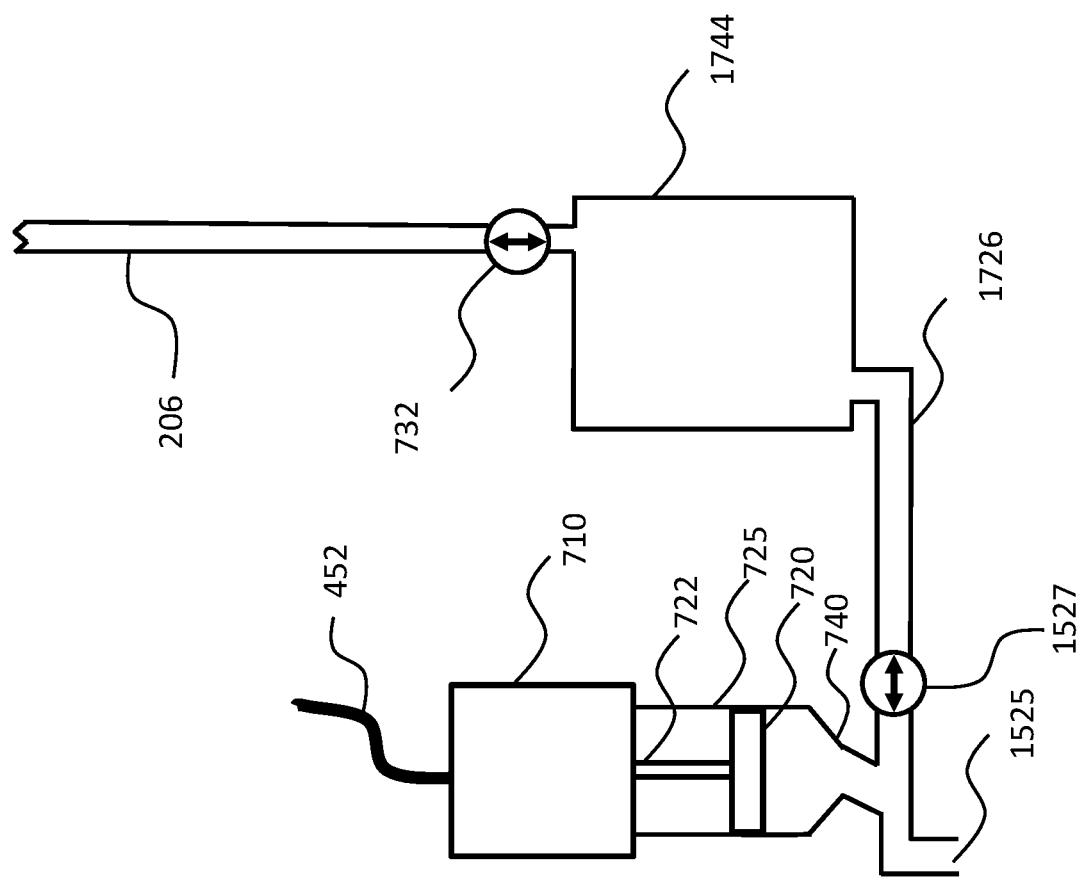

FIG. 19 depicts an alternate embodiment that utilizes the reservoir 1744 as a mixing chamber 799 that can be fluidically isolated from the chamber 799 established by the cylinder. In this regard, in an exemplary embodiment, via a valve at the inlet/outlet 1525 (not shown) in conjunction with operation of the valve 1527, the reservoir 1744 can be periodically charged with fluid withdrawn from the cochlea. In an exemplary embodiment, the therapeutic substance can be injected or otherwise delivered to the reservoir via control of valve 732 which can be a one-way valve or a two-way valve (it is noted that all disclosure of all valves herein corresponds to a disclosure of a one-way valve and a disclosure in another embodiment of a two-way valve irrespective of what the valves are identified as in the text). Here, the therapeutic substance can mix with the fluid in the reservoir 1744 over a period of time, in isolation from the chamber 799 established by the cylinder. When it is deemed suitable for the mixture to be injected into the cochlea, valve 1527 can be opened and, in an example, the un-shown valve at the inlet/outlet 1525 can be closed, and the intake stroke of the piston 720 can withdraw fluid from the reservoir 1744 that contains the therapeutic substance mixed therein, and in the valve 1527 can be closed and the un-shown valve opened, and then with the downstroke of the piston 720, the fluid with the therapeutic substance mixed therein can be injected into the cochlea.

Briefly, as noted above, there can be a valve 742 at the outlet of the actuator assembly. It is noted that in at least some exemplary embodiments, the amount of opening of the valve can be varied so as to vary the speed at which the fluid is injected into the cochlea. By way of example only and not by way of limitation, by closing the valve halfway, for a given piston stroke, the speed at which the fluid is injected in the cochlea will be relatively double to that which would be the case if the valve is opened all the way. There can be utilitarian value with respect to controlling the speed of the fluid that is injected into the cochlea.

Figure 20:
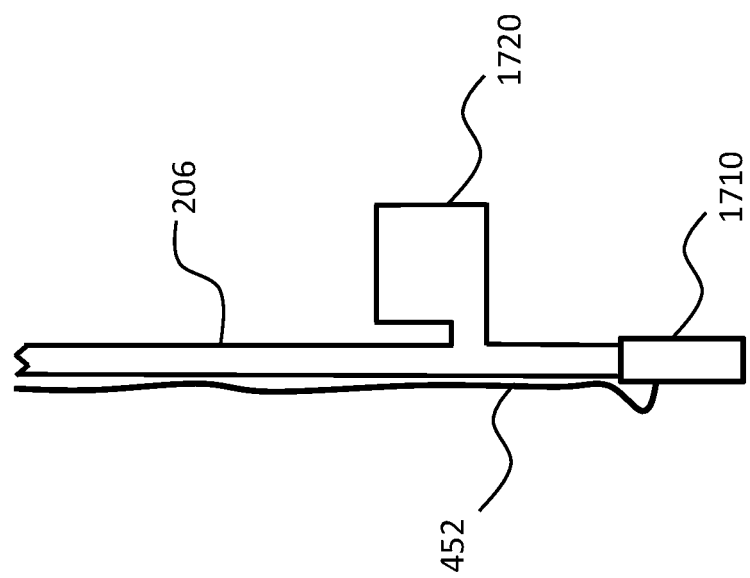

While the embodiments detailed above have focused on embodiments where all the active components are located outside the cochlea, FIG. 20 depicts an exemplary embodiment where an active component, actuator 1710, is located in the cochlea. In this regard, actuator 1710 serves in a manner analogous to a submerged sump pump. Actuator 1710 pumps fluid into and out of the cochlea via a conduit which can be an extension of the drug delivery tube 206. As can be seen in FIG. 20, there is a reservoir 1720 at the side of tube 206. In an exemplary embodiment, a valve (not shown) above the conduit to the reservoir 1720 can be opened and closed, and the actuator 1710 can be used to pump the fluid into and out of the cochlea at the various frequencies detailed above, where the fluid pumped out of the cochlea can be flown into the reservoir 1720 and the fluid pumped into the cochlea can be flown out of the reservoir 1720. Any device, system, and/or method for moving fluid from in the cochlea to outside the cochlea and vice versa can be utilized in at least some exemplary embodiments. Indeed, the configuration of FIG. 20 can be combined with the configuration of, for example, FIG. 7 detailed above. In an exemplary embodiment, pumped 1710 can be utilized for therapeutic substance delivery, and the pump outside the cochlea can be utilized to evoke a hearing percept, all by way of example only and not by way of limitation.

In an exemplary embodiment, there is a device comprising a hydraulic hearing prosthesis configured to move a fluid into and out of the cochlea to evoke a hearing percept. In an exemplary embodiment, this corresponds to the embodiments of FIGS. 7 and 15 etc. detailed above. That said, in an alternate embodiment, this hydraulic hearing prostheses can be a hearing prostheses that is unrelated to the delivery of a therapeutic substance or the like into the cochlea. By way of example only and not by way of limitation, in an exemplary embodiment, the hydraulic hearing prostheses and correspond to that depicted in FIG. 3 or 4 detailed above, where the actuator assembly can correspond to the components not specifically and exclusively related to the therapeutic delivery system of the teachings detailed above. Of course, consistent with the teachings detailed above, in an exemplary embodiment, the prosthesis is a dual use therapeutic substance delivery device and a hearing prostheses. Still, it is noted that in some embodiments, the device is only a hearing prosthesis.

Consistent with the teachings detailed above, in at least some exemplary embodiments, the prosthesis expands a volume of the cochlea relative to that which is the natural state of the cochlea. In this regard, in an exemplary embodiment, the chamber 799 formed by the cone and the cylinder, when in fluid communication with the cochlea, results in a volume that is greater than the volume of the cochlea in its natural state. This thus expands the volume of the cochlea in a manner analogous to an addition or the like expanding the square footage of a house. By way of example only and not by way of limitation, the cochlea in its natural state can correspond to a first volume having a volume of A and the chamber 799 established by the cylinder and the cone can correspond to a second volume having a volume of B, and when the first volume is in fluid communication with the second volume, the combined volume is A+B, as opposed to just the volume of a which corresponds to the volume of the cochlea in its natural state.

In an exemplary embodiment, the aforementioned prosthesis is configured to move at least a subset volume of the fluid that is moved into and out of the cochlea at a rate of at least X (where the values of X have been detailed above). For example, in an exemplary embodiment, the prosthesis is configured to move at least a subset volume of the fluid into and out of a cochlea at a rate of at least 100, 150, 200, 250, or 300 Hz. It is noted that the aforementioned subset volume, or specifically, the fluid in that subset volume, can be different for each movement into and out of the cochlea owing to the fact that the volume is not contained by a physical structure. Any frequency of movement of the subset volume of fluid into and out of the cochlea that can have utilitarian value with respect to evoking a hearing percept can be utilized in at least some exemplary embodiments.

Still continuing with the embodiment of the prosthesis configured to move fluid into and out of the cochlea to evoke a hearing percept, in an exemplary embodiment, the prosthesis includes an actuator the output of which is only fluidically coupled to the cochlea. In an exemplary embodiment, the device under discussion is a device that includes an actuator and the device is configured such that the device is substantially free of vibration that causes perceptible sound when the actuator is actuated to evoke a hearing percept and/or the device is configured such that the device imparts substantially no vibrational energy to the cochlea when the actuator is actuated to evoke a hearing percept.

As noted above, in some exemplary embodiments of the device under discussion, the prosthesis is a dual use therapeutic substance delivery device and hearing prosthesis.

With reference to such an exemplary embodiment as detailed above with respect to FIG. 7, by way of example only and not by way of limitation, the device can include a therapeutic substance mixing chamber 799, such as the chamber 799 that is formed at least in part by the cylinder of FIG. 7. In this exemplary embodiment, the prosthesis is configured to intake and eject perilymph from and to the cochlea into and out of the chamber during movement of the fluid into and out of the cochlea. Still further, the prosthesis is configured to controllably input the therapeutic substance into the mixing chamber to mix with the perilymph to deliver the therapeutic substance to the cochlea. The action of controllably importing the therapeutic substance into the mixing chamber can be executed utilizing the devices systems and/or methods detailed above or other such devices systems and/or methods. In an exemplary embodiment, the valve 732 can be actively and/or passively controlled. Again, as noted above, a drug delivery injection system can be utilized to inject the fluid into the chamber in a manner analogous to fuel injection or the like. Any device, system, and/or method that will enable the controllable inputs of the therapeutic substance into the mixing chamber can be utilized in at least some exemplary embodiments.

It is noted that the ability to control the amount of therapeutic substance that is delivered to the mixing chamber can have utilitarian value with respect to adjusting or otherwise controlling the amount of therapeutic substance that is ultimately delivered to the recipient. In an exemplary embodiment, the amount of therapeutic substance that is delivered to the chamber in one shot and/or over a given period of time can be controlled. With respect to the one shot control, in an exemplary embodiment, the valve 732 can be opened by a certain amount that can be variable to meter the amount of therapeutic substance that flows through the valve and into the chamber with respect to a given draw of the piston. Alternatively, and/or in addition to this, the amount of time that the valve is opened during that draw can be controlled so as to meter the amount of therapeutic substance that flows through the valve and into the chamber. This can be done repeatedly for a plurality of draws of the piston. Still further in an exemplary embodiment, such as where a pressurized system is utilized, the pressure behind the valve 732 can be adjusted or otherwise controlled to adjust the amount of therapeutic substance that flows through the valve during the period that the valve is opened on a per unit time and/or a per unit area opening basis. Any feature that can enable the amount of therapeutic substance that is delivered to the chamber to be increased and/or decreased for a given draw can be utilized in at least some exemplary embodiments.

That said, it is noted that in at least some exemplary embodiments, the teachings detailed herein are utilized to deliver a dosage or a sub dosage of therapeutic substance to the cochlea over a given period of time. By way of example only and not by way of limitation, in at least some exemplary embodiments, the devices detailed herein can provide for delivery of the therapeutic substance to the cochlea over the course of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or weeks, or months, or even longer, such as over the course of 3, 4, 5, 6, 7, 8, 9, or 10 years. In an exemplary embodiment, therapeutic substance is delivered at least every day and/or every two days and/or every three days and/or every four days and/or every five days and/or every six days and/or every seven days and/or every week and/or twice a week and/or twice a month and/or three times a month and/or once a month and/or once every two months and/or once every three months, and/or once every six months, and/or once a year over the aforementioned temporal periods. The delivery can be regular or may not be regular (e.g., delivery can occur once every day for three days, and then halt for a day or two, and then resume for four days, and then halt for one day or two days or three days, etc., and so on). In an exemplary embodiment, the aforementioned performance scenarios are achieved without percutaneous delivery of the therapeutic substance to the cochlea and/or to the drug delivery system. In an exemplary embodiment, a hearing percept is evoked and/or the device is returned to a state where a hearing percept can be evoked (for embodiments that affirmatively transition from one mode to another mode, where one of the mode prevents a hearing percept from occurring while the therapeutic substance is delivered) 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or 45 or 60 minutes or hours or 1, 2, 3, 4, 5, 6, 7, 8, 9 or 10 weeks of the last introduction of the therapeutic substance prior to the beginning of a new introduction of the therapeutic substance, for at least a portion of or all of the aforementioned temporal periods. Again, as noted above, in some embodiments, a hearing percept is evoked while the therapeutic substance is being delivered to the recipient.

It is also noted that some exemplary embodiments can utilize a regime where the number of times the valve 732 is opened is controlled. That is, instead of opening the valve by a certain amount or opening the valve for certain period of time and/or adjusting the back pressure with respect to a given draw, one or two or all three of these features are held constant per draw over each draw, and the number of times that the valve is opened over a given period of time and/or the number of times that the valve is opened with respect to a number of draws is controlled. (It is briefly noted that in some exemplary embodiments, the aforementioned valve control features are not held constant with respect to embodiments where the number of times of the valve is opened over a given period of time and/or with respect to the number of draws. That is, the two regimes can be combined.) By way of example only and not by way of limitation, because a given draw with respect to a given valve opening amount for a given period of valve open time at a given back pressure will result in a general constant amount of therapeutic substance flowing through valve 732 for the same front pressure and for the same piston stroke distance, by controlling the number of times that the valve is opened over a given period of time, the ultimate amount of therapeutic substance that is delivered to the recipient can be controlled.

It is noted that such control regimes can be utilized with respect to an embodiment where the prosthesis is operating in a separate mode from a mode that evokes a hearing percept as well as with respect to an embodiment where the prosthesis is operating in a mode that also evokes a hearing percept. In this regard, in an exemplary embodiment, the prosthesis can be configured to regulate therapeutic substance delivery while the prosthesis is evoking a hearing percept. Still further with respect to such an exemplary embodiment, the prosthesis can include an actuator, the actuator can be used both for delivery of the therapeutic substance and to evoke a hearing percept (the actuator is a dual use actuator, as opposed to an embodiment where separate actuators are utilized—one to evoke a hearing percept and the other to deliver therapeutic substance). In an exemplary embodiment of this exemplary embodiment, the prosthesis can be configured to control overall flow of therapeutic substance into a perilymph containing volume including an interior of the cochlea (which volume can also include the internal chamber of the actuator assembly) at least substantially all operational modes of the prostheses with respect to evoking a hearing percept.

In an exemplary embodiment where the prosthesis is a dual use therapeutic substance delivery device and a hearing prosthesis, the prosthesis can be configured to attach to a cochlea so as to be in fluid communication with an interior thereof the first location so as to move the fluid into and out of the cochlea at the first location and so as to deliver the therapeutic substance into the cochlea at the first location. This is as opposed to an exemplary embodiment where, for example, the energy impartation device is in fluid communication with the cochlea at one location, and the tube 206 of the drug delivery system is in fluid communication with the cochlea at another separate location.

It is to be understood that in at least some exemplary embodiments, the above detailed prosthesis can be characterized as a prosthesis that is a non-bone conduction hearing prosthesis configured to evoke a hearing percept with the ossicles intact. Also, in at least some exemplary embodiments, the prosthesis is configured to preserve at least a portion of a residual hearing of a recipient. By way of example only and not by way of limitation, the prosthesis is configured to preserve at least about 70%, 75%, 80%, 85%, 90%, or 95% of residual hearing after implantation. However, as will be described in greater detail below, some alternate embodiments do include a bone conduction based hearing prostheses.

Figure 21:
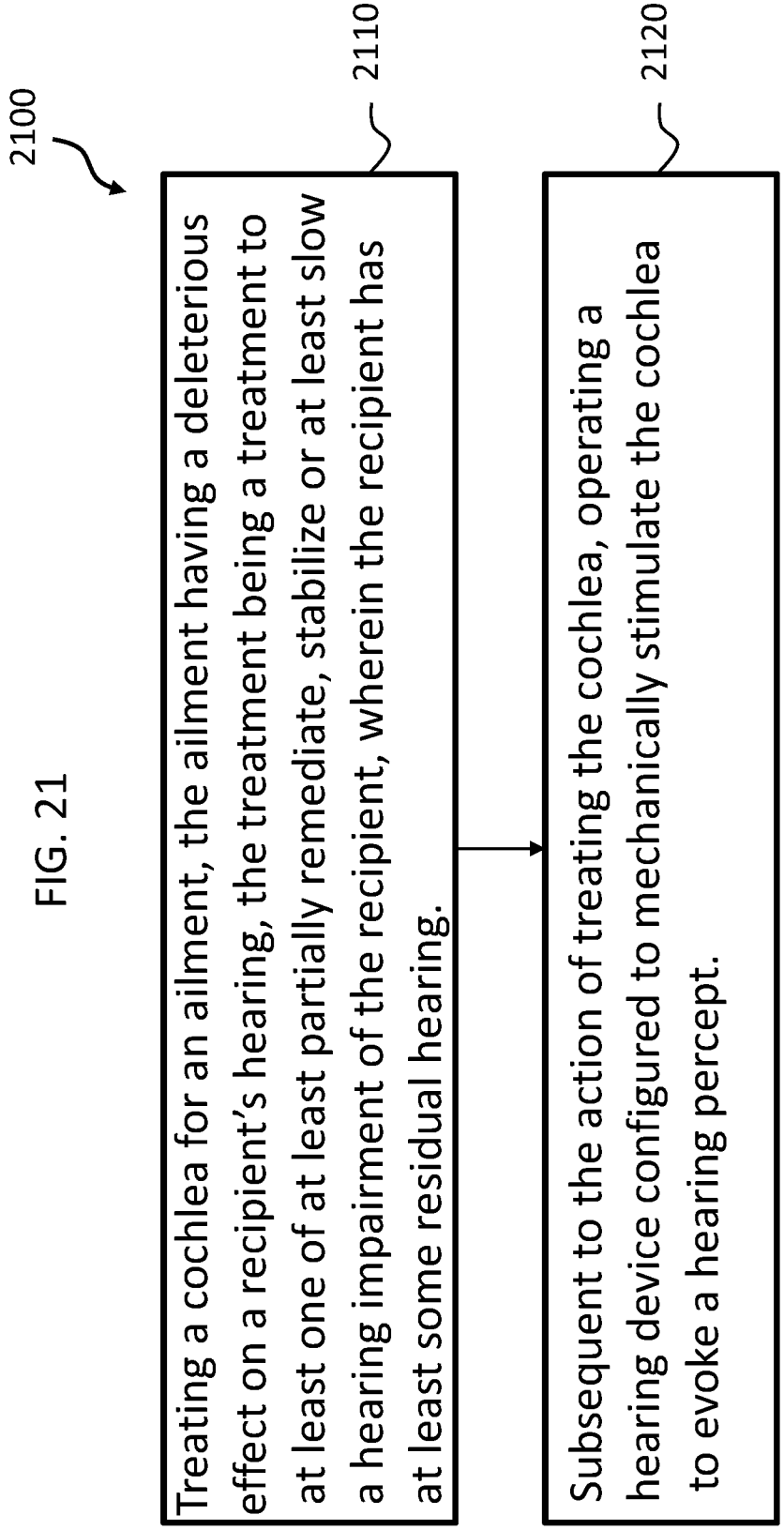
FIGS. 21-22 are flowchart representing some exemplary methods.
Figure 22:
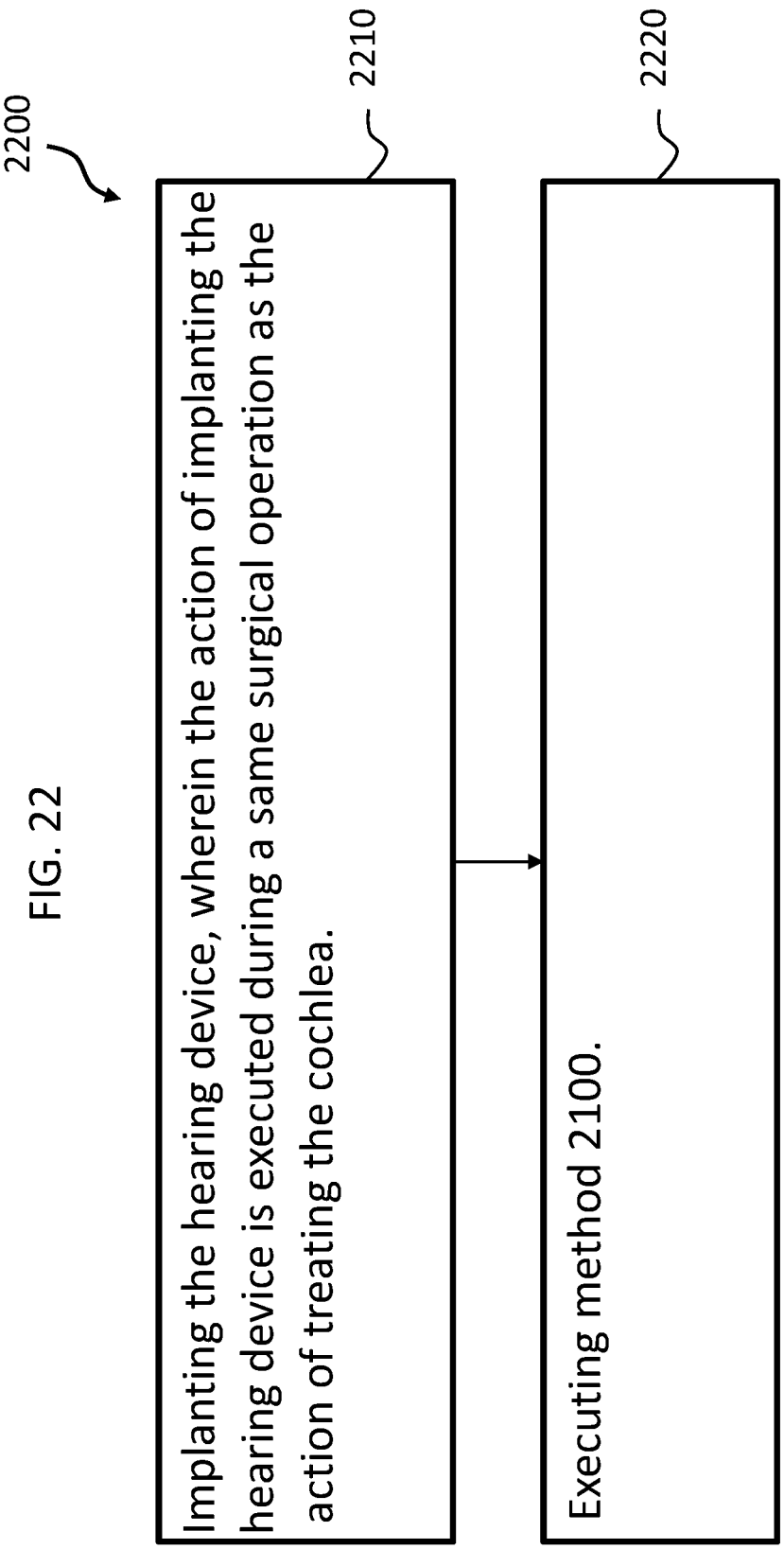

FIG. 21 is an exemplary flowchart presenting an exemplary method, method 2100, according to an exemplary embodiment. Method 2100 includes method action 2110, which includes treating a cochlea for an ailment. In this method action, the treatment is a treatment to at least one of at least partially remediate, stabilize, or at least slow a hearing impairment of the recipient. In this exemplary embodiment, the recipient has at least some residual hearing. By way of example only and not by way of limitation, in an exemplary embodiment, the action of treating the cochlea for the ailment can include delivering a therapeutic substance thereto. In an exemplary embodiment, such action of delivering the therapeutic substance can be executed utilizing one or more of the therapeutic device substance delivery systems detailed herein and/or variations thereof, as well as other types of therapeutic substance delivery systems. Method 2100 further includes method action 2120, which includes subsequent to the action of treating the cochlea (i.e., after), operating a hearing device configured to mechanically stimulate the cochlea to evoke a hearing percept. In an exemplary embodiment, the hearing device can correspond to the device of the embodiment of FIG. 7, or any of the other devices detailed herein. In this regard, by way of example only and not by way of limitation, the hearing device can be an implantable hearing device. Accordingly, some exemplary embodiments include the method represented by the flowchart in FIG. 22, which represents method 2200, which includes method action 2210, which includes implanting the hearing device. In method action 2210, the action of implanting the hearing device is executed during a same surgical operation as the action of treating the cochlea. By way of example only and not by way of limitation, in an exemplary embodiment, a surgery that is executed to implant the implantable assembly according to the embodiment of FIG. 7 detailed above will also results in the action of treating the cochlea for the ailment because that implantable assembly will also include the therapeutic substance delivery system that is integrated into the hearing device. That said, in an exemplary embodiment, the action of implanting the hearing device can be executed during a different surgical operation as the action of treating the cochlea.

In view of the above, it can be understood that embodiments include utilizing the devices and systems herein during temporal periods to only evoke a hearing percept while not providing a therapeutic substance to the cochlea during those temporal periods, at least from the delivery device (the therapeutic substance could already be in the cochlea or, in some alternate embodiments, the therapeutic substance can be mixing with the withdrawn perilymph or the like while the device is evoking a hearing percept, but not providing the therapeutic substance to the cochlea). This can also be the case with respect to embodiments utilizing the devices and systems herein to only evoke a hearing percept during certain temporal periods while not withdrawing the perilymph or the like from the cochlea for purposes of mixing such with the therapeutic substances during those temporal periods (perilymph can be withdrawn and inserted into the cochlea to evoke a hearing percept—the withdrawn fluid is just not mixed with a therapeutic substance during these actions).

Embodiments can be such that the device is configured to enable or otherwise open and/or close valves, and/or adjust the manner of opening and/or closing thereof, to reflect the movement of the actuator for purposes of delivering the perception of sound and, in some embodiments, not for the purpose of delivering therapeutic substance and/or not for the purpose of mixing a therapeutic substance with fluid withdrawn from the cochlea. Thus, in some embodiments, instead of driving the actuator to deliver therapeutic substance (or to mix such with the fluid from the cochlea), the valves are opened and closed to leverage actuation based solely on the utilitarian value of evoking the perception of sound. In some embodiments, the devices, systems and/or methods detailed herein are such that only when the recipient is in quiet/only when the microphone or other sound capture device of the hearing prosthesis is not capturing sound (or, in some embodiments, even though there is noise to be captured, the hearing prosthesis has shut off the sound capture device on purpose or otherwise purposely blocked the signals from the sound capture device to the sound processor components and/or otherwise is controlled such that the sound processor does not process the signals from the sound capture device) does the actuator actuate to any degree solely for delivery of drugs.

In at least some exemplary embodiments, method 2200 can be executed during a surgical operation where, for example, a therapeutic substance is injected into the cochlea utilizing a syringe or the like, and then during that same surgical procedure, a hearing prosthesis is implanted into the recipient. Note that this method differentiates from the mere application of a therapeutic substance that results in the "body acceptance" of the implant, such as an anti-inflammation drug or an immune suppression drug. Those are drugs that are not part of the treatment that at least one of at least partially remediate or at least slow down or stabilize a hearing impairment. Those are drugs directed towards making the body conducive to the acceptance of the hearing implant. Method 2200 (and 210) is directed towards addressing the underlying hearing impairment utilizing a therapeutic substance.

To be clear, the above said, embodiments are directed towards a therapeutic substance delivery regime that is more of an ongoing regime. As will be understood by the teachings detailed above, the therapeutic substance can be delivered to the cochlea hours, days, weeks, and even months or even years after the surgery. Some additional details of this will be described in greater detail below.

In view of the above, it becomes clear that the therapeutic substance that is utilized in the embodiment of, for example, FIG. 7, can be a therapeutic substance that is injected into the cochlea to partially remediate hearing. By way of example only and not by way of limitation, beneficial drugs or other Biologics, etc., can be utilized to improve the function of the cilia and/or improve the transportation of nerve impulses and/or the generation of the nerve impulses by injecting such into the cochlea. Any other therapeutic substance that can be injected into the cochlea that can at least partially remediate a hearing impairment can be utilized in some embodiments. Still further, in view of the above, it becomes clear that the therapeutic substance can be a substance that at least slows a hearing impairment. By way of example only and not by way of limitation, hearing impairments can sometimes be associated with the loss of hearing certain frequencies but not others. In some instances, this hearing loss can be progressive. For example, high frequencies are first lost, and then as time goes on, frequencies lower than those high frequencies are lost, and then frequencies lower than those frequencies are lost etc. In an exemplary embodiment, this can occur over a temporal period of months and/or years by way of example. According to some embodiments of the method of method 2100, if a given frequency would otherwise be expected to be lost based on statistical analysis at month M in the future, executing method 2100 could result in the loss of that frequency occurring at month N, where month N is later than month M, and thus that frequency was lost later than that which would otherwise be the case in the absence of the hearing (that is, the recipient was able to hear that frequency longer than he or she otherwise would have in the absence of the treatment). To be clear, in an exemplary embodiment, the teachings herein can slow or stop hearing loss due to a specific cause (e.g., cause A), but hearing loss can occur or otherwise continue to occur due to another cause (e.g., cause B—cause B could be age related, for example, and cause A could be related to a disease, and the therapeutic substances referenced herein treat A, but not B).

Still further, as can be seen above, some exemplary embodiments of method 2100 include stabilizing the hearing impairment. By way of example only and not by way of limitation, again, with respect to the example just detailed, the frequency that would be lost at month N would instead not be lost, at least not for a statistically significant period of time. Of course, at a later date, the hearing could degrade, but for a period of time at least, the hearing loss was stabilized.

Note also that while the embodiments detailed above have focused on typical scenarios of hearing loss, it is to be understood that in some instances, there are diseases that deleteriously affect the cochlea. By way of example only and not by way of limitation, the body can incorrectly believe that tissue in the cochlea or associated there with is a substance that should be attacked by white blood cells. Thus, the body incorrectly implements its immune system against the hearing system. In some instances, the therapeutic substances could be utilized to combat that syndrome.

In some exemplary embodiments of method 2100, the recipient includes an implanted prosthesis system implanted therein, and the action of treating the cochlea and the action of operating the hearing device is executed using the same implanted prosthesis system. In this regard, by way of example only and not by way of limitation, the implanted prosthesis system can be the prosthesis system detailed above with respect to FIG. 7, etc. In an exemplary embodiment of this embodiment or the others detailed above or below, the action of treating the cochlea and/or the action of operating the hearing device are executed within Z days of each other, where Z is 5, 10, 15, 20, 25, 30, 35, 40, 45, 50, 55, 60, 65, 70, 75, 80, 85, 90, 95, 100, 110, 120, 130, 140, 150, 160,170, 180, 190, 200, 210, 220, 230, 240, 250, 260, 270, 280, 290, 300, 325, 350, 375, 400, 425, 450, 475, 500, 550, 600, 650, 700, 750, 800, 850, 900, 950, 1000, 110, 1200, 1300, 1400, 1500, 1600, 1700, 1800, 1900 or 2000 or any value or range of values therebetween in 1 day increments. In an exemplary embodiment, the action of treating the cochlea and/or the action of operating the hearing prosthesis are executed more than Z days from a surgery implanting the device and/or implanting a device that provides the treatment (e.g., the device of FIG. 5 or FIG. 7, etc.).

In an exemplary embodiment, one or more of the actions detailed herein are executed more than Z days after the last time that one or more implanted devices implanted in the recipient was accessed via an incision in the skin and/or more than Z days after the last time that one or more surgical openings in the skin were "closed." In an exemplary embodiment, the aforementioned implanted devices can be the hearing device and/or the therapeutic delivery system, and the aforementioned incision in the skin can be an incision that at least one of accesses or was executed to implant the hearing device and/or the therapeutic delivery system in the recipient and/or was executed to "charge" (put therapeutic substance in/refill) the therapeutic delivery system.

In an exemplary embodiment, the action of treating the cochlea and the action of operating the hearing device are executed without an intervening surgical procedure. In an exemplary embodiment, the action of treating the cochlea and the action of operating the hearing device are executed without an intervening surgical procedure that corresponds to accessing the hearing device and/or implanting the hearing device and/or accessing the therapeutic substance delivery system and/or implanting the therapeutic substance delivery system.

Consistent with the embodiments detailed above associated with, for example, the embodiment of FIG. 7, the action of treating the cochlea and the action of operating the hearing device both include an artificially induced flow of fluid into the cochlea and/or out of the cochlea. That said, in an exemplary embodiment where, for example, the therapeutic substance is solid based, the action of treating the cochlea can include inducing a transport of a substance from outside the cochlea into the cochlea as well as artificially inducing a flow of fluid into the cochlea and/or out of the cochlea.

In an exemplary embodiment, the recipient of method 2100 is a recipient for whom a cochlear implant is not appropriate and/or would be a last resort in general, and a last resort extremus in some scenarios, pursuant to the regulations, laws, and/or guidelines in place in at least one of Australia, New Zealand, the United States of America, the United Kingdom, the Republic of France, the Federal Republic of Germany, Japan, Brazil, the People's Republic of China, the State of California, the State of New York, the State of Texas, the Commonwealth of Pennsylvania, the State of Florida, the State of South Carolina, the State of North Carolina, the State of Arizona, the State of Nevada, the State of Michigan, the State of Illinois, or any one or more or all of the fifty states of the United States of America, as of Jul. 4, 2017. By way of example only and not by way of limitation, the aforementioned "non-appropriateness" corresponds to medical regulations and/or laws and/or guidelines with respect to non-experimental procedures and/or with respect to standards of medicine that forbid doing harm to patient even if the patient seeks such and/or even if there is a good reason to do such. For instance, a cochlear implant may be appropriate for a recipient with 70 db or more hearing, which can be described as severe to profound hearing loss.

By way of example only and not by way of limitation, the recipient of method 2100 is a recipient for whom not a substantial loss of hearing has occurred. By way of example only and not by way of limitation, the recipient of method 2100 is a recipient for whom no more than 5%, 10%, 15%, 20%, 25%, 30%, 35%, 40%, 45%, 50%, 55%, 60%, 65%, 70%, or 75% of his or her original hearing has been lost and/or such corresponds to hearing loss relative to a statistically based standard for such person at a given age such as the 50 percentile female and/or the 50 percentile male at that given age and/or irrespective of age and/or irrespective of age above 20 years of age based on the human factors engineering standard for any one or more of the aforementioned jurisdictions in the preceding paragraph as of Jul. 4, 2017, or the closest date thereto where records are available. In an exemplary embodiment, the aforementioned percentages correspond to any medically accepted standard for evaluating hearing. In an exemplary embodiment, the aforementioned percentages correspond to a percentage of decibel hearing weighed against the original hearing of the given recipient and/or weighed against the statistically based standard for one or more of frequencies 500 Hz, 750 Hz, 800, 900, 1000, 1100, 1200, 1300, 1400, 1500, 1600, 1700, 1800, 1900 or 200 Hz. In an exemplary embodiment, the recipient is a recipient for whom only high frequency hearing loss occurred and/or for whom relatively minimal hearing loss at median and/or low frequencies has occurred.

Briefly, it is noted that one or more or all of the valves detailed herein are optional. Some embodiments include one or more or all of the valves detailed herein, while other embodiments have one or more or all of the valves detailed herein removed. Any system that can enable the teachings detailed herein can be utilized in at least some exemplary embodiments.

Figure 23:
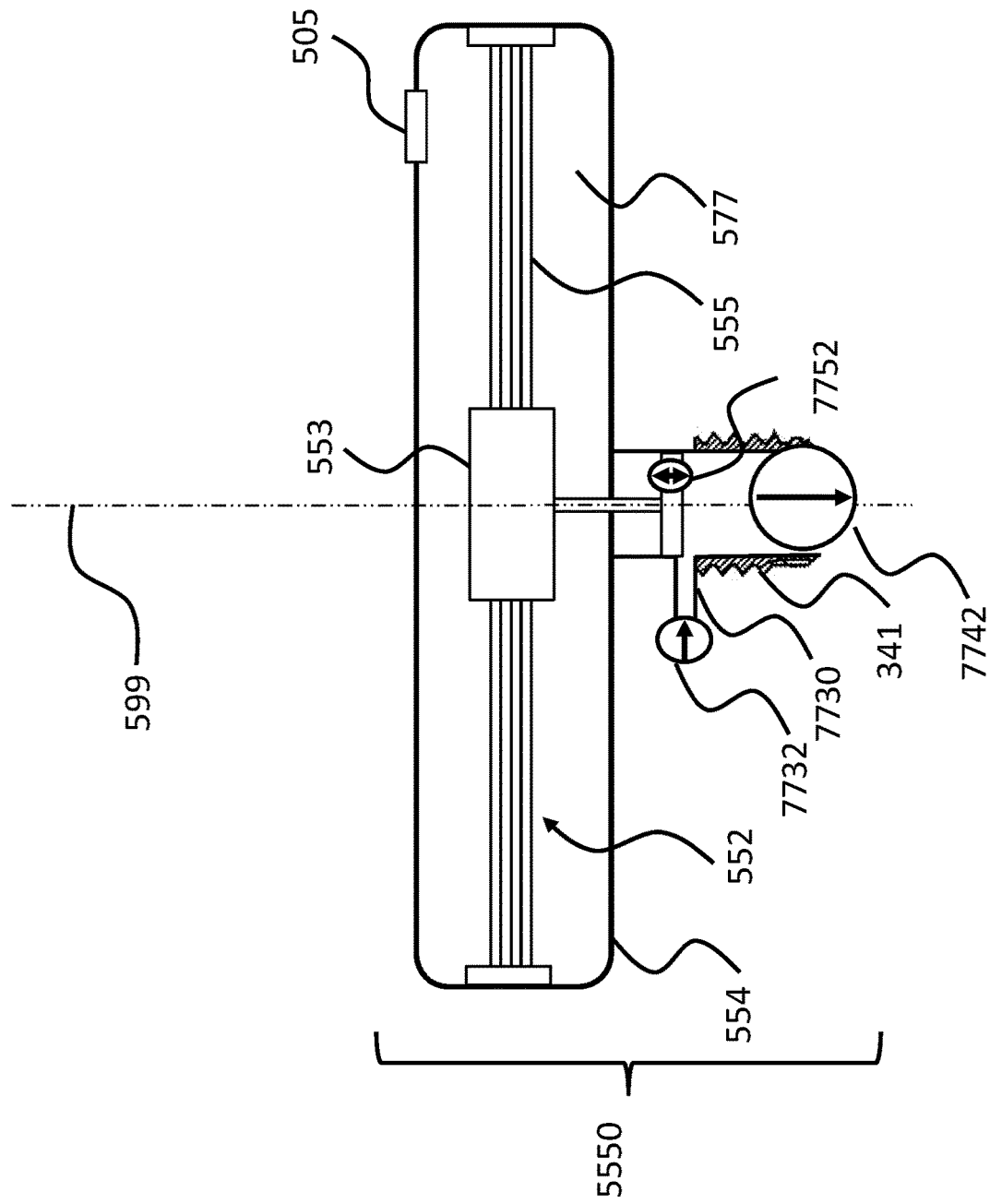
FIGS. 23-27 are schematics depicting some additional exemplary embodiments.

FIGS. 23-26 depict another exemplary embodiment of an implantable component according to an exemplary embodiment. In an exemplary embodiment, there is an implantable component 5550 of an active transcutaneous bone conduction device. Hence, in this exemplary embodiment, there can be utilitarian value with respect to adding a counterweight 553, as can be seen. However, it is to be noted that in some alternate embodiments, there is no counterweight. Also, it is noted that in at least some exemplary embodiments, the device is not an active transcutaneous bone conduction device, but instead is a device that can correspond to the device as detailed above vis-à-vis fluid flow into and/or out of the cochlea. FIG. 23 depicts a side view cross-sectional view of the implantable component 5550 which includes housing 554 which entails two housing bodies made of titanium in an exemplary embodiment, welded together at seam 444 to form a hermetically sealed housing.

In an exemplary embodiment, the implantable component 5550 is used in the embodiment of FIG. 3 and/or FIG. 4 in place of the implantable component. As can be seen, implantable component 5550 combines an actuator 552, and, optionally, an inductance coil 555 (corresponding to the coil of FIG. 3 and/or FIG. 4 detailed above). Briefly, it is noted that the vibrating actuator 552 includes a so-called counterweight/mass 553 that is supported by piezoelectric components 555. In the exemplary embodiment of FIG. 23, the piezoelectric components 555 flex upon the exposure of voltage drop, thus moving the counterweight 553. In an exemplary embodiment, this movement creates vibrations that are ultimately transferred to the recipient to evoke a hearing percept via bone conduction. Note that in some other embodiments, consistent with an embodiment were cable 328 connects to feedthrough 505, the coil is located outside of the housing 554, and is in communication therewith via feedthrough 505 or the like. It is noted that in at least some exemplary embodiments, such as where there is no counterweight, in an exemplary embodiment, the dynamic components can be limited by weight to that amount which is required for functionality of the system and essentially no more than such. In an exemplary embodiment, there are no momentum inducing and/or momentum maintaining components and/or flywheel analogous components. In an exemplary embodiment, there are no seismic mass components. In this regard, in an exemplary embodiment, the apparatuses detailed herein can be devices that are seismic masses. In at least some exemplary embodiments, devices detailed herein are configured so as to output limited amounts of vibrations and certainly much less than that which would exist with respect to evoking a hearing percept utilizing bone conduction.

To be clear, in at least some exemplary embodiments, there is no counter mass. Instead, the teachings detailed herein are directed to moving a fluid in and/or out of a cochlea to generate the perception of sound. In this regard, there is little to no induced movement of the fluid in the cochlea resulting from bone conduction. But of example only and not by way of limitation, at least 50, 60, 70, 80, 81, 82, 83, 84, 85, 86, 87, 88, 89, 90, 91, 92, 93, 94, 95, 96, 97, 98, 99 or 100% of the movement of fluid is due to non-bone conduction induced movement.

As can be understood from the schematic of FIG. 23, in an exemplary embodiment, the housing 554 entirely and completely encompasses the vibrating actuator 552, but includes feedthrough 505, so as to permit an electrical lead assembly from a receiver stimulator to communicate with the vibrating actuator 552 therein. The screw 341 is circular about the longitudinal axis 559. Back lines have been omitted for purposes of clarity in some instances. It is noted that in this exemplary embodiment, screw 341 is configured to screw into the round window and/or a cochleostomy of the cochlea and place the chamber established by the cylinder of the device 5550 into fluid medication with the inside of the cochlea in a manner analogous to the arrangement of FIG. 7 detailed above.

Figure 24:
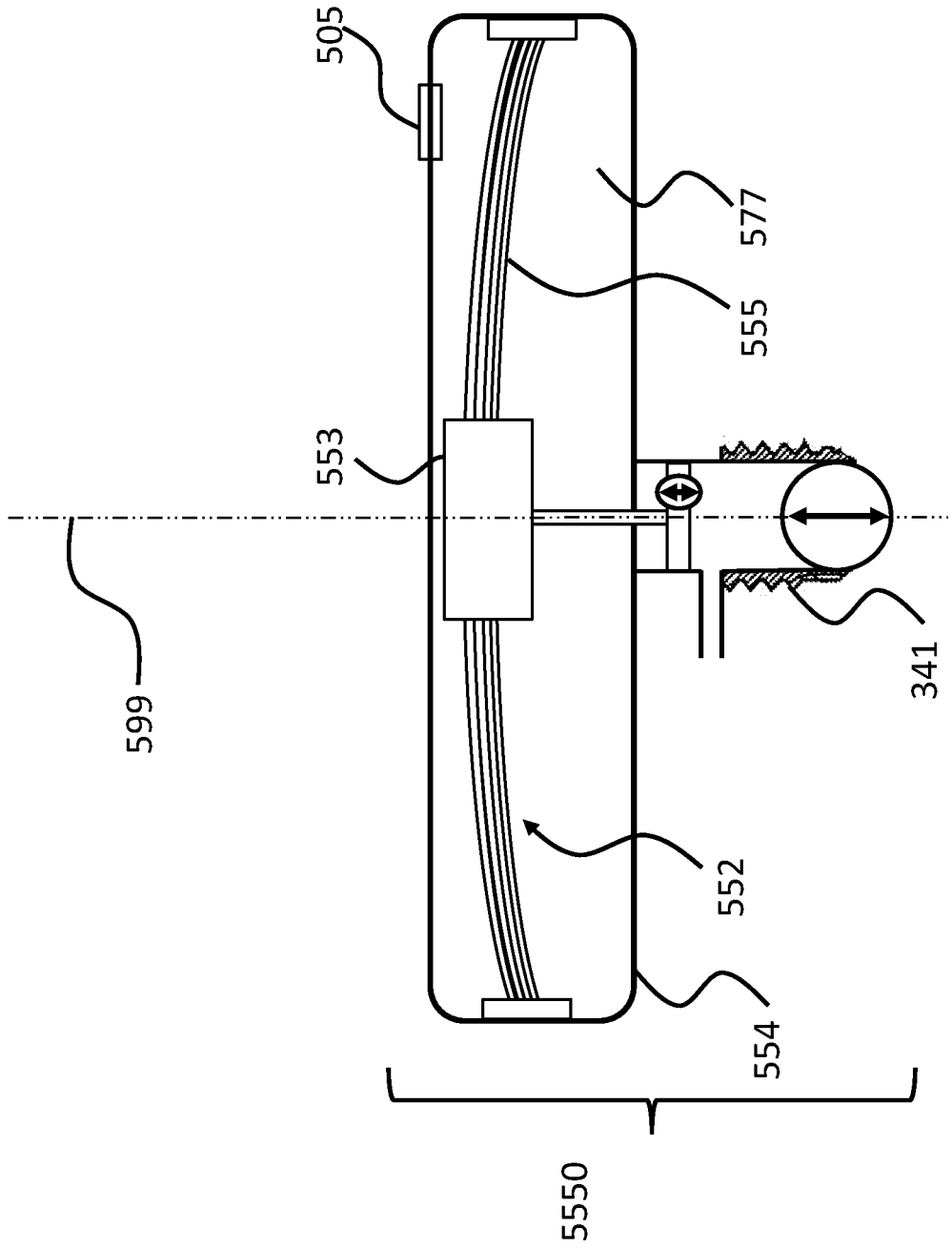
Figure 25:
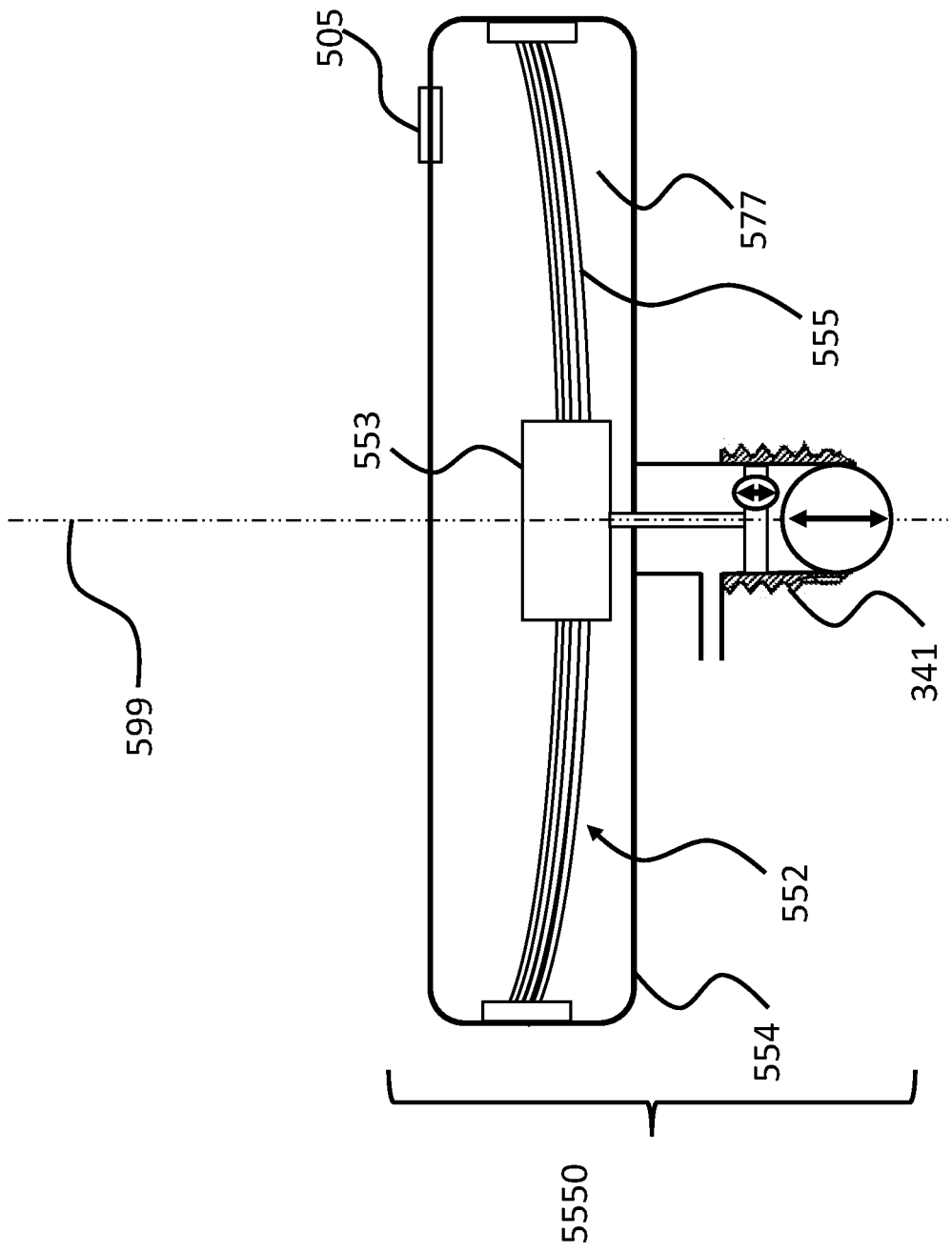

Still with reference to FIG. 23, as can be seen, there is a space 577 (sometimes referred to herein as a gap) located between the housing 554 in general, and the inside wall thereof in particular, and the counterweight 553. This space/gap has utilitarian value with respect to enabling the implantable component 5550 to function as a transducer in that, in a scenario where the implantable component is an actuator, the piezoelectric material 555 can flex, which can enable the counterweight 553 to move within the housing 554 so as to generate vibrations to evoke a hearing percept. FIG. 24 depicts an exemplary scenario of movement (exaggerated) of the piezoelectric material 555 when subjected to a voltage drop along with the movement of the counterweight 553. As can be seen, space 577 provides for the movement of the actuator 552 within housing 554 so that the counterweight 553 does not come into contact with the inside wall of the housing 554. In an exemplary embodiment, the actuator 552/the piezoelectric material 555, the counterweight 553, and the other components that enable movements of those components in response to a captured sound to evoke a hearing percept corresponds to a standard active transcutaneous bone conduction device. However, in this exemplary embodiment, as can be seen, there are a plurality of valves that are included in the implantable component 5550 along with a piston and a piston rod. In this exemplary embodiment, valve 7732 can correspond to valve 732, valve 7742 can correspond to valve 742, conduit 7730 can correspond to conduit 730 above, all at least functionally. (In an exemplary embodiment, valve 7732 is connected to tube 206 and/or to a reservoir that contains the therapeutic substance, just as can be the case with respect to valve 732 detailed above.) In this regard, operation of the valves can correspond to that detailed above with respect to the embodiment of FIG. 7, albeit with the exception that in this exemplary embodiment, in at least some instances, the hearing percept is not evoked as a result of the flow of fluid into and out of the cochlea, but instead is a result of bone conduction vibrations. That said, in an alternate embodiment, the structure of FIG. 23 can be utilized in a manner analogous to the embodiment of FIG. 7. Indeed, in an exemplary embodiment, the basic structure of the device of FIG. 23 corresponds to the device of FIG. 7, with the exception that there is a valve 7752 depicted in the piston. This valve in the piston can enable fluid flow from one side of the piston to the other side of the piston in a manner the same as or otherwise analogous to the embodiment of FIG. 7 detailed above where such a valve is present. As can be seen, when the piezoelectric material 555 is energized to deform upward, the piston is drawn upward, which enables a therapeutic substance to be drawn into the chamber established between valve 7742 and the piston in a manner analogous to the operation of the embodiment of FIG. 7 detailed above, albeit in this embodiment, valve 7742 is closed on the upstroke because this embodiment does not withdraw fluid from the cochlea, although as noted above, in other embodiments, fluid is withdrawn from the cochlea during the upstroke. Valve 7732 is then closed, the chamber being at least partially filled with a therapeutic substance. Valve 7742 is opened before or during the downstroke of the piston, thereby injecting the therapeutic substance into the cochlea. The downstroke is depicted in FIG. 25.

As noted above, valve 7752 can be a valve that enables fluid flow from the chamber established beneath the piston to behind the piston. Such can have utilitarian value with respect to an embodiment where there is no valve 7742 but it is utilitarian to avoid generating a fluid flow into and/or out of the cochlea and/or at least utilitarian to avoid generating a significant fluid flow into and/or out of the cochlea. Valve 7752 can enable the piston to reciprocate without generating the fluid flow and/or without generating a significant fluid flow. By way of example, the valve 7752 can reduce the mass volume of fluid flow into and/or out of the cochlea by at least about 50%, 60%, 70%, 80%, 90%, 91%, 92%, 93%, 94% or 95% or more relative to that which would be the case in the absence of the valve 7752, all other things being equal. Still, that said, in at least some exemplary embodiments, valve 7742 prevents the ingress and/or egress of fluid flow. Note also that the valve 7752 can have utilitarian value with respect to alleviating any pressure imbalance with respect to movement of the piston when valve 7742 is closed. Accordingly, such can reduce any resistance to the movements of the actuator that might result from pressure buildup in the chamber.

Figure 26:
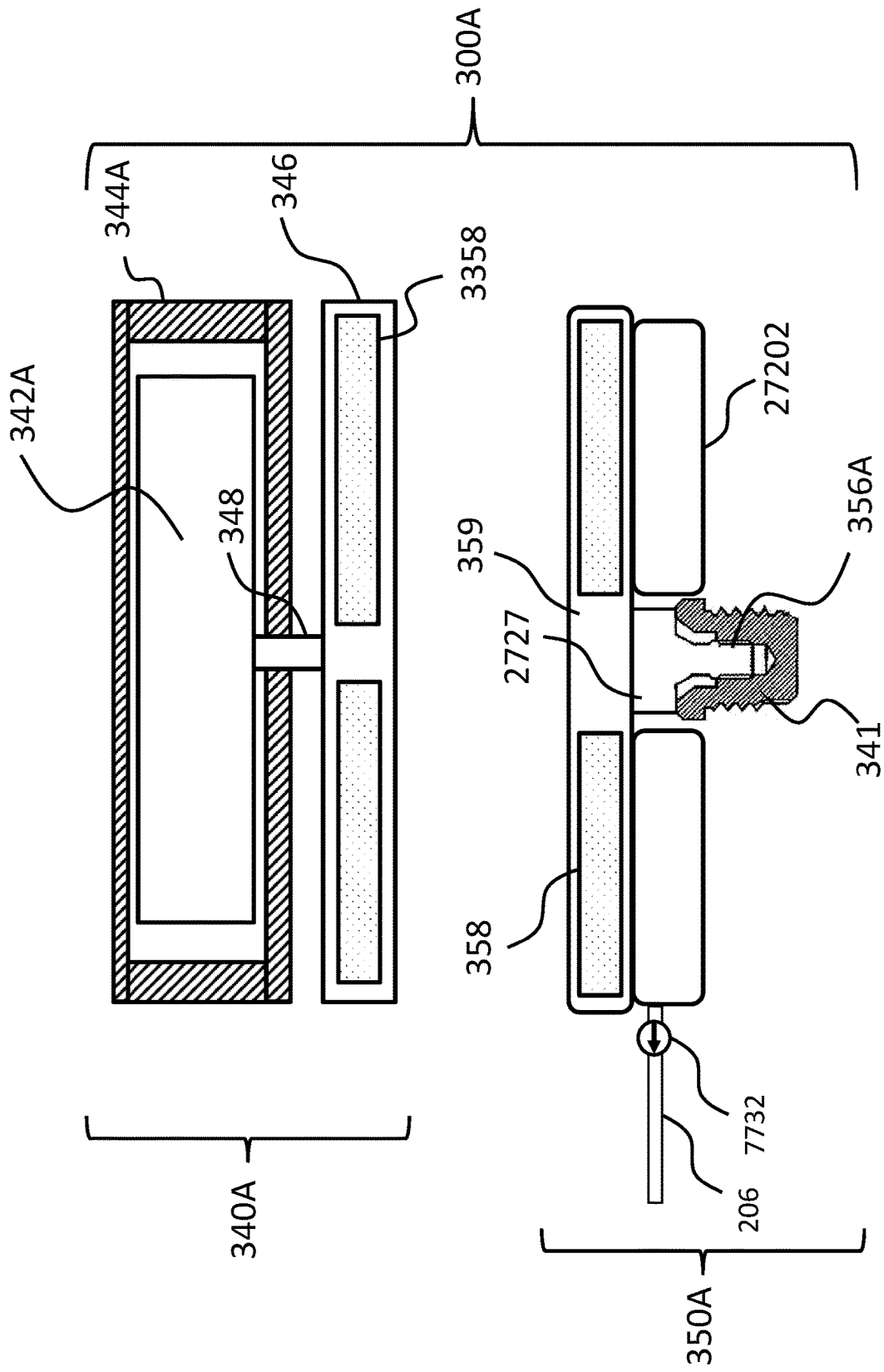

As noted above, the arrangement of FIG. 5, at least modified, can be utilized with an external component/removable component of a passive transcutaneous bone conduction device. FIG. 26 depicts such an exemplary embodiment, where there is depicted a schematic of an exemplary bone conduction device 300A. The exemplary bone conduction device 300A of FIG. 26 includes an external component 340A (the removable component, sometimes referred to in the art as a sound processor), and an implantable component 350A. The external component 340A includes a vibrating actuator represented in black-box format by reference numeral 342A. In an exemplary embodiment, the vibrating actuator can be an electromagnetic actuator. Alternatively, in some alternate embodiments, the vibrating actuator 342A can be a piezoelectric actuator. Any type of an actuator that can enable the teachings detailed herein and/or variations thereof to be practiced can be utilized in at least some exemplary embodiments. In view of FIG. 26, in an embodiment, there is an apparatus, wherein the apparatus includes components configured to evoke the mechanically based hearing percept, wherein all of the components are external to a recipient of the prosthesis (e.g., element 340A is the external component, and all of the components configured to evoke the mechanically based hearing percept are external to the recipient).

Still with reference to FIG. 26, the vibrating electromagnetic actuator 342A is enclosed in a housing 344A, as can be seen. In this embodiment, the actuator 342A is rigidly attached to skin interface portion 346 (sometimes referred to as a platform or a plate in the art), which can include a magnet 3358 embedded in a polymer or some other biocompatible substance that contacts outer skin of the recipient, via structural component 348. In this exemplary embodiment, the structural component 348 provides a vibrational conduction path such that vibrations generated by actuator 342A are transferred from the housing to the skin interface portion 346 such that those vibrations can then be transferred into the skin of the recipient to ultimately evoke a hearing percept, and, as will be detailed below, to also enable the movement of therapeutic substance from the reservoir 202 (with respect to FIG. 26, the modified reservoir 27202) to the cochlea, concomitant with the teachings above vis-à-vis FIG. 5.

With respect to the implantable component 350A, it can be seen that the implantable component includes a magnet 358 that is encased in a biocompatible housing 359. In some embodiments, magnet 358 is covered in silicone. The magnet in the housing is rigidly connected via coupling 2727 to a bone fixture 341 (in some embodiments, the magnet and/or housing is directly connected to the fixture 342) which bone fixture is configured to be screwed into the mastoid bone of the recipient. In an exemplary embodiment, coupling 2727 includes a threaded section 356A that is configured to be threaded into a female threaded receptacle of the bone fixture 341. In an exemplary embodiment, such can enable the housing 359, and thus the magnet 358, to be screwed and unscrewed from the bone fixture 341 without removing the bone fixture 341 from the skull.

As can be seen, a reservoir 27202 is positioned beneath the housing 359 of the implantable component 350A. This housing is a doughnut-shaped housing in some embodiments, and a washer shaped housing in other embodiments, with the coupling extending through the hole. Indeed, in some exemplary embodiments, the reservoir 27202 is less than 1, 2, 3, 4 or 5 millimeters in height. In an exemplary embodiment, the reservoir 27202 is configured to receive and otherwise retain a therapeutic substance therein. As can be seen, valve 7732 is positioned at an outlet port of the reservoir 27202, which can correspond to any of the valves detailed above associated with FIG. 5, or any other valves detailed herein, and valve 7732 leads to tube 206, where, while not shown, in an exemplary embodiment, leads to the cochlea, consistent with the teachings detailed above with respect to FIG. 5. In an exemplary embodiment, when the external component 340A is activated so as to generate vibrations, which vibrations are conducted via skin interface 346, into the skin over laying the implantable component 350A, the vibrations are transferred from the skin to the implantable component 350A. In an exemplary embodiment, these vibrations ultimately result in at least some of the therapeutic substance contained in reservoir 27202 being transported out of the reservoir into tube 206, valve 7732 permitting, and thus to the cochlea or at least to another component that actively pushes the therapeutic substance to the cochlea. It is also noted that in an exemplary embodiment, when the actuator of the external component is vibrated, the vibrations are also transferred into the skull of the recipient to evoke a hearing percept via bone conduction. The reservoir 27202, in some embodiments, functions to increase the degree to which the vibrations are channeled to the cochlea by way of the bone anchor, rather than, e.g., by way of contact between housing 359 and the recipient's skull.

In at least some exemplary embodiments the vibrations travel through the skin to the housing 359 and/or the magnet 358, which causes the housing 359 and/or the magnet 358 to vibrate and/or move. This vibration and/or movement can result in a compression in, e.g., the vertical direction of the reservoir 27202, which acts to force the therapeutic substance therein out through valve 7732. Alternatively and/or in addition to this, the vibrations are transferred from the housing 359 to the reservoir 27202, and, as a result of the reservoir 27202 deforming or otherwise receiving a force from the housing 359 or the bone (not shown, but immediately below the reservoir 27202, also not shown is the skin above housing 359 and the skin interface portion 346), the therapeutic substance is caused to exit the reservoir 27202. In an exemplary embodiment, the construction of the reservoir is such that compression or deformations leads to the internal volume is reduced and thus forces therapeutic substance through valve 7732. In an exemplary embodiment, there is a component in the reservoir 27202 that expands in volume when subjected to a vibration or otherwise receiving vibratory energy or otherwise compressed, the expansion thereof reducing the amount of volume that remains in the reservoir for the therapeutic substance, thus causing at least some of the therapeutic substance to leave the reservoir through valve 7732. Briefly, as will be described below, in addition to this or alternatively, the vibrations open valve 7732 (which can be a dumb valve that simply reacts in the presence of vibrations and/or magnet 346) to enable transport of therapeutic substance.

In some embodiments, the aforementioned reaction to the vibration occurs at all or substantially all frequencies of operation of the external component, and the implantable component 350A is configured such that a relatively slow transportation of the therapeutic substance from the reservoir 27202 will occur. In some embodiments, the implantable component can be manually adjusted (e.g., by exposing the valve to various magnetic fields and or RF fields) to adjust the valve to reflect the average use of the external component by a given user, enabling the implant to be customized after implantation to that user (such can also be the case prior to implantation—different valves can be used for different people/valves can be adjusted, all depending on the expected use regimes of the external component by a given recipient).

It is briefly noted that in some embodiments, the aforementioned reaction to the vibration(s) only occurs for certain frequencies. By way of example only and not by way of limitation, in an exemplary embodiment, the implantable component is configured such that the therapeutic substance is ejected or otherwise transported out of the reservoir 27202 only at frequencies below 20, 30, 40, 50, 60, 70, 80, 90 or 100 Hz and/or above frequencies of 20,000, 21,000, 22,000 Hz, and/or at certain magnitudes below or above a certain value, etc. In an exemplary embodiment, such transportation only occurs at frequencies that are outside of those that cause a hearing percept and/or at magnitudes that are insufficient to cause a hearing percept or otherwise an effective hearing percept or otherwise a hearing percept that would be distinguishable from general low-level ambient noise. That said, in an exemplary embodiment, such transportation occurs only at frequencies that would evoke a hearing percept and/or at magnitudes that would cause a hearing percept. Still further, in an exemplary embodiment, such transportation can occur within a given range of frequencies, which frequencies are rarely encountered by the recipient, but which frequencies will still cause a hearing percept. In an exemplary embodiment, the prosthesis is configured such that therapeutic substance transport occurs only during periods of quiet.

It is also noted that, concomitant with all the embodiments detailed above, the valve of the prosthesis, or, in general, the prosthesis itself, is configured such that the amount of therapeutic substance delivered to the cochlea or otherwise transported from the reservoir can vary with respect to a fixed temporal period. By way of example only and not by way of limitation, in a period of quiet, more therapeutic drug might be delivered, while in periods of loudness, less therapeutic substance might be delivered and/or visa versa (with respect to the "and," for example, the baseline could be greater drug delivery in periods of quiet, but also greater drug delivery in periods of certain levels of loudness, e.g., high levels, but not all levels of loudness). In this regard, in an exemplary embodiment, the valve 7732 can be configured such that the amount that the valve opens is correlated to these scenarios. This is also the case (the amount of therapeutic substance deliver) with respect to the arrangement where the reservoir is deformed or otherwise receives vibratory energy which causes the transport of the therapeutic substance.

It is noted that in some embodiments, the vibrations are transferred from the housing to the reservoir, while in other embodiments, alternatively and/or in addition to this, the vibrations are transferred from the skull bone to the reservoir (and/or the bone may move, thus compressing the reservoir 27202 in the vertical direction). In this regard, in an exemplary embodiment, the reservoir could be vibrationally decoupled from the housing or from the skull of the recipient. Moreover, in an exemplary embodiment, the vibrations can instead travel from the coupling 2727 to the reservoir 27202, as seen in the embodiment of FIG. 27, where the reservoir 27202 is vibrationally connected to the coupling 2727. Indeed, in an exemplary embodiment, the reservoir 27202 is vibrationally isolated from the housing and/or the skull, but vibrationally coupled to the coupling 27202. In an exemplary embodiment, by balancing or otherwise managing the resonance frequencie(s) of the implantable component, only certain frequencies will reach the reservoir 27202 (such can be executed utilizing a dampening regime or the like in some embodiments) and/or valve 7732 so as to provide an additional regime that can control the transport of therapeutic substance out of reservoir 27202 (i.e., only certain frequencies reach the reservoir 27202 and/or valve 7732), and when sufficient vibrational energy is received by the reservoir or valve, irrespective of the actuator frequency, such results in the transportation of the therapeutic substance out of the reservoir 27202.

With respect to movement of the magnet and/or the bone causing therapeutic substance to be transported from the reservoir, in an exemplary embodiment, is noted that the implanted magnet 358, which can be circular or rectangular, as is also the case with the reservoir (when looking downward from the external component) with a hole therein in some embodiments, might be of a configuration where the ends of the magnet 358 move more than the center, owing, e.g., to the fact that the center is supported by the coupling 2727 and the bone fixture 341. That is, by rough analogy, magnet 358 might flap. Thus, in an exemplary embodiment, the deflection of the reservoir 27202 might be more at the outer edges then at the inside/location proximate the coupling 2727/fixture 341. In an exemplary embodiment, the reservoir and/or the magnet 358 and/or the housing 359 can be configured to compensate for such. By way of example only and not by way of limitation, the underside of the magnet 358 could be curved or tapered upwards with location away from the center thereof such that movement of the magnet will cause uniform compression on the reservoir. Alternatively and/or in addition to this, the reservoir 27202 can be likewise configured but the top surface curves downward with location away from the center.

Also, in some embodiments, the bone conduction device is configured such that it is the skull that results in more deformation than the magnet and/or the housing, or at least the skull also as deformation that can impact the forces on the reservoir. In an exemplary embodiment, such can be mitigated by, for example, isolating the reservoir from the skull and/or isolating the reservoir from the magnet/housing, so that the force is imparted on the reservoir are single source forces, and thus there is only one movement that needs to be accounted for. Indeed, in an exemplary embodiment, if the movement of the skull is uniform over the surface area, there can be utilitarian value with respect to completely isolating the reservoir from the magnet, where the movement of the magnet may not necessarily be uniform (e.g., the skull is more uniform in movement). Any device, system and/or method that can compensate or otherwise take into account the fact that the skull and/or the magnet and/or the housing might move and/or might move in a non-linear manner and/or a non-uniform manner can be utilized at least some exemplary embodiments so as to provide for utilitarian transport of therapeutic substance from the reservoir.

It is noted that in some embodiments, the implantable component 350A can include some active components or otherwise some smart components that can control the valve 7732. By way of example, the implantable component can include a long life power source, such as a long life battery and a valve controller that is powered by the long life battery, wherein the valve 7732 can be opened and shut via a micro actuator that is also powered by the long life battery. In an exemplary embodiment, the external component can be configured so as to provide a wireless signal, such as inductance RF signal, to the valve controller (or, an antenna thereof), which can activate the valve controller to open and close the valve. In an exemplary embodiment, the valve controller can be a micro circuit or any other appropriate set of electronics which can receive a signal, evaluate or otherwise determine what the signal means (or simply that the signal is present), and output a command to the valve. That said, in an alternate embodiment, a simple gate switch can be located between the long life power source and the actuator that actuates the valve, where the gate switch reacts to, for example, vibrations from the external component and/or from an inductance RF signal generated by the external component, such that the switch opens or closes, and current is permitted to flow from the long life battery to the actuator (or not permitted to flow), thus causing the actuator to actuate and thus open the valve. In this regard, in an exemplary embodiment, the external component includes the aforementioned RF inductance transmitter and is configured to transmit an inductance signal to the implanted component. When the external component is utilized, or, in some embodiments, simply turned on, and placed against the skin of the recipient, the external component transmits this RF inductance field, which is received by the implanted component, and the implanted component open the valve to enable therapeutic substance transport from the reservoir.

Briefly, FIG. 27 also includes the feature of a passage 2887 that can enable a syringe needle or the like to extend through the housing 359 to the reservoir 27202 or to a passageway that leads to the reservoir 27202. With regard to the latter, valve 587 can enable therapeutic substance to be injected through passage 2887 into the housing 27202, and prevent substance flow in the opposite direction. It is also noted that in an exemplary embodiment, a fill reservoir can be located outside the "shadow" of the housing 359, which fill reservoir can be reached via a needle piercing the skin, and which fill reservoir is in fluid communication with the reservoir 27202, thus enabling the reservoir 27202 to be refilled without having to work around or remove the magnet/housing.

It is noted that in an alternate embodiment, a pump assembly can be located with the implantable component, which pump assembly can be driven by vibrations from the external component, to transport the therapeutic substance from the reservoir. Alternatively and/or in addition to this, the pump assembly can utilize a spring-magnet arrangement such that when the magnet of the external component is placed against the skin of the recipient, the pump actuates, if only slightly, which actuation is sufficient to transport a modicum of therapeutic substance out of the reservoir 27202. Accordingly, in an exemplary embodiment, a regime exists where therapeutic substance is transported to the cochlea every morning when the recipient places the external component against his or her head.

Still, with respect to embodiments where therapeutic substance is transported from the reservoir 27202 under certain frequencies and not others and/or under certain magnitudes of vibrational energy and not others, in an exemplary embodiment, the valve 7732 can be configured to react to those vibrations. By way of example only and not by way of limitation, the valve 7732 can have a resonance frequency such that the valve will open at certain frequencies and not others (e.g., only at low frequencies, only at high frequencies). (In some embodiments, the valve opens at all frequencies). In such exemplary embodiments, the reservoir 27202 could be over pressured such that it is not the vibrations that provide the energy for the therapeutic substance to be transported from the reservoir, as opposed to some of the other exemplary embodiments. A combination of overpressure and vibrational energy can be used.

In at least some exemplary embodiments, the external component is configured so as to enter a "deliver therapeutic substance" mode. By way of example only and not by way of limitation, the external component can include a sound processor that is configured to receive a signal indicative of ambient sound, process that signal, and cause the actuator 342A to actuate in response thereto, thus evoking a hearing percept at various frequencies based on the captured sound. In an exemplary embodiment, the sound processor or other device of the external component, such as a dedicated integrated circuit and/or a separate processor programmed to execute the processes detailed herein and/or variations thereof, is configured to control the actuator to vibrate at a certain frequency and/or at a certain magnitude or otherwise in a certain manner so as to enable the transportation of the therapeutic substance from the reservoir through valve 7732. Again, consistent with the teachings detailed above, in an exemplary embodiment, the sound processor or other device is configured so as to only permit the actuator to vibrate at certain frequencies and/or at certain magnitudes and/or for certain periods of time upon an affirmative desire to enable the transportation of therapeutic substance out of housing 27202. Thus, in an exemplary embodiment, the external component is configured with an input device, such as a toggle switch or a button, that enables a recipient or a caregiver to place the external device into the "deliver therapeutic substance" mode, which will cause the processor or other circuitry of the external component to cause the actuator 342A to actuate in a certain manner that will results or otherwise enable therapeutic substance to be transported from the reservoir 27202, whereas when not in that mode, the actuator 342A will not vibrate accordingly. Thus, with respect to embodiments that include a controller that variously controls the apparatus to deliver the therapeutic substance from outside the cochlea to inside the cochlea without evoking the mechanically based hearing percept, the processor just detailed or the dedicated integrated circuit just detailed and/or the separate processor programmed to execute a process, such as this process, can be used a the controller. Further, with respect to embodiments that include an external component configured to variously control the apparatus to evoke the mechanically based hearing percept without delivering the therapeutic substance from outside the cochlea to inside the cochlea and to evoke the mechanically based hearing percept while also delivering the therapeutic substance from outside the cochlea to inside the cochlea.

In an exemplary embodiment, the external component can be configured to automatically enter that "deliver therapeutic substance" mode without input from the recipient, such as by way of example only and not by way of limitation, based on an internal calendar and/or timer. That said, in an alternate embodiment, a recipient can speak out loud a rhythm or whistle or otherwise create a noise having a recognizable pattern that will be received by the external component and recognized as input commanding it to enter the "deliver therapeutic substance" mode. Indeed, a quasi-voice recognition system can be utilized by the sound processor. In such an exemplary embodiment, in some instances but not others, there may be no dedicated switch or the like cause the external component to enter the therapeutic substance transport mode. It is noted that the "deliver therapeutic substance" mode can also be used to activate the aforementioned RF inductance field that will be received by the implantable component.

In view of the above, it can be seen that FIG. 26 and FIG. 27 provide a prosthesis including an apparatus (e.g., bone conduction device 300A of FIG. 26, implantable active transcutaneous bone conduction device 5550, the implantable internal component 744 of FIG. 6D, etc., wherein the apparatus is the structure that executes the following) configured to deliver or a means for delivering (e.g., bone conduction device 300A of FIG. 26, implantable active transcutaneous bone conduction device 5550, the implantable internal component 744 of FIG. 6D, etc., wherein the means for executing the following is the structure to do so) a therapeutic substance from outside a cochlea to inside the cochlea and configured to evoke a mechanically based hearing percept. 300A is an example of the aforementioned apparatus, and device 5550 is also an example, as is the device of FIG. 7 (with or without the cable 452) and the implantable internal component of FIGS. 6c and 6D (by way of example). In some embodiments, this is the only hearing percept that is evoked by the prosthesis (there could be residual hearing in some embodiments, but that is not evoked by the prosthesis). In this embodiment, the apparatus includes a passive transcutaneous bone conduction device configured to evoke the mechanically based hearing percept and at least enable transportation of the therapeutic substance from outside the cochlea to inside the cochlea. Also in view of the above, it can be seen that FIGS. 26 and 27 enable an embodiment of method 2100 where the hearing prosthesis is a passive transcutaneous bone conduction device, which method further includes the action of transporting a therapeutic substance from outside the cochlea to inside the cochlea of the recipient at least partially due to operation of the hearing prosthesis (at least partially encompasses embodiments where there is, for example, an over pressurization of the reservoir and/or an active component that drives the therapeutic substance. Of course, in some embodiments, the method of 2100 further includes the action of transporting a therapeutic substance from outside the cochlea to inside the cochlea of the recipient completely due to operation of the hearing prosthesis.

In still other embodiments, the mechanical vibrations that generate the perception of sound are generated by a hearing prostheses without any implantable components (e.g., a traditional hearing aid), albeit in some embodiment, without any active components (the implanted magnet of the passive transcutaneous bone conduction device could be present). In these embodiments, the implantable drug pump is an active system with its own components for pumping therapeutic substance into the cochlea or otherwise enabling therapeutic substance transport therein. Still, delivery of therapeutic substance to the cochlea can be based on or correlated to the presence or level of ambient sound. Thus, traditional hearing aids and active implantable drug pumps can share circuitry that senses and processes sound. Such devices also include wireless communication circuitry such that the traditional hearing aid can, upon detection of or the absence of sounds of a certain level trigger the delivery of drugs to the cochlea.

Thus, there can be embodiments where a therapeutic substance delivery system and a hearing prosthesis, which delivers the perception of sound mechanically (as opposed to, for example electrically), can operate together and effectively share components to function.

By way of example only and not by way of limitation, the sound processor of the external component of the passive transcutaneous bone conduction device, or the sound processor of the other prostheses detailed herein, such as the embodiments of FIG. 6D, can be used to evaluate incoming signals from a sound capture device such as microphone, and output a signal that can be utilized to evoke a hearing percept in the traditional sense, and also output a signal that can be utilized as a basis to control therapeutic substance delivery. In an exemplary embodiment, the signals can be one and the same. For example, the output signal could be a signal that includes data indicative of a magnitude about the energy of the actuator that evokes a hearing percept. There can be a component, such as a processor or a set of electronics that are designed to extract the magnitude data of the signal, and analyze that signal and determine, based on the signal, the relative loudness of the ambient sound, and control the therapeutic substance delivery system accordingly (by outputting a signal to a valve or actuator of the delivery system). If the component that extracts the magnitude data determines that the magnitude is high, such would be indicative of a loud environment, for example, and the therapeutic substance delivery system would deliver the therapeutic substances accordingly, and the same for a low or medium loudness sound(s), etc. That said, in an alternate embodiment, two separate signals can be output depending upon the mode in which the overall prosthesis is operating—a first signal that can be sent to the actuator of the hearing prosthesis, and a second signal that can be sent to the therapeutic substance delivery system that is utilized to control or otherwise utilize as a basis for the operation of the therapeutic substance delivery system. The point is that electronics or other components of one subsystem can be utilized in the other subsystem and vice versa, or otherwise that shared components can be utilized to affect the functionality of the two different subsystems.

Accordingly, in an exemplary embodiment where the amount of therapeutic substance that is delivered to the cochlea is correlated in some manner to the ambient sound environment, the components that are utilized to analyze or otherwise process the captured sound so as to evoke a hearing percept utilizing hearing prostheses subsection can also be utilized to control or otherwise base therapeutic substance delivery thereupon. In some embodiments, the prostheses can be two separate systems that can work independently relative to each other, but where there can be synergy with respect to one communicating with the other and/or vice versa.

Thus, in an exemplary embodiment, such as where the therapeutic substances are delivered under a regime that correlates delivery to detected sound (which includes the absence thereof in some embodiments), the hearing prosthesis could wirelessly command the therapeutic substance delivery system to deliver therapeutic substance to the cochlea upon detecting and or processing the ambient sound (or upon determining that there is no sound). The therapeutic substance delivery system could be a drug pump that can be any drug pump that is configured to receive pump commands wirelessly, and thus in an exemplary embodiment, there could be a receiver circuit that receives an RF signal, such as an inductance signal, from an RF antenna, and reacts to that received signal to operate the pump of the therapeutic substance delivery system. In this exemplary embodiment, there would exist share components of the systems which could include, for example, the hearing prostheses circuitry that is utilized to detect and/or process the sounds. Thus, in this exemplary embodiment, two systems can act together to form an overall system that both delivers therapeutic substance to the cochlea and delivers sound to the recipient mechanically, as opposed to electrically, which actions could occur simultaneously or temporally separated from one another.

It is briefly noted that in some exemplary embodiments of the prostheses detailed herein, the device that is implanted is configured without any transcutaneous power transfer system and/or with only an intermitted recharging system and/or without any recharging system whatsoever. By way of example only and not by way of limitation, in an exemplary embodiment, the hearing prosthesis, with or without the therapeutic drug delivery features, are powered only by a battery and/or only by a capacitor. In an exemplary embodiment, the battery and/or the capacitor is not rechargeable. In an exemplary embodiment, the battery and/or the capacitor cannot be removed or otherwise replaced from the prosthesis. Accordingly, in an exemplary embodiment, the device is powered only by non-rechargeable battery. This even though the device includes a power consuming component (such as the transducer that drives a fluid into and/or out of the cochlea with respect to the embodiments detailed above and/or variations thereof). In an exemplary embodiment, one or more of the devices detailed herein and/or variations thereof are implanted into a recipient and the devices operate to evoke a hearing percept at least once per day and/or at least 1, 2, 4, 8, 12, 16, 20, 30 or 40 or 50 or 60 or 70 or 80 hours of evoked hearing percept per week and/or per month, for at least 1, 2, 3, 4, 5, 6, 7, 8, 9 or 10 years, without the power source being replaced and/or recharged. In an exemplary embodiment, the device simply remains on for at least six months, one year, 18 months, two-years, 2.5 years, 3 years, 3.5 years, 4 years, 5 years, 6 years, 7 years, 8 years, 9 years and/or 10 years or more without recharging the power source and/or without replacing the power source. In an exemplary embodiment, the aforementioned performance achievements are executed without an intervening surgery to access the device within the recited temporal periods.

It is noted that in some exemplary embodiments, the access locations to the interior of the cochlea are created utilizing tools, such as drills the like. That said, in some alternate embodiments, the delivery system detailed herein and/or variations thereof can be configured such that they are self-accessing. By way of example only and not by way of limitation, in an exemplary embodiment, the delivery device can have a sharp portion at the end of the cochlear interface portion that are configured to penetrate the round and/or oval windows, and can also include seals such that they self-seal when penetrating the round and oval windows. Still further, self-tapping components can be utilized on the components that interface with the cochlea. Note also, in an exemplary embodiment, there is a method where a partial cochleostomy is drilled into the cochlea, but it is not completely drilled into the cochlea, and the delivery device is utilized to "breakthrough" the remaining distance, thus preventing or otherwise limiting the amount of perilymph that escapes from the cochlea. Note also that in some exemplary embodiments, the tubes or otherwise tips of the delivery system can be configured to rotate and thus can be self-tapping.

In view of the above, it is to be understood that embodiments of at least some of the examples herein utilize a single actuator to both pump therapeutic substance into the cochlea and to generate vibrations to evoke hearing percepts and/or to generate fluid motion to evoke hearing percepts. Some exemplary embodiments are executed without a cochlear implant, and thus, in at least some exemplary embodiments, maintain residual hearing post implantation. In an exemplary embodiment, after implantation, at least 30, 35, 40, 45, 50, 55, 60, 65, 70, 75, 80, 85, 90, 95 or 100% of the hearing that the recipient had prior to implantation of the devices herein is maintained at least one month after implantation, which percentage of hearing is measured utilizing a standard hearing test.

In view of the above, in at least some exemplary embodiments, there can be utilitarian value with respect to having an actuator that is directly coupled to the cochlea where the recipients have at least some, including significant, residual hearing. In an exemplary embodiment, such can enable power requirements to be relatively low compared to other types of systems, thus enabling the aforementioned power management methods. In at least some exemplary embodiments, the devices systems and/or methods detailed herein operate at only relatively high frequencies, such as, by way of example only and not by way of limitation, frequencies above 800, 850, 900, 950, 1000, 1100, 1200, 1300, 1400 or 1500 Hz. Indeed, in an exemplary embodiment, there are methods that entail limiting the use of the device to frequencies above one or more of the aforementioned frequencies. In an exemplary embodiment, the device is configured to only operate at and/or above the aforementioned frequencies.

In at least some exemplary embodiments, the implanted component is devoid of a magnet other than the magnets associated with the transducer. By way of example only and not by way of limitation, there is no magnet that is utilized to hold an external device against the prostheses. In at least some exemplary embodiments, there is no inductance coil in the implanted device. In at least some exemplary embodiments, the piezoelectric base microphone is utilized to censor otherwise detect sound and is also utilized to generate a drive signal for the transducer.

In an exemplary embodiment, the implantable component does include a battery. This battery is in some embodiments, not rechargeable. In an exemplary embodiment, the reservoir containing the therapeutic substance can be depleted after a period of use. In an exemplary embodiment, there is a method that entails accessing the reservoir and refilling the reservoir and/or replacing the reservoir with a new reservoir, which the reservoir contains a new charge of therapeutic substance, and at the same time, replacing the battery. In this exemplary embodiment, the battery is replaced irrespective of whether the battery has any remaining charge. That said, in an alternative embodiment, it is the battery that is the causation of accessing the implantable component, and thus at the same time, the reservoir is refilled or otherwise replaced with a new reservoir containing the therapeutic substance.

In an exemplary embodiment, the reservoir and the power source or an integrated component or otherwise share a same chassis or otherwise support one another in some manner, such that replacement and/or removal of the reservoir results in replacement and/or removal of the power source, and vice versa. In an exemplary embodiment, the action of connecting the reservoir to the implantable component results in the automatic connection of the power source that is coupled to the reservoir to the implantable component, and/or vice versa.

In an exemplary embodiment, the battery, reservoir fill port (if present) and/or reservoir (if present) are located remote from the cochlea. By way of example only and not by way of limitation, one or more or all of these components are located above the temporal bone behind the ear, enabling ease of accessibility.

While the embodiments detailed above have been described in terms of accessing perilymph containing bodies of the cochlea, in some alternate embodiments, the teachings detailed herein can be utilized to access the endolymph containing bodies of the cochlea, such as, for example, the cochlear duct.

It is noted that any reference herein to a therapeutic substance corresponds to a disclosure of an active substance such as an active drug or an active biologic etc., and any disclosure herein to an active substance such as an active drug or the phrase active substance in the generic manner corresponds to a disclosure of an active biologic or a therapeutic substance, etc. Any active pharmaceutical ingredient that can have utilitarian value can be a therapeutic substance. Proteins can be therapeutic substances as well. It is also noted that in an at least some exemplary embodiments, an inactive fluid can be a physiological saline, which can be utilized to convey the therapeutic substance into the cochlea.

In an exemplary embodiment, therapeutic substance include but are not limited to, any of those detailed above, and can include peptides, biologics, cells, drugs, neurotrophics, etc. Any substance that can have therapeutic features if introduced to the cochlea can be utilized in some embodiments.

It is noted that any disclosure of a device and/or system herein corresponds to a disclosure of a method of utilizing such device and/or system. It is further noted that any disclosure of a device and/or system herein corresponds to a disclosure of a method of manufacturing such device and/or system. It is further noted that any disclosure of a method action detailed herein corresponds to a disclosure of a device and/or system for executing that method action/a device and/or system having such functionality corresponding to the method action. It is also noted that any disclosure of a functionality of a device herein corresponds to a method including a method action corresponding to such functionality. Also, any disclosure of any manufacturing methods detailed herein corresponds to a disclosure of a device and/or system resulting from such manufacturing methods and/or a disclosure of a method of utilizing the resulting device and/or system.

Unless otherwise specified or otherwise not enabled by the art, any one or more teachings detailed herein with respect to one embodiment can be combined with one or more teachings of any other teaching detailed herein with respect to other embodiments, and this includes the duplication or repetition of any given teaching of one component with any like component. It is also noted that embodiments can include devices systems and/or methods that specifically exclude one or more of the disclosures presented herein (i.e., it is not present).

While various embodiments of the present invention have been described above, it should be understood that they have been presented by way of example only, and not limitation. It will be apparent to persons skilled in the relevant art that various changes in form and detail can be made therein without departing from the scope of the invention.

In an embodiment, there is a prosthesis, the prosthesis comprising an apparatus configured to deliver a therapeutic substance from outside a cochlea to inside the cochlea and configured to evoke a mechanically based hearing percept. In an embodiment, this apparatus corresponds to the implant internal component 644 or implant internal component 744 described above, or to the device 5550 or 300A. In an embodiment, there is a prosthesis, comprising a first sub-system configured to deliver a therapeutic substance from outside a cochlea to inside the cochlea (the first sub-system can be the fluid delivery apparatus of FIG. 23, such as components 7732, 7730, 7752 and 7742, and the associated structure) and a second sub-system configured to evoke a mechanically based hearing percept (the second sub-system can be the piezoelectric device 552 and the counterweight 553, and the associated hardware), wherein the second sub-system includes a passive transcutaneous bone conduction component (e.g., the bone conduction device structure of FIG. 26) or an active transcutaneous bone conduction component (e.g., the bone conduction device structure of FIG. 23) configured to evoke the mechanically based hearing percept.

What is claimed is:
1. A prosthesis, comprising:
an apparatus configured to deliver a therapeutic substance from outside a cochlea to inside the cochlea and configured to evoke a mechanically based hearing percept, wherein
at least one of:
the apparatus is configured to be controlled to evoke the mechanically based hearing percept without delivering the therapeutic substance from outside the cochlea to inside the cochlea; or
the apparatus is configured to be controlled to deliver the therapeutic substance from outside the cochlea to inside the cochlea without evoking the mechanically based hearing percept.
2. The prosthesis of claim 1, wherein:
the apparatus is configured to drive fluid into and out of the cochlea, thereby evoking the mechanically based hearing percept.
3. The prosthesis of claim 1, wherein:
the apparatus is configured to drive fluid into and out of the cochlea, thereby simultaneously both evoking a hearing percept and delivering the therapeutic substance to inside the cochlea.
4. The prosthesis of claim 1, wherein:
the apparatus is configured to generate waves of fluid motion in the cochlea to evoke a hearing percept with fluid containing the therapeutic substance.
5. The prosthesis of claim 1, wherein:
the apparatus includes an electro-mechanical transducer;
the apparatus is configured such that the electro-mechanical transducer can drive the therapeutic substance from outside the cochlea to inside the cochlea; and
the apparatus is configured such that the electro-mechanical transducer can pull perilymph from inside the cochlea to outside the cochlea and then push the perilymph back to inside the cochlea, thereby evoking the hearing percept.
6. The prosthesis of claim 1, wherein:
the apparatus includes a power consuming component that drives the therapeutic substance from outside the cochlea to inside the cochlea; and
the apparatus is powered only by a non-rechargeable battery.
7. The prosthesis of claim 1, wherein:
the prosthesis is a non-bone conduction hearing prosthesis configured to evoke the mechanically based hearing percept with the ossicles intact.
8. The prosthesis of claim 1, wherein:
the prosthesis includes an implantable inductance coil, wherein the implantable inductance coil is part of an implantable component of the prosthesis; and
the prosthesis further comprises an external component including an external coil in signal communication with the implantable inductance coil and providing a signal to the implantable inductance coil based on an ambient sound captured by the external component, the external component being configured to be worn on an outside of a head of a recipient of the prosthesis.
9. The prosthesis of claim 1, wherein the apparatus includes a stimulator/receiver unit.

10. The prosthesis of claim 1, wherein:
the apparatus includes an implantable component configured to deliver the therapeutic substance from outside the cochlea to inside the cochlea; and
the apparatus includes an external component including a transducer, the external component being configured to evoke the mechanically based hearing percept.

11. The prosthesis of claim 1, wherein:
the apparatus is configured to be controlled to evoke the mechanically based hearing percept without delivering the therapeutic substance from outside the cochlea to inside the cochlea.

12. The prosthesis of claim 1, wherein:
the apparatus is configured to be controlled to deliver the therapeutic substance from outside the cochlea to inside the cochlea without evoking the mechanically based hearing percept.

13. A prosthesis, comprising:
means for delivering a therapeutic substance from outside a cochlea to inside the cochlea and evoking a mechanically based hearing percept; and
a power storage device, wherein the power storage device powers the means for delivering the therapeutic substance from outside the cochlea to inside the cochlea and evoking the mechanically based hearing percept, wherein
the prosthesis includes a wireless communication antenna and wherein the prosthesis is a dual use therapeutic substance delivery device and hearing prosthesis.

14. The prosthesis of claim 13, wherein the wireless communication antenna is an inductance coil.

15. The prosthesis of claim 14, wherein:
the inductance coil is an implantable inductance coil; and
the prosthesis further comprises:
an external component including an external coil in signal communication with the implantable inductance coil and providing a signal to the implantable inductance coil based on an ambient sound captured by the external component, the external component being configured to be worn on an outside of a head of a recipient of the prosthesis.

16. The prosthesis of claim 13, wherein:
the prosthesis is configured so that the means for delivering the therapeutic substance from outside the cochlea to inside the cochlea and evoking the mechanically based hearing percept is controllable to deliver the therapeutic substance from outside the cochlea to inside the cochlea without evoking the mechanically based hearing percept.

17. The prosthesis of claim 13, wherein:
the prosthesis is configured to evoke the mechanically based hearing percept without delivering the therapeutic substance from outside the cochlea to inside the cochlea and to evoke the mechanically based hearing percept while also delivering the therapeutic substance from outside the cochlea to inside the cochlea using the means for delivering the therapeutic substance from outside the cochlea to inside the cochlea and evoking a mechanically based hearing percept.

18. The prosthesis of claim 13, wherein:
the prosthesis is configured so that the means for delivering the therapeutic substance from outside the cochlea to inside the cochlea and evoking the mechanically based hearing percept is controllable to evoke the mechanically based hearing percept without delivering the therapeutic substance from outside the cochlea to inside the cochlea.

19. The prosthesis of claim 13, wherein the means for delivering the therapeutic substance from outside the cochlea to inside the cochlea includes a stimulator/receiver unit.

20. A prosthesis, comprising:
a fluid pump;
a chamber in fluid communication with the fluid pump; and
a cochlea interface component in fluid communication with the chamber, wherein
the fluid pump, the chamber and the cochlea interface component are configured to deliver a therapeutic substance from outside the cochlea to inside the cochlea of a recipient,
the prosthesis is configured to evoke a mechanically based hearing percept, and
at least one of:
the prosthesis is configured to control the fluid pump to control a movement of fluid into and out of the cochlea, the fluid containing the therapeutic substance, while not evoking the mechanically based hearing percept; or
the prosthesis is configured to control the fluid pump to control the movement of fluid into and out of the cochlea, the fluid containing the therapeutic substance, while evoking a hearing percept different from the mechanical based hearing percept.

21. The prosthesis of claim 20, wherein:
the prosthesis is configured to evoke the mechanically based hearing percept by controlling the fluid pump to control a movement of fluid into and out of the cochlea, the fluid containing the therapeutic substance.

22. The prosthesis of claim 20, further comprising:
a vibrating actuator, wherein the prosthesis is configured to control the vibrating actuator to evoke the mechanically based hearing percept.

23. The prosthesis of claim 20, wherein:
the prosthesis is configured to control the fluid pump to control the movement of fluid into and out of the cochlea, the fluid containing the therapeutic substance, while not evoking the mechanically based hearing percept.

24. The prosthesis of claim 20, wherein:
the prosthesis is configured to control the fluid pump to control the movement of fluid into and out of the cochlea, the fluid containing the therapeutic substance, while evoking a hearing percept different from the mechanical based hearing percept.

25. A prosthesis, comprising:
a first sub-system configured to deliver a therapeutic substance from outside a cochlea to inside the cochlea and a second sub-system configured to evoke a mechanically based hearing percept, wherein
the second sub-system includes a passive transcutaneous bone conduction component or an active transcutaneous bone conduction component configured to evoke the mechanically based hearing percept.

26. The prosthesis of claim 25, wherein:
the first sub-system is configured to flow fluid into and out of the cochlea at a frequency outside of an audible range.

27. The prosthesis of claim 25, wherein:
the prosthesis includes an external component that is configured to evoke the mechanically based hearing percept.

28. The prosthesis of claim 25, further comprising:
an input device that is part of an external component that is in signal communication with an implantable component, the external component being configured to control the second sub-system based on input into the input device, wherein the second sub-system is part of the implantable component of the prosthesis.

29. The prosthesis of claim 25, wherein the prosthesis consists of an external component configured to be worn on a head of a recipient of the prosthesis external to the recipient, and an implantable component configured to be implanted in the recipient.

* * * * *